US009169514B2

(12) United States Patent
Jia et al.

(10) Patent No.: US 9,169,514 B2
(45) Date of Patent: Oct. 27, 2015

(54) DETECTING NUCLEIC ACID VARIATIONS WITHIN POPULATIONS OF GENOMES

(75) Inventors: Yanwei Jia, Waltham, MA (US); J. Aquiles Sanchez, Framingham, MA (US); John E. Rice, Quincy, MA (US); Lawrence J. Wangh, Auburndale, MA (US)

(73) Assignee: Brandeis University, Waltham, MA (US)

( * ) Notice: Subject to any disclaimer, the term of this patent is extended or adjusted under 35 U.S.C. 154(b) by 163 days.

(21) Appl. No.: 13/991,056

(22) PCT Filed: Dec. 1, 2011

(86) PCT No.: PCT/US2011/062794
§ 371 (c)(1),
(2), (4) Date: Sep. 19, 2013

(87) PCT Pub. No.: WO2012/075231
PCT Pub. Date: Jun. 7, 2012

(65) Prior Publication Data
US 2014/0024033 A1    Jan. 23, 2014

Related U.S. Application Data

(60) Provisional application No. 61/419,639, filed on Dec. 3, 2010.

(51) Int. Cl.
*C12Q 1/68* (2006.01)

(52) U.S. Cl.
CPC .................... *C12Q 1/6858* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis et al. | |
| 4,965,188 A | 10/1990 | Mullis et al. | |
| 5,066,584 A | 11/1991 | Gyllensten et al. | |
| 5,487,972 A | 1/1996 | Gelfand et al. | |
| 5,925,517 A | 7/1999 | Tyagi et al. | |
| 5,994,056 A | 11/1999 | Higuchi et al. | |
| 6,150,097 A | 11/2000 | Tyagi et al. | |
| 7,517,977 B2 | 4/2009 | Wangh et al. | |
| 2008/0193934 A1* | 8/2008 | Wangh | 435/6 |
| 2010/0099110 A1* | 4/2010 | Will et al. | 435/6 |
| 2012/0088275 A1 | 4/2012 | Wangh et al. | |

FOREIGN PATENT DOCUMENTS

| | | |
|---|---|---|
| EP | 1185546 | 5/2008 |
| WO | 03/054233 | 7/2003 |
| WO | 2011/050173 | 4/2011 |

OTHER PUBLICATIONS

Jia et al. (Dilute-'N'-Go dideoxy sequencing of all DNA strands generated in multiplex LATE-PCR assays, Nucleic Acids Res. Jun. 2010;38(11):e119. Epub Feb. 26, 2010).*
Vestheim et al. (Application of Blocking Oligonucleotides to Improve Signal-to-Noise Ratio in a PCR, Methods Mol Biol. 2011;687:265-74).*
Peano et al. (Development of a peptide nucleic acid polymerase chain reaction clamping assay for semiquantitative evaluation of genetically modified organism content in food, Anal Biochem. Sep. 15, 2005;344(2):174-82).*
Parsons et al. (Detection of a mouse H-ras codon 61 mutation using a modified allele-specific competitive blocker PCR genotypic selection method, Mutagenesis. Nov. 1998;13(6):581-8).*
Orou et al. (Allele-specific competitive blocker PCR: a one-step method with applicability to pool screening, Hum Mutat. 1995;6(2):163-9).*
Parsons et al. (Genotypic selection methods for the direct analysis of point mutations, Mutat Res. Oct. 1997;387(2):97-121).*
Syvanen (Accessing Genetic Variation: Genotyping Single Nucleotide Polymorphisms, Nat Rev Genet. Dec. 2001;2(12):930-42).*
Pierce et al. (Linear-After-the-Exponential Polymerase Chain Reaction and Allied Technologies, Methods Mol Med. 2007;132:65-85).*
Papp et al. (Single Nucleotide Polymorphism Genotyping Using Allele-Specific PCR and Fluorescence Melting Curves, Biotechniques. May 2003;34(5):1068-72).*
Gale et al. (Rapid typing of STRs in the human genome by HyBeacon® melting, Org Biomol Chem. Dec. 21, 2008;6(24):4553-9. Epub Oct. 30, 2008).*
Thelwell et al. (Mode of action and application of Scorpion primers to mutation detection, Nucl. Acids Res. (2000) 28 (19): 3752-3761).*
Hosono et al. (Multiplex PCR-Based Real-Time Invader Assay (mPCR-RETINA): A Novel SNP-Based Method for Detecting Allelic Asymmetries Within Copy Number Variation Regions, Hum Mutat. Jan. 2008;29(1):182-9).*
Zhou et al. (Enrichment and Detection of Rare Alleles by Means of Snapback Primers and Rapid-Cycle PCR, Clin Chem. May 2010;56(5):814-22. Epub Mar. 18, 2010).*
Allawi and Santalucia, "Thermodynamics and NMR of internal G.T mismatches in DNA," 1997, Biochem. 36: 10581-10594.
Eckert and Kunkel, "DNA polymerase fidelity and the polymerase chain reaction," 1991 PCR Methods Appl., 1991, 1(1):17-24.
Gyllensten and Erlich, "Generation of Single-Stranded DNA by the Polymerase Chain Reaction and Its Application to Direct Sequencing of the HLA-DQA Locus," Proc. Natl. Acad. Sci. (USA), 1988, 85: 7652-7656.
Haas et al., "Primer design for large scale sequencing," Nucl. Acids Res., 1998, 26(12):3006-3012.

(Continued)

Primary Examiner — Stephanie K Mummert
Assistant Examiner — Aaron Priest
(74) Attorney, Agent, or Firm — Foley Hoag LLP

(57) ABSTRACT

This disclosure relates to amplification and detection of a rare variant or variants of a DNA sequence in an abundant variant of the sequence, such as detection of a low-level somatic mutations and minority alleles in an excess of normal nucleic acid target sequences.

17 Claims, 26 Drawing Sheets

(56) References Cited

OTHER PUBLICATIONS

Hillier and Green, "OSP: a computer program for choosing PCR and DNA sequencing primers," PCR Methods Appl., 1991, 1(2):124-128.
International Search Report, International Patent Application No. PCT/US2011/062794, mailed Mar. 28, 2012, 5 pages.
Jia et al., "Dilute-'N'-Go dideoxy sequencing of all DNA strands generated in multiplex LATE-PCR assays," Nucl. Acids Res., 2010, 38(11): e119.
Le Novere, "Melting, Computing the Melting Temperature of Nucleic Acid Duplex," Bioinformatics, 2001, 17(12): 1226-7.
Li et al., "PRIMO: A primer design program that applies base quality statistics for automated large-scale DNA sequencing," Genomics, 1997, 40(3):476-85.
Marras et al., "Multiplex detection of single-nucleotide variations using molecular beacons," Genetic Analysis: Biomolecular Engineering, Elsevier Science Publishing US, 1999, 14: 151-156.
Marras et al., "Efficiencies of fluorescence resonance energy transfer and contact-mediated quenching in oligonucleotide probes," Nucleic Acids Research, 2002, 30 No. 21 e122.
Milbury et al., "PCR-Based Methods for the Enrichment of Minority Alleles and Mutations," Clinical Chemistry, 2009, 55(4): 632-640.
Orou et al., "Allele-Specific Competitive Blocker PCR: A one-step Method with Applicability to Pool Screening," Human Mutation, US, 1995, 6(2): 163-169.
Parsons et al., "Allele-Specific Competitive Blocker-PCR Detection of Rare Base Substitution," Methods in Molecular Biology, Humana Press Inc., 2005, 291: 235-245.
PCR Protocols, a guide to Methods and Applications, Innis et al. eds., Academic Press San Diego, CA (USA) 1990 (Table of Contents only).
Pierce et al., "Linear-After-The-Exponential (LATE)-PCR: Primer design criteria for high yields of specific single-stranded DNA and improved real-time detection," PNAS (USA), 2005, 102(24): 8609-8614.
Pierce et al., "QuantiLyse: Reliable DNA Amplification from Single Cells," Biotechniques, 2002, 32(5), 1106-1111.
Proutski and Holmes, "Primer Master: a new program for the design and analysis of PCR primers,"Computer Appl Biosci, 1996, 12(3):253-5.
Rice et al., "Monoplex/multiplex linear-after-the-exponential-PCR assays combined with PrimeSafe and Dilute-'N'-Go sequencing," Nature Protocols, 2007, 2(10): 2429-2438.
Rychlik and Rhoads, "A computer program for choosing optimal oligonucleotides for filter hybridization, sequencing and in vitro amplification of DNA," Nucl. Acids Res, 1989, 17(21):8543-51.
Sanchez et al., "Linear-After-The-Exponential (LATE)-PCR: An advanced method of asymmetric PCR and its uses in quantitative real-time analysis," Proc. Nat. Acad. Sci. (USA), 2004, 101: 1933-1938.
Santalucia, "A unified view of polymer, dumbbell, and oligonucleotide DNA nearest-neighborthermodynamics," PNAS (USA), 1998, 95(4):1460-1465.
Seyama et al., "A novel blocker-PCR method for detection of rare mutant alleles in the presence of an excess amount of normal DNA," Nucleic Acids Research, Oxford University Press, GB, 1992, 20(10): 2493-2496.
Tindall and Kunkel, "Fidelity of DNA synthesis by the *Thermus aquaticus* DNA polymerase," Biochemistry, 1988, 27(16): 6008-6013.
Wetmur, "DNA Probes: Applications of the Principles of Nucleic Acid Hybridization," Crit. Rev. Biochem. Mol. Biol., 1991, 26(3-4):227-259.
Zhou et al., "Rare allele enrichment and detection by a allel-specific PCR, competitive probe blocking and melting analysis," BioTechniques, 2011, 50(5): 311-316.
U.S. Appl. No. 61/202,565.

\* cited by examiner

SEQUENCE LISTING

```
<160> NUMBER OF SEQ ID NOS: 30

<210> SEQ ID NO 1
<211> LENGTH: 18
<212> TYPE: DNA
<213> ORGANISM: Artificial Sequence
<220> FEATURE:
<223> OTHER INFORMATION: Synthetic

<400> SEQUENCE: 1
gcctacgcca ccagctcc                                                 18

<210> SEQ ID NO 2
<211> LENGTH: 26
<212> TYPE: DNA
<213> ORGANISM: Artificial Sequence
<220> FEATURE:
<223> OTHER INFORMATION: Synthetic

<400> SEQUENCE: 2
cgccgcctac gccaccagct ccggcg                                        26

<210> SEQ ID NO 3
<211> LENGTH: 28
<212> TYPE: DNA
<213> ORGANISM: Artificial Sequence
<220> FEATURE:
<223> OTHER INFORMATION: Synthetic

<400> SEQUENCE: 3
gcgccgccta cgccaccagc tccggcgc                                      28

<210> SEQ ID NO 4
<211> LENGTH: 30
<212> TYPE: DNA
<213> ORGANISM: Artificial Sequence
```

<220> FEATURE:
<223> OTHER INFORMATION: Synthetic

<400> SEQUENCE: 4
cgcgccgcct acgccaccag ctccggcgcg                            30

<210> SEQ ID NO 5
<211> LENGTH: 32
<212> TYPE: DNA
<213> ORGANISM: Artificial Sequence
<220> FEATURE:
<223> OTHER INFORMATION: Synthetic

<400> SEQUENCE: 5
ccgcgccgcc tacgccacca gctccggcgc gg                         32

<210> SEQ ID NO 6
<211> LENGTH: 34
<212> TYPE: DNA
<213> ORGANISM: Artificial Sequence
<220> FEATURE:
<223> OTHER INFORMATION: Synthetic

<400> SEQUENCE: 6
gccgcgccgc ctacgccacc agctccggcg cggc                       34

<210> SEQ ID NO 7
<211> LENGTH: 30
<212> TYPE: DNA
<213> ORGANISM: Artificial Sequence
<220> FEATURE:
<223> OTHER INFORMATION: Synthetic

<400> SEQUENCE: 7
gtagttggag ctggtggcgt aggcaagagt                            30

<210> SEQ ID NO 8
<211> LENGTH: 30
<212> TYPE: DNA
<213> ORGANISM: Artificial Sequence
<220> FEATURE:
<223> OTHER INFORMATION: Synthetic

<400> SEQUENCE: 8
gtagttggag ctgatggcgt aggcaagagt                            30

<210> SEQ ID NO 9
<211> LENGTH: 14
<212> TYPE: DNA
<213> ORGANISM: Artificial Sequence
<220> FEATURE:
<223> OTHER INFORMATION: Synthetic

<400> SEQUENCE: 9
actcttgcct acgc                                             14

<210> SEQ ID NO 10
<211> LENGTH: 16
<212> TYPE: DNA
<213> ORGANISM: Artificial Sequence
<220> FEATURE:
<223> OTHER INFORMATION: Synthetic

<400> SEQUENCE: 10
gtggagtatt tgatag                                           16

<210> SEQ ID NO 11
<211> LENGTH: 22
<212> TYPE: DNA
<213> ORGANISM: Artificial Sequence
<220> FEATURE:
<223> OTHER INFORMATION: Synthetic

<400> SEQUENCE: 11
caagaacatg tcacacataa tg                                              22

<210> SEQ ID NO 12
<211> LENGTH: 145
<212> TYPE: DNA
<213> ORGANISM: Artificial Sequence
<220> FEATURE:
<223> OTHER INFORMATION: Synthetic

<400> SEQUENCE: 12
ctggtggagt atttgatagt gtattaacct tatgtgtgac atgttctaat atagtcacat     60
tttcattatt tttattataa ggcctgctga aaatgactga atataaactt gtggtagttg    120
gagctggtgg cgtaggcaag agtgc                                          145

<210> SEQ ID NO 13
<211> LENGTH: 145
<212> TYPE: DNA
<213> ORGANISM: Artificial Sequence
<220> FEATURE:
<223> OTHER INFORMATION: Synthetic

<400> SEQUENCE: 13
ctggtggagt atttgatagt gtattaacct tatgtgtcac atgttctaat atagtcacat     60
tttcattatt tttattataa ggcctgctga aaatgactga atataaactt gtggtagttg    120
gagctgatgg cgtaggcaag agtgc                                          145

<210> SEQ ID NO 14
<211> LENGTH: 145
<212> TYPE: DNA
<213> ORGANISM: Artificial Sequence
<220> FEATURE:
<223> OTHER INFORMATION: Synthetic

<400> SEQUENCE: 14
ctggtggagt atttgatagt gtattaacct tatgtgtgac atgttctaat atagtcacat     60
tttcattatt tttattataa ggcctgctga aaatgactga atataaactt gtggtagttg    120
gagctgatgg cgtaggcaag agtgc                                          145

<210> SEQ ID NO 15
<211> LENGTH: 145
<212> TYPE: DNA
<213> ORGANISM: Artificial Sequence
<220> FEATURE:
<223> OTHER INFORMATION: Synthetic

<400> SEQUENCE: 15
ctggtggagt atttgatagt gtattaacct tatgtgtgac atgttctaat atagtcacat     60
tttcattatt tttattataa ggcctgctga aaatgactga atataaactt gtggtagttg    120
gagctgttgg cgtaggcaag agtgc                                          145

<210> SEQ ID NO 16
<211> LENGTH: 145

```
<212> TYPE: DNA
<213> ORGANISM: Artificial Sequence
<220> FEATURE:
<223> OTHER INFORMATION: Synthetic

<400> SEQUENCE: 16
ctggtggagt atttgatagt gtattaacct tatgtgtgac atgttctaat atagtcacat      60
tttcattatt tttattataa ggcctgctga aaatgactga atataaactt gtggtagttg     120
gagctgctgg cgtaggcaag agtgc                                           145

<210> SEQ ID NO 17
<211> LENGTH: 145
<212> TYPE: DNA
<213> ORGANISM: Artificial Sequence
<220> FEATURE:
<223> OTHER INFORMATION: Synthetic

<400> SEQUENCE: 17
ctggtggagt atttgatagt gtattaacct tatgtgtgac atgttctaat atagtcacat      60
tttcattatt tttattataa ggcctgctga aaatgactga atataaactt gtggtagttg     120
gagctagtgg cgtaggcaag agtgc                                           145

<210> SEQ ID NO 18
<211> LENGTH: 145
<212> TYPE: DNA
<213> ORGANISM: Artificial Sequence
<220> FEATURE:
<223> OTHER INFORMATION: Synthetic

<400> SEQUENCE: 18
ctggtggagt atttgatagt gtattaacct tatgtgtgac atgttctaat atagtcacat      60
tttcattatt tttattataa ggcctgctga aaatgactga atataaactt gtggtagttg     120
gagcttgtgg cgtaggcaag agtgc                                           145

<210> SEQ ID NO 19
<211> LENGTH: 145
<212> TYPE: DNA
<213> ORGANISM: Artificial Sequence
<220> FEATURE:
<223> OTHER INFORMATION: Synthetic

<400> SEQUENCE: 19
ctggtggagt atttgatagt gtattaacct tatgtgtgac atgttctaat atagtcacat      60
tttcattatt tttattataa ggcctgctga aaatgactga atataaactt gtggtagttg     120
gagctcgtgg cgtaggcaag agtgc                                           145

<210> SEQ ID NO 20
<211> LENGTH: 16
<212> TYPE: DNA
<213> ORGANISM: Artificial Sequence
<220> FEATURE:
<223> OTHER INFORMATION: Synthetic

<400> SEQUENCE: 20
gtggagtatt tgatac                                                      16

<210> SEQ ID NO 21
<211> LENGTH: 37
<212> TYPE: DNA
<213> ORGANISM: Artificial Sequence
<220> FEATURE:
```

<223> OTHER INFORMATION: Synthetic

<400> SEQUENCE: 21
aaaactacca caagtttata ttcagtcatt ttcagtt        37

<210> SEQ ID NO 22
<211> LENGTH: 16
<212> TYPE: DNA
<213> ORGANISM: Artificial Sequence
<220> FEATURE:
<223> OTHER INFORMATION: Synthetic

<400> SEQUENCE: 22
gtggagtatt tgataa        16

<210> SEQ ID NO 23
<211> LENGTH: 16
<212> TYPE: DNA
<213> ORGANISM: Artificial Sequence
<220> FEATURE:
<223> OTHER INFORMATION: Synthetic

<400> SEQUENCE: 23
gtggagtatt tgatat        16

<210> SEQ ID NO 24
<211> LENGTH: 16
<212> TYPE: DNA
<213> ORGANISM: Artificial Sequence
<220> FEATURE:
<223> OTHER INFORMATION: Synthetic

<400> SEQUENCE: 24
gtggagtatt tgattg        16

<210> SEQ ID NO 25
<211> LENGTH: 16
<212> TYPE: DNA
<213> ORGANISM: Artificial Sequence
<220> FEATURE:
<223> OTHER INFORMATION: Synthetic

<400> SEQUENCE: 25
gtggagtatt tgatcg        16

<210> SEQ ID NO 26
<211> LENGTH: 16
<212> TYPE: DNA
<213> ORGANISM: Artificial Sequence
<220> FEATURE:
<223> OTHER INFORMATION: Synthetic

<400> SEQUENCE: 26
gtggagtatt tgaaag        16

<210> SEQ ID NO 27
<211> LENGTH: 16
<212> TYPE: DNA
<213> ORGANISM: Artificial Sequence
<220> FEATURE:
<223> OTHER INFORMATION: Synthetic

<400> SEQUENCE: 27
gtggagtatt tgagag        16

```
<210> SEQ ID NO 28
<211> LENGTH: 14
<212> TYPE: DNA
<213> ORGANISM: Artificial Sequence
<220> FEATURE:
<223> OTHER INFORMATION: Synthetic

<400> SEQUENCE: 28
cactcttgcc tacg                                                          14

<210> SEQ ID NO 29
<211> LENGTH: 29
<212> TYPE: DNA
<213> ORGANISM: Artificial Sequence
<220> FEATURE:
<223> OTHER INFORMATION: Synthetic

<400> SEQUENCE: 29
agcggcacca cgctccactc ttgcctacg                                          29

<210> SEQ ID NO 30
<211> LENGTH: 31
<212> TYPE: DNA
<213> ORGANISM: Artificial Sequence
<220> FEATURE:
<223> OTHER INFORMATION: Synthetic

<400> SEQUENCE: 30
ctcaccttcc atcaccacga gtatttgata g                                       31
```

DETECTING NUCLEIC ACID VARIATIONS WITHIN POPULATIONS OF GENOMES

CROSS-REFERENCE TO RELATED APPLICATIONS

The present application claims priority to U.S. Provisional Patent Application Ser. No. 61/419,639, filed Dec. 3, 2010, which is incorporated by reference in its entirety.

FIELD OF THE INVENTION

This invention relates to amplification and detection of a rare variant or variants of a DNA sequence in an abundant variant of the sequence, such as detection of a low-level somatic mutations and minority alleles in an excess of normal nucleic acid target sequences.

BACKGROUND

It is sometimes desired to detect a rare variant or multiple rare variants of a DNA sequence in an abundant variant of that sequence. Rare variants are often mutations of a normal gene sequence, which is sometimes referred to as a "wild-type" sequence. Mutations, including particularly rare mutations, are commonly found in cancer-related genes, mitochondrial genes at a low heteroplasmic frequency, and genes from a small subpopulation of bacteria or viruses. Mutant alleles may have only a single change in the DNA sequence (e.g., a point mutation), and frequently they exist in very low abundance in samples containing a corresponding very abundant sequence. Detection of those rare mutations associated with diseases plays an increasingly important role for disease diagnosis and prognosis in clinical practice. For example, point mutations in tuberculosis (TB) can generate drug resistance, making it difficult to select the right drug to use and prolonging treatment. Somatic mutations are useful biomarkers for the early detection of cancer or a prediction of the response or resistance to certain oncology drugs. Mutation in codons 12 and 13 of the KRAS gene occurs in 80-90% of pancreatic cancer and 35-50% of colorectal cancer. And mutations in the EGFR gene or the KRAS gene have been associated with the response or resistance to certain oncology drugs. Recently, the American Society of Clinical Oncology (ASCO) and National Comprehensive Cancer Network has updated its guidelines with a recommendation that therapies including panitumumab or cetuximab be limited to patients with wild-type KRAS for patients with advanced or metastatic colon or rectal cancer. Furthermore, due to the difficulty in accessing to the tumor region, there is an increased requirement to get the tumor cells from blood. Sensitive assays to detect rare mutations in the huge background of wild type allele are critically needed.

Numerous approaches have been developed in the attempt to detect somatic DNA mutations and minority alleles by real-time PCR (polymerase chain reaction) methods. These approaches, many of which are reviewed in Milbury, C. A. et al., PCR-Based Methods for Enrichment of Minority Alleles and mutations (2009) Clin. Chem. 55, pages 632-640, include allele-specific competitive blocker PCR, blocker-PCR, real-time genotyping with locked nucleic acids (LNA) or peptide nucleic acid (PNA), clamp PCR, and restriction enzymes in conjunction with real-time PCR, and allele-specific kinetic PCR in conjunction with modified polymerases. Additional methods include ARMS-PCR, TaqMAMA, and FLAG-PCR. Methods utilizing many of these approaches require either the use of modified bases, special enzymes, or additional proprietary reagents or procedures. In addition, most use a primer that is matched (that is, fully complementary) to a certain mutant sequence and mismatched to the corresponding wild-type sequence, the intent being to amplify only the mutant sequence such that the final amplification product would all be essentially only the mutant-type sequence. In methods that hybridize a primer to a mutation point, mismatches are erased during amplification. PNA or LNA clamp PCR do not rely on a mutant-specific primer, but the manufacture of PNA or LNA oligonucleotides is expensive compared to the manufacture of DNA oligonucleotides. Also, to determine whether a negative result means that a sample contains no mutant or whether there was a failure of amplification, a parallel sample without the PNA or LNA must be run. Existing approaches have proven to be less than satisfactory due to expense, high lower limit of detection, or both. A significant problem with existing selective-amplification assays is the occurrence of false positives caused by errors committed by Taq DNA polymerase. One way to decrease the error rate is to use a high fidelity polymerase such as Pfu or High Fidelity Taq. However, PCR amplification with such enzymes is less efficient, and the optimization of PCR conditions for those high-fidelity polymerases is quite difficult.

A PCR amplification method that preferentially amplifies mutant alleles but does not require an enzyme other than Taq DNA polymerase and provides an amplification product that can be sequenced is COLD-PCR (see Milbury et al., supra). COLD-PCR utilizes a precisely controlled PCR denaturation temperature, for example, 86.5° C., to preferentially denature duplexes, which may be heteroduplexes, containing mutant extension products and thereby preferentially amplify mutant sequences. Disadvantages of this method include a need for very precise temperature control, experimental fine tuning of the denaturation temperature, and variability from mutation to mutation (id). COLD-PCR also does not address the problem of false positives caused by errors committed by Taq DNA polymerase.

SUMMARY

An aspect of this invention is primer-dependent amplification methods for amplifying and detecting rare variants of a DNA sequence in an abundance of another variant of the sequence, such as detecting mutant sequences, particularly rare mutants, in an otherwise normal population of the sequence, utilizing a pair of amplification primers that hybridize to both the rare and abundant sequences, thereby not erasing mutations during amplification, and an inexpensive, non-extendable primer-blocking hairpin oligonucleotide (blocker) comprised of conventional nucleotides (DNA, RNA and DNA/RNA, with only conventional base substitutions such as inosine), wherein the binding site of the blocker includes the allelic variation in question and overlaps the binding site of one of the primers, which is referred to as the first primer and which in non-symmetric methods is the limiting primer; wherein the blocker is perfectly complementary to the abundant target sequence variant and has a Tm against the abundant sequence variant that is at least 3° C., preferably at least 5° C., and more preferably at least 7° C. higher than its Tm against the rare sequence variant; wherein the blocker has a Tm that is higher than the Tm of the first primer by at least 3° C., preferably at least 5° C.; wherein the blocker hybridizes more slowly, preferably by a factor of at least 5, than do the primers; and wherein the amplification method comprises a thermal cycling protocol that includes a blocker-binding step before primer annealing at a temperature at which the blocker hybridizes to the abundant variant but the first primer does not, and a primer-annealing step that is sufficiently short for the primers to hybridize but insufficiently long for the blocker to hybridize to the rare sequence variant. Suitable primer-dependent exponential amplification methods include polymerase chain reaction (PCR) methods, particularly non-symmetric PCR methods, and most preferably LATE-PCR methods.

Another aspect of this invention is any of the foregoing methods that include detection, including but not limited to homogeneous detection, of double-stranded amplification products, single-stranded amplification products, or both. In certain embodiments the primer-blocking hairpin oligonucleotide is labeled so that its hybridization to the target sequence can be detected, preferably by fluorescence detection. Certain preferred labeled blockers have a 3' terminal quencher, such as Dabcyl or a Black Hole quencher. Of these preferred blockers, some have in addition a 5' terminal fluorophore, that is, they are molecular beacon probes.

Another aspect of this invention is primer-dependent, mutant-enriching amplification methods that suppress amplification of abundant wild-type, particularly non-symmetric PCR methods, that include the use of a mismatched second primer as the other amplification primer (in non-symmetric PCR methods, the excess primer), wherein multiple cycles of linear amplification utilizing the first primer are first performed, followed by multiple cycles of exponential amplification utilizing both primers. In the case of non-symmetric PCR, the multiple cycles of exponential amplification are then followed by multiple cycles of linear amplification utilizing the second (excess) primer.

Another aspect of this invention is methods that include both use of a primer-blocking hairpin oligonucleotide and use of at least one modified primer, including a mismatched second primer and including at least one tailed primer, to reduce the effect of polymerase errors.

Other aspects of this invention include oligonucleotide sets of primers and blocker for performing the foregoing methods, and reagent kits including such oligonucleotide sets and amplification reagents, optionally also containing one or more detection reagents, for example, DNA binding dye and fluorescently labeled hybridization probes.

Methods according to this invention are primer-dependent DNA amplification methods, preferably PCR methods, for preferentially amplifying a rare second variant or variants of a DNA target sequence in the presence of an abundant first variant of that DNA target sequence that differs by at least one base change to produce amplified product that is enriched in amplicons of the second variant or variants, which may be detected or sequenced. The primers are linear primers with or without 5' tails. Linear primers may be single-Tm primers because they are complementary to the target at the outset, or they may be double-Tm primers because only the 3' head is complementary to the target initially. Flip-tail primers are a special class of double-Tm primers because they include a temperature-dependent hairpin structure. The design options of such primers are quite flexible but include the following four elements, listed in the 3' to 5' direction: 1) a 3' linear "head" section which functions as the first primer or the second primer during the initial thermal cycle in which that section binds to its complementary target; 2) a "non-complementary neck" section which connects the 3' linear head section to the remainder of the primer; 3) a stem-loop body section comprised of the 5' end of the primer folded on itself; 4) an optional 5' extension that extends beyond the stem and may or may not be labeled.

Preferred amplification methods are non-symmetric thermal-cycling methods such as non-symmetric PCR methods that utilize a limiting primer and an excess primer, where the ratio of excess primer to limiting primer is at least 5:1 and where at the start of amplification the concentration-adjusted Tm of the limiting primer (in the case of a double-Tm primer as the limiting primer, the initial concentration-adjusted Tm of the 3' linear portion) is at least equal to the concentration-adjusted Tm of the excess primer (in the case of a double-Tm primer as the excess primer, the initial concentration-adjusted Tm of the 3' linear portion). Certain methods according to this invention include amplification and homogeneous detection of amplification products or second-variant amplicons in a single reaction vessel (for example, a microcentrifuge tube) in real time during amplification or by end-point detection following amplification, which may include melt analysis or annealing analysis. Methods according to this invention utilize a pair of primers that will amplify both the first variant and one or more second variants of a target sequence, for example, a mutant sequence and a wild-type sequence, if present in the sample.

In certain methods of this invention selective discrimination against amplification of the first variant of a target sequence includes the use of a non-extendable primer-blocking hairpin oligonucleotide (which is sometimes herein refer to as the blocker, for short). The primer-blocking oligonucleotide has a sugar-phosphate backbone. It may be DNA, RNA, or a combination of DNA and RNA. It may include non-natural bases such as inosine. The primer-blocking oligonucleotide is rendered non-extendable by DNA polymerases by modification of its 3' terminus, such as by adding a $C_3$ group or by inclusion of a fluorophore or a quencher. A primer-blocking hairpin oligonucleotide for use in methods of this invention also meets the following criteria: its binding site on the target sequence contains the nucleotide or nucleotides that are subject to the mutation in question and differ between the first target sequence variant, to which its target-binding sequence is perfectly complementary, and the second target sequence variant, to which its target-binding sequence is less than perfectly complementary; its binding site on the target sequence overlaps the binding site of one of the primers, the first primer, by at least one nucleotide; its Tm versus the first variant of the target sequence (the variant to be discriminated against) is sufficiently high to permit a lengthy step in the thermal-cycling protocol, a blocker-binding step, for hybridizing it to the first variant without hybridizing the primers to the target sequence and without hybridizing the primer-blocking hairpin oligonucleotide to the second variant or variants of the target sequence (the variant or variants to be enriched); and its rate of binding to the second variant or variants of the target sequence is markedly slower than the rate of binding of the primers, particularly the first primer, to the target sequence, generally at least five times slower. To permit such a blocker-binding step, the Tm of the primer-blocking hairpin oligonucleotide should be at least 3° C. higher than the Tm of either primer, preferably at least 5° C. higher, and the Tm of the primer-blocking oligonucleotide versus the first variant of the target sequence should similarly be at least 3° C. higher than its Tm against the second variant, preferably at least 5° C. higher and more preferably at least 7° C. higher, in order that it does not hybridize to the second variant during the lengthy blocker-binding step. In non-symmetric methods such as LATE-PCR the first primer is the limiting primer. In the case of linear-tailed or flip-tailed primers the above Tm/temperature relationships refer to the 3'head of each primer which forms the initial primer target hybrids Selective discrimination against amplification of the first variant of a target sequence with consequent enrichment of amplification products in amplicons of the second variant of the target sequence also includes a special amplification protocol for one or more thermal cycles that takes advantage of the properties of the primer-blocking hairpin oligonucleotide to selectively discriminate against amplification of the first variant of the target sequence. Amplification methods according to this invention include a step in the thermal-cycling protocol following strand melting and before primer annealing that is called a "blocker-binding step." The blocker-binding step is at a temperature that is near or below the Tm of the primer-blocking hairpin oligonucleotide against the first variant of the target sequence, which is above the Tm of the primers, particularly the first primer, and the Tm of the primer-blocking hairpin oligonucleotide against the second variant of the target sequence, and that is of sufficient duration for the primer-blocking hairpin oligonucleotide to saturate the first variant of the target sequence. (Because the reagents are subject to thermodynamic equilibrium, "saturate" does not mean that every first-variant strand is hybridized to blocker at a given time. In this description the term "saturate" is used in the practical sense that amplification starting with 10,000 copies of the first sequence does not produce a SYBR signal, as shown in FIG. 9; that is, no detectable product is generated when amplification starts with 10,000 copies of the first variant that do not change during the reaction.) During the blocker-binding step the only hybrid formed is the hybrid comprising the primer-blocking hairpin oligonucleotide and the first variant of the target sequence. The primer-annealing step then follows at a lower temperature at which the primers, at least the first primer (either in its entirety or through its 3' linear portion, as explained above), hybridize to the target sequence, but the duration of this step is sufficiently short so as to permit hybridization of the first primer to the target sequence but to prevent the primer-blocking hairpin oligonucleotide from binding to the second variant or variants of the target sequence, such that extension of the first primer using the second variant or variants of the target sequence as a template is not blocked, but extension of the first primer using the first variant of the target sequence is blocked. Depending upon the degree of enrichment that is required, the extra step of hybridizing the blocker to the first sequence variant may be included in all cycles of amplification, or it may not need to be included in one or more thermal cycles of amplification. The use of a primer-blocking hairpin oligonucleotide in combination with such a temperature cycle results in amplification products substantially enriched in amplicons of the second target-sequence variant or variants relative to amplicons of the first target-sequence variant.

Methods of this invention may include homogeneous detection of amplification product or products. For this purpose at least one detection reagent is included in the original amplification reaction mixture. Such methods may utilize a DNA dye, for example SYBR Green dye, to detect double-stranded amplification products. Methods according to this invention may utilize labeled probes, for example, fluorescently labeled TaqMan probes, side-by-side FRET probes, Lights-On/Lights-Off probes, molecular beacon probes or Scorpion primers, to detect certain amplicon sequences. Methods according to this invention may utilize fluorescently labeled primers, such as Amplifluor primers, to detect amplicons containing incorporated primers. In addition to, or as an alternative to, such homogeneous detection methods, methods according to this invention may utilize primer-blocking hairpin oligonucleotides as all or a portion of a detection means. Examples 1-3 demonstrate the use of primer-blocking hairpin oligonucleotides that are a molecular beacons labeled on one end with a fluorophore and on the other end with a Dabcyl non-fluorescent quencher, wherein the blocker signals upon hybridization to each variant of the target sequence. Alternately, the blocker may be function as one probe of a Lights-On/Lights-Off probe pair. Examples 4-6 demonstrate the use of a hairpin oligonucleotide blocker labeled at its 3' terminus with a Black Hole non-fluorescent quencher that functions as an Off probe, in combination with a fluorophore-quencher labeled molecular beacon that functions as the On probe. Methods according to this invention may use real-time detection or end-point detection, including post-amplification melt (or annealing) analysis.

Selective enrichment of a variant or variants is subject to mistakes made by the DNA polymerase during amplification. For example, Taq DNA polymerase is known to introduce errors during primer extension. The reported error rate of Taq DNA polymerase on different templates varies from $2 \times 10^{-4}$ to $1 \times 10^{-5}$ errors per nucleotide. If, for example, a starting sample at the beginning of amplification contains an initial concentration of 10,000 copies of the first variant of a target sequence, and if the blocker-binding site is 20 nucleotides in length, Taq would introduce 2-40 errors in the blocker-binding site in the first amplification cycle. Such errors often are deleterious to the assay. To address this problem, certain embodiments of methods of this invention utilize a mismatched second primer that has a low Tm and several initial cycles of amplification with a primer-annealing temperature sufficiently high that the second primer is not hybridized and extended, whereby the second variant or variants of the target sequence are copied linearly by extension of the first primer before exponential amplification is begun. Other embodiments of methods of this invention utilize a high fidelity DNA polymerase. Yet other embodiments of methods of this invention utilize a pair of double-Tm linear primers with tails, that may be flip-tail primers, in combination with a blocker. For embodiments of this last type, our strategy is to include in a PCR protocol one or more initial thermal cycles that include a blocker-binding step (as more fully described below, a temperature and time for blocker binding prior to primer binding) to form products that include the tailed primers, followed by multiple thermal cycles that do not include a blocker-binding step, but that include a primer annealing temperature sufficiently high for primer annealing and extension only on all strands that have incorporated linear primers with 5' linear or flip tails.

This invention includes products that comprise oligonucleotides for performing the foregoing methods. Sets of oligonucleotides include at least primers and a primer-blocking hairpin oligonucleotide, and may additionally include a probe that fluoresces upon hybridization, which may be an On probe where the primer-blocking hairpin oligonucleotide is an Off probe. Products of this invention also include amplification kits that include, in addition to such a set of oligonucleotides, amplification reagents that include at least buffer, DNTPs and a thermostable DNA polymerase, and may additionally include a DNA dye, for example, SYBR Green dye.

Definitions

As used herein "sample" can be any material to be tested, such as, for example, a biological or environmental sample. Biological samples can be obtained from any organism. In one embodiment, a sample can be obtained from a mammal, such as a human, companion animal, or livestock and can be a small piece of tissue, including a tissue biopsy. A sample can also be obtained from other animals, such as, for example, a bird. In one embodiment, a sample from an animal comprises a nasopharyngeal aspirate, blood, saliva, feces, urine, or any other bodily fluid. In another embodiment, an environmental sample can be obtained from any environment, such as, for example, soil, water, environments and surfaces in man-made structures.

As used herein "amplification target sequence," "target sequence", DNA target sequence", and "nucleic acid target sequence" interchangeably mean a DNA sequence that provides a template for copying by an amplification reaction and that includes the nucleotide or nucleotides that differ between the first, or abundant, variant and at least one second, or rare, variant. In a double-stranded DNA target sequence, the strand to which the primer-blocking hairpin oligonucleotide binds is referred to as the "first" strand, and the primer that binds to that strand is referred to as the "first" primer. The other strand is referred to as the "complementary" strand or "second" strand, and the primer that binds to that strand is referred to as the "second" primer. An amplification target sequence is typically bracketed in length by a pair of primers used in its amplification. An extension product of either or both primers is an amplification product, or "amplicon". Double-stranded amplicons and, in the case of non-symmetric amplification, single-stranded amplicons have a length defined by the primer pair.

As used herein, "linear primer" means a primer whose target-binding sequence is linear, not structured such as a hairpin whose single-stranded loop is complementary to the target and participates in initial binding to the target, as disclosed in Tyagi et al. European Patent No. 1 185 546. A linear primer may be simply a random-coil oligonucleotide in its entirety. Alternatively, it may have additionally a structured 5' extension for signaling, for example, a Scorpion primer or an Amplifluor primer. It may also have a 5'extension, a tail, that is not complementary to the target and is not used for signaling, but is used to increase the length of the sequence generated by extension of that primer. When the longer sequence is copied in the next thermal cycle, the product is complementary to the entire primer, and hence the primer's Tm increases significantly from its Tm in the first thermal cycle. The 5' tail of such a primer may be a linear, unstructured extension, in which case the primer is referred to as a "linear tail" primer. Alternatively, the extension may fold on itself to form a stem-loop structure which opens and closes as a function of temperature, in which case the primer is referred to herein as a "flip-tail" primer.

The design of linear DNA oligonucleotide amplification primers is generally accomplished with the aid of a computer program designed for that purpose. Among the available programs that can be utilized are PRIDE (Haas et al., Nucl. Acids Res. 26:3006-3012 1998); OLIGO (Rychlik et al., Nucl. Acids Res 17(21):8543-51 1989); OSP (Hilber et al., OSP: a computer program for choosing PCR and DNA sequencing primers. PCR Methods Appl. 1(2):124-128 1991); Primo (Li et al., Genomics 40(3):476-85 1997); and Primer Master (Proutski et al., Comput Appl Biosci 12(3):253-5 1996), and Visual OMP (version 6.1.9) software from DNA Software (Ann Arbor, Mich.).

As used herein "primer-dependent" amplification means a method for amplifying a DNA target sequence exponentially by repeated hybridization of first and second DNA primers (often referred to in the art as forward and reverse primers) to the two strands of a DNA target sequence and extension of the primers by a DNA polymerase using the target sequence strands as templates. Well-known methods for exponential amplification include the polymerase chain reaction (PCR), strand displacement amplification (SDA), nucleic acid sequence based amplification (NASBA), transcription-mediated amplification (TMA), and rolling circle amplification (RCA). Certain of these primer-dependent amplification methods, such as PCR methods, include thermal cycling, while others, such as NASBA, are isothermal. Among numerous DNA polymerases commonly used are *Thermus aquaticus* DNA polymerase (Taq polymerase) and reverse transcriptase.

As used herein, "non-symmetric" DNA amplification means an exponential amplification method that employs one primer in a limiting amount, or concentration, so that it runs out during the amplification process, which continues arithmetically using the remaining, excess, primer. The ratio of excess primer to limiting primer is generally at least 5:1, often higher, for example, 10:1 or 20:1. Non-symmetric DNA amplification produces, first, double-stranded amplification product and then, following exhaustion of the limiting primer, single-stranded amplification product ("amplicon"). Asymmetric PCR and LATE-PCR are non-symmetric PCR methods.

As used herein, "LATE-PCR" means a non-symmetric DNA amplification employing the polymerase chain reaction (PCR) process utilizing one oligonucleotide primer (the "Excess Primer") in at least five-fold excess with respect to the other primer (the "Limiting Primer"), which itself is utilized at low concentration, up to 200 nM, wherein the concentration-adjusted melting temperature of the Limiting Primer at the start of amplification is at least equal to the concentration-adjusted melting temperature of the Excess Primer at the start of amplification, preferably 3-10° C. higher; and wherein thermal cycling is continued for multiple cycles after exhaustion of the Limiting Primer to produce single-stranded product, namely, the extension product of the Excess Primer, sometimes referred to as the "Excess Primer Strand." In certain preferred embodiments, the melting temperature of the amplification product is not more than 25° C. higher than the concentration-adjusted melting temperature of the Excess Primer.

Melting temperature, or "Tm", refers to the temperature at which half of a subject nucleic acid material exists in double-stranded form and the remainder is single stranded. Historically, the Tm of a primer (the primer-target duplex), probe (the probe-target duplex) or amplicon (double-stranded amplification product) is a calculated value using either the "% GC" method (Wetmar, J. G. (1991) "DNA Probes: Applications of the Principles of Nucleic Acid Hybridization," Crit. Rev. Biochem. Mol. Biol. 26:227-259) or the "2(A+T) plus 4(G+C)" method, both of which are well known, at a standard condition of primer concentration and salt concentration. In this application, however, Tm of a primer, primer-blocking hairpin oligonucleotide or probe used in non-symmetric amplification methods means the actual Tm in the amplification reaction mixture at the start of amplification, taking into account its actual concentration, as is done for LATE-PCR. LATE-PCR takes into account the actual primer and probe starting concentrations in determining Tm (Sanchez et al. (2004) PNAS (USA) 101:1933-1938, and Pierce et al. (2005) PNAS (USA) 102: 8609-8614) where possible by using a "nearest neighbor" method (Santa Lucia, J. (1998) PNAS (USA) 95:1460-1465), calculating the Tm using the formula, $Tm=\Delta H/(\Delta S+R \ln (C/2))+12.5 \log [M]-273.15$ (Le Novere, N. (2001), "MELTING, Computing the Melting Temperature of Nucleic Acid Duplex," Bioinformatics 17: 1226-7). $\Delta H$ is the enthalpy and $\Delta S$ is the entropy (both $\Delta H$ and $\Delta S$ calculations are based on Allawi, H. T. and Santa Lucia, J. (1997) Biochem. 36:10581-10594), C is the concentration of the oligonucleotide, R is the universal gas constant, and [M] is the molar concentration of monovalent cations (0.07 in the examples shown). According to this formula the nucleotide base composition of the oligonucleotide (contained in the terms ΔH and ΔS), the monovalent salt concentration, and the concentration of the oligonucleotide (contained in the term C) influence the Tm. However, the concentration of magnesium, a divalent cation used in PCR buffers is not included in this formula. Recent modifications to the above formula include adjustment for the magnesium concentration. Visual OMP (version 6.1.9) software from DNA Software (Ann Arbor, Mich.) includes such an adjustment to the nearest neighbor formula.

For the Tm of a linear primer, one calculates the concentration-adjusted Tm using the Visual OMP software. For the Tm of a linear primer with a 5' linear tail or with a 5' flip tail that is initially not complementary to the target, one may use Visual OMP software to calculate a first concentration-adjusted Tm for the just the 3' complementary portion of the primer, sometimes referred to herein as the head of the primer, that initially binds to the target and a second concentration-adjusted Tm for the entire primer. For a primer-blocking hairpin oligonucleotide or a molecular beacon probe, neither of which is linear, one can use a measured Tm. Certain primer-blocking hairpin oligonucleotides and probes useful in methods of this invention are modified in a way affecting their Tm's by several ° C., such as, for example, with interacting fluorophore and quencher. An interacting fluorophore and quencher increase the Tm of a blunt-ended hybrid. Marras, S. A. E., et al., (2002) Nucleic Acids Research 30 No. 21 e122. For a hairpin blocker or probe, an interacting label pair on the stem will increase the stem strength and thereby lower the Tm of the blocker or probe versus its target by a few ° C. as compared to the same blocker or probe without interacting labels. It is sometimes necessary to consider the Tm of a primer, primer-blocking hairpin oligonucleotide, or probe in hybrids with strands having different sequences. In this application this need is addressed by specifying the strand to which a Tm applies, that is, the Tm of the primer, blocker or probe "with respect to", "against" or "versus" a particular target sequence variant or amplicon. As used herein, "Lights-On/Lights-Off" probes mean fluorescently labeled probe combinations comprising at least one "signaling probe" that signals upon hybridization to a target, preferably a fluorophore-quencher labeled molecular beacon probe, and at least one "quencher probe" that includes a quenching moiety and hybridizes to the target proximate to the signaling probe such that, when only the signaling probe is hybridized, it fluoresces, but, when both probes are hybridized, the quencher of the quencher probe quenches fluorescence of the signaling probe. If the signaling probe is the higher Tm probe, progressively lowering the temperature of the reaction mixture generates an annealing curve: first the signaling probe hybridizes, resulting in signal, and then the quencher probe hybridizes, extinguishing the signal. If the signaling probe has a Tm that is lower than the Tm of the quencher probe, fluorescence does not increase upon binding of the signaling probe adjacent to its quencher probe, but instead fluorescence decreases upon binding of the signaling probe, because the fluorophore/quencher interaction of the adjacent signaling probe and quencher probe bound to the target is more stable than the interaction of the fluorophore and the quencher located on opposite ends of the unbound signaling probe. In certain embodiments, Black Hole quenchers are used in Lights-On/Lights-Off probes. Lights-On/Lights-Off probes are described in patent application PCT/US2010/053569, which is incorporated by reference herein in its entirety. However, as one skilled in the art will appreciate, other quenchers may increase or decrease the optimal probe-to-target Tm.

DETAILED DESCRIPTION

Figure 1:
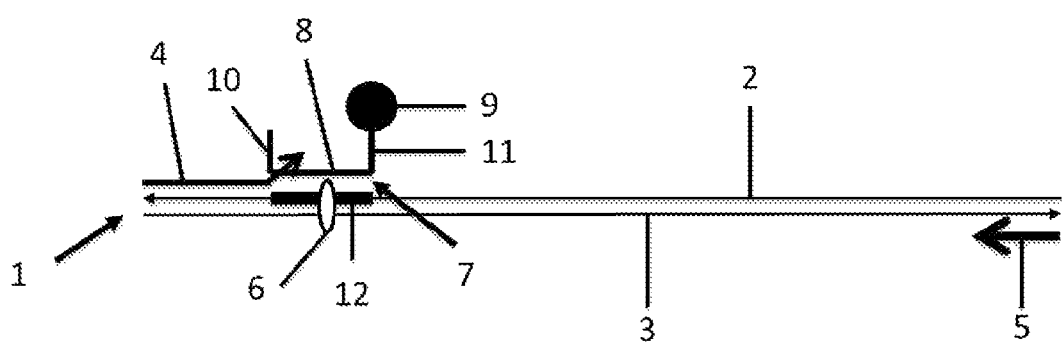
FIG. 1 is a schematic showing the hybridization, or binding, of a primer-blocking hairpin oligonucleotide and amplification primers to a first variant of a target sequence.

Methods according to this invention are primer-dependent exponential DNA amplification methods that include thermal cycling, preferably PCR methods. A primer pair hybridizes to a selected amplification target sequence so as to amplify both an abundant first variant of the target sequence and also a second variant or variants (mutants or rare alleles) of the target sequence. Neither primer is designed to hybridize to the target sequence such that its binding site in the target sequence includes the nucleotide or nucleotides that are different in the first variant and the second variant or variants, which lie between the primer binding sites. Rather, one primer, which is referred to as the "first" primer, is designed to hybridize to the target sequence upstream of the differing nucleotide or nucleotides by from one to twenty nucleotides. Preferred methods are non-symmetric PCR methods, in which case the first primer is the limiting primer. LATE-PCR methods are especially preferred.

Nucleic acid amplification employing PCR is well known. See U.S. Pat. Nos. 4,683,202, 4,683,195 and 4,965,188, and, generally, PCR PROTOCOLS, a guide to Methods and Applications, Innis et al. eds., Academic Press (San Diego, Calif. (USA) 1990). PCR amplification reactions, like other primer-dependent DNA amplification methods, are generally designed to be symmetric, that is, to make double-stranded amplification products (amplicons) by utilizing a forward primer and a reverse primer that are "matched"; that is, they have melting temperatures that are as close as possible, and they are added to the reaction in equimolar concentrations. A non-symmetric PCR method that has found limited use for making single-stranded DNA directly in a PCR reaction is "asymmetric PCR." Gyllensten and Erlich, "Generation of Single-Stranded DNA by the Polymerase Chain Reaction and Its Application to Direct Sequencing of the HLA-DQA Locus," Proc. Natl. Acad. Sci. (USA) 85: 7652-7656 (1988); and U.S. Pat. No. 5,066,584. Asymmetric PCR differs from symmetric PCR in that one of the primers is added in limiting amount, typically 1-20 percent of the concentration of the other primer.

A more recently developed non-symmetric PCR amplification method is known as "Linear-After-The-Exponential" PCR or, for short, "LATE-PCR." See Sanchez et al. (2004) PNAS 101: 1933-1938, Pierce et al. (2005) PNAS 102: 8609-8614, and published international patent application WO 03/054233 (3 Jul. 2003), which is incorporated herein by reference in its entirety. LATE-PCR takes into account the actual, concentration-adjusted melting temperatures of PCR primers at the start of amplification, which is referred to in these references as $Tm_{[0]}$. $Tm_{[0]}$ can be determined empirically, as is necessary when non-natural nucleotides are used, or calculated. In non-symmetric PCR methods of this invention, $Tm_{[0]}$ of the limiting primer is at least equal to $Tm_{[0]}$ of the excess primer, preferably higher by 3-10° C., and the limiting primer is the "first" primer. LATE-PCR also takes into account the actual concentration-adjusted melting temperatures of PCR primers that have an initial $Tm_{[0]}$ for the 3' linear "head" portion of a primer with a 5' tail that does not bind to the target initially. Because the tail subsequently binds to the extended target such primers can be considered to have a second concentration-adjusted melting temperature, hereafter $Tm_{[0']}$.

Homogeneous PCR assays are PCR assays that do not require washing to remove unbound detection reagents, for example, probes, and thus can be performed without opening amplification reaction vessels are also well known. Homogeneous PCR assays include real-time assays, in which amplified product is detected during some or all of the thermal cycles as the reaction proceeds, and end-point detection, in which amplified product is detected after completion of the amplification reaction. End-point detection may include melt analysis in which signal is detected as the temperature of the reaction mixture is heated or cooled. See U.S. Pat. Nos. 5,994,056, 5,487,972, 5,925,517 and 6,150,097. Homogeneous detection may be by a DNA binding dye, for example, a SYBR dye such as SYBR Green or SYBR Gold, that binds preferentially to double-stranded DNA and fluoresces when it binds. Homogeneous detection may be by a labeled hybridization probe whose binding to an amplified target sequence leads to a detectable signal. Preferred probes for use in methods according to this invention are probes that signal upon hybridization, for example, molecular beacon probes.

A blocking oligonucleotide useful in methods according to this invention is a hairpin oligonucleotide comprised of a sugar backbone, for example, DNA, or RNA or a combination of DNA and RNA. It may include non-natural bases such as inosine. A blocking oligonucleotide of this type is inexpensively synthesized by conventional methods. The 3' end of the blocking oligonucleotide is blocked, for example capped, to prevent extension by a DNA polymerase. It may be unlabeled, or it may be labeled, preferably labeled, as discussed above. A blocking oligonucleotide useful in methods of this invention is primer-blocking. Its binding site in the target sequence overlaps the binding site of the first primer by at least one nucleotide. (In several Examples set forth below the binding site of the blocker overlaps the binding site of the first primer by eight nucleotides.) Thus, if the blocker is first hybridized to a variant of the target sequence, the first primer is preventing from binding and extending. Accordingly, blockers useful in methods of this invention are referred to as "primer-blocking hairpin oligonucleotides."

For use in methods of this invention, amplification primers are linear primers designed to bracket the target sequence, so that all variants of the target sequence are amplified. The primers need not be labeled. Alternately, one of the primers may be fluorescently labeled to signal the production of amplicon strands by attaching a fluorophore to the 5' end, which is not complementary to the target sequence (Scorpion primer or Amplifluor primer). In certain embodiments, unlabeled primers are employed. Neither primer has a binding site that includes the nucleotide or nucleotides that differ between or among the target variants. However, one primer, referred to here as the first primer, is designed to have a target-binding site only a few (less than 20) nucleotides upstream from the nucleotides that differ. The primer-blocking hairpin oligonucleotide is designed such that its binding site satisfies two criteria: first, it encompasses the nucleotide or nucleotides that differ between or among target variants; and, second, the 3' end of its binding site in the target sequence overlaps the 5' end of the binding site of the first primer by at least one nucleotide. In methods that include non-symmetric PCR amplification, including LATE-PCR amplification, the first primer is the limiting primer. Further, the target-binding sequence of the primer-blocking hairpin oligonucleotide is made perfectly complementary to the first (abundant) target variant whose amplification is to be blocked. The relationships of the primers and primer-blocking hairpin oligonucleotide to the target sequence and one another are depicted in FIG. 1. That figure depicts a double-stranded target 1 comprised of strand 2,3. The target sequence to be amplified is determined by primers 4,5, which bracket that sequence. The target sequence to be amplified includes a nucleotide 6 that differs between or among target variants. First primer 4 is designed to bind to strand 2 slightly upstream from nucleotide 6. Primer blocking hairpin oligonucleotide 7 includes a target-binding sequence 8 and a 3' blocking moiety 9, rendering it non-extendable by a DNA polymerase such as Taq DNA polymerase. In the embodiment depicted in FIG. 1, blocker 7 includes 5' and 3' terminal regions 10,11 that are not complementary to the target, but it is permitted that at least one end of the blocker be complementary. As shown in FIG. 1, target-binding sequence 8 of blocker 7 is complementary to strand 2 in the region, blocker-binding site 12, that includes nucleotide 6, that is, its binding site includes nucleotide 6. Further, at least one 5' nucleotide of target-binding sequence 8 and one 3' nucleotide of primer 4 compete for hybridization to strand 2; in other words, the binding site of blocker 7 overlaps the binding site of primer 4 by at least one nucleotide. As shown in FIG. 1, blocker 7 is hybridized to strand 2, preventing the 3' terminus of first primer 4 from hybridizing and preventing extension of that primer by a DNA polymerase.

Figure 2:
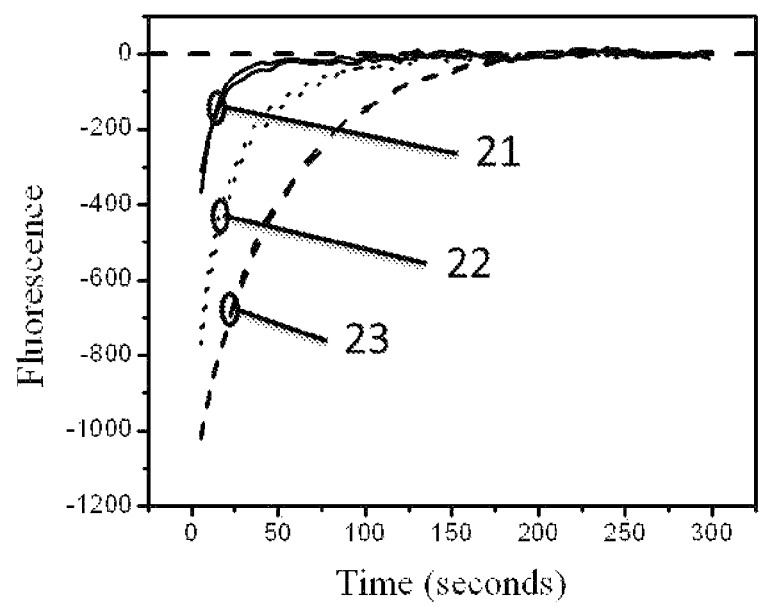
FIG. 2 is a graph showing the hybridization rates of primer-blocking hairpin oligonucleotide candidates having stems of different lengths.

Methods according to this invention utilize the difference in the Tm of the primer-blocking hairpin oligonucleotide with respect to the perfectly complementary variant of the target sequence (which is referred to as the "first" variant) and with respect to any variant whose sequence differs by at least one nucleotide in the binding-site of the blocker (which is referred to as a "second" variant). More importantly, methods according to this invention utilize the slow hybridization rate of a primer-blocking hairpin oligonucleotide relative to the hybridization rate of the first primer, which is generally less than 10 seconds. These properties are illustrated in Example 1 below. The primer-blocking hairpin oligonucleotide is designed, by adjusting the lengths and GC content of its loop and stem, to have a Tm versus a first target sequence variant that is higher than its Tm versus a second target sequence variant by an amount sufficient to have a step in the thermal-cycling protocol at which the primer-blocking hairpin oligonucleotide binds to the first variant but not to the second variant. To that end the Tm versus the first variant exceeds the Tm versus the second variant by at least 3° C., preferably at least 5° C., and more preferably 7° C. or more, for example, 8° C., 9° C. or 10° C. Further, its Tm versus the first variant of the target sequence is at least 3° C. higher, preferably at least 5° C. higher, than the Tm of either primer. The primer-blocking hairpin oligonucleotide is designed to have a rate of hybridization to the target variants that is much slower than the hybridization rate of the primers at hybridization temperatures used in the method, preferably taking at least five times longer to saturate the target than is needed for annealing the first primer. For example, with a 10-second annealing step for the first primer, the blocker hybridization rate should be sufficiently slow to require one minute to saturate the target and optionally longer, for example, 2-3 minutes. Even longer saturation times are less desirable, because they unnecessarily lengthen the total time of the amplification reaction. Example 1 describes analysis of primer-blocking hairpin oligonucleotide candidates containing the same target-binding sequence that is 18 nucleotides long but differing in stem length from one nucleotide (NT) to nine NT. As shown in Table 1, increasing the stem length lowered the Tm against all variants, but the Tm versus the first variant of the target sequence remained about 10° C. higher than the Tm against a second variant differing by one NT in the blocker's binding site. FIG. 2 shows, however, that the rate of binding changes markedly with the length of the stem. Primer-blocking hairpin oligonucleotide BL, which had a stem length of 1 NT, saturated the first variant of the target sequence in about 30 seconds at 60° C. (curves 21). Primer-blocking hairpin oligonucleotide B62, which had a stem length of 5 NT, took about 2 minutes to saturate that variant at the same temperature (curves 22). And primer-blocking hairpin oligonucleotide B71, which had a stem length of 6 NT, took about 3 minutes (curves 23). With a blocker having this particular target-binding sequence, the stems of blockers B62 and B71 were judged to be sufficiently long to impart the desired slow hybridization rate for use generally in methods according to this invention. Short-stem blocker BL, on the other hand, was judged to be acceptable only if an extremely short primer-annealing step were utilized.

As stated above, methods of this invention utilize a primer-blocking hairpin oligonucleotide that hybridizes to the target slowly, but hybridizes to the first variant of the target sequence at a temperature higher than the temperature at which either primer binds. Methods of this invention include the thermal cycling protocol a step following strand melting that is at a temperature at which the blocker hybridizes to the first variant of the target, but at which the primers do not hybridize to the target sequence and the blocker does not hybridize to the second variant or second variants of the target sequence, that step being sufficiently long to permit the blocker to saturate the first variant of the target sequence. That step, which is referred to as the blocker-binding step, is preferably included in all amplification cycles, but it may be omitted in one or more terminal cycles in cases where amplification of the first variant of the target sequence that results from such omission can be tolerated, as can be determined empirically. Methods of this invention include a short primer-annealing step following the blocker-binding step. To permit the primers to anneal, the primer-annealing step is at a lower temperature than the blocker-binding step. At the primer-annealing temperature, the higher Tm primer-blocking hairpin oligonucleotide would out-compete the lower Tm first primer for binding to the second variant of the target sequence at equilibrium. However, the primers are linear oligonucleotides, and hence their rate of hybridizing to the target sequence is much faster than that of the blocker. The primer-annealing step is limited to a time sufficient to for the primers to bind to the target sequence but insufficient for the blocker to bind appreciably to the second variant of the target sequence. Methods of this invention greatly enrich the products of amplification in amplicons of the second variant or variants. Coordinating the Tm of the primer-blocking hairpin oligonucleotide to the variants of the target sequence, the binding kinetics of the blocker to the targets, the Tm's of the primers, and PCR protocol, rare second variants of a target sequence can be selectively amplified in a background of abundant first variant of the target sequence.

Figure 3A:
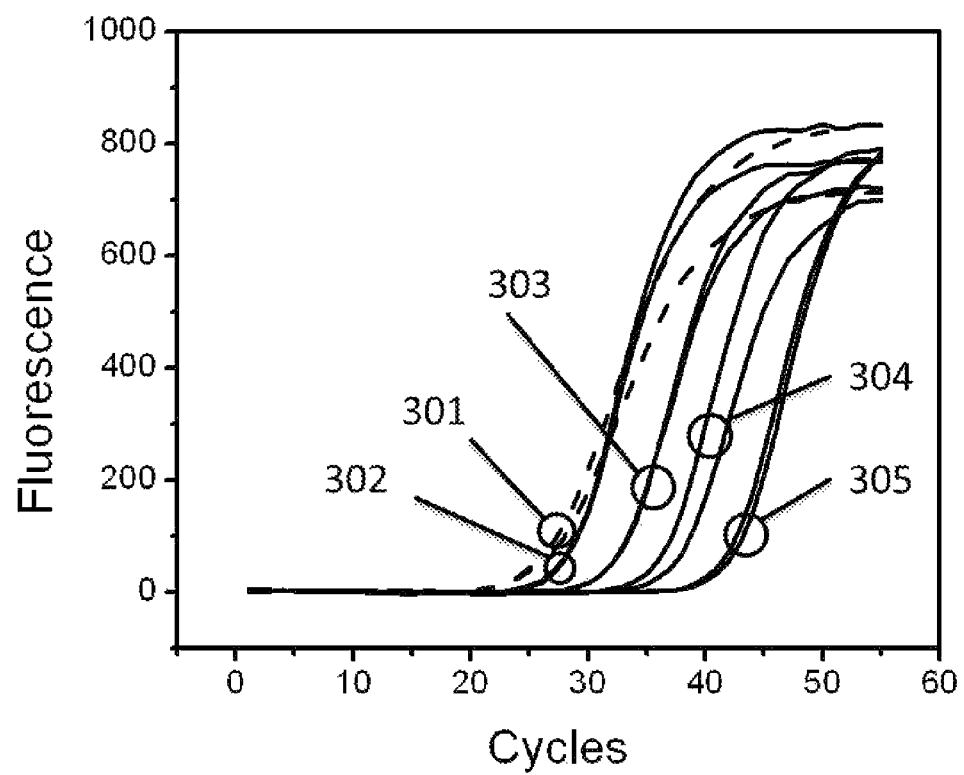
FIGS. 3A-3C are real-time SYBR fluorescence readings during LATE-PCR amplifications described in Example 2 that include blocker B62 and no blocker-binding step (FIG. 3A), a one-minute blocker-binding step (FIG. 3B), or a two-minute blocker-binding step (FIG. 3C).

The effect of the blocker-binding step in the amplification protocol is demonstrated in Example 2 below. A first variant of a target sequence (perfectly complementary to the binding sequence of primer-blocking hairpin oligonucleotide (blocker) B62) and a second variant of the target sequence (one NT mismatch to the binding sequence of blocker B62) were amplified separately in LATE-PCR reactions that included primer-blocking hairpin oligonucleotide B62 (five NT stem) and a primer-annealing step of 10 seconds at 50° C. The first variant was amplified beginning with $10^6$ copies of the target sequence. The second variant was amplified beginning with $10^3$, $10^2$, $10^1$, and $10^0$ copies of the target sequence. Production of double-stranded amplification product was detected in real time using SYBR Green dye. Amplifications were performed with no (0 min) 60° blocker-binding step (FIG. 3A), with a 60° C./1 min blocker-binding step (FIG. 3B), and with a 60° C./2 min blocker-binding step (FIG. 3C). Turning to FIG. 3A, even without the 60° C. blocker-binding step, the blocker inhibited the amplification of said first variant of the target sequence. One million copies of the first variant, curves 301, resulted in a threshold cycle ($C_T$) of 26, which is 2 $C_T$ earlier than 1,000 copies of said second variant, curves 302. One hundred copies of the second variant, curves 303, 10 copies, curves 304, and a single copy of the second variant, curves 305, gave $C_T$ values of 32, 37 and 42 respectively. The amplification curves of the second target sequence variant are parallel to each other, and a single copy comes up reliably, which indicates that the presence of blocker B62 did not inhibit the amplification of the second variant. Amplifications with the same $C_T$ would produce the same amount of final amplification products that would be easily detected by a probe or by sequencing. With the thermal cycling protocol without a blocker-binding step, 1 million copies of the first variant of the target sequence would have the same $C_T$ value as 4,000 copies of the second variant of the target sequence. The sensitivity of the assay, therefore, would be about 4,000 copies of second target sequence variant to 1 million copies of first target sequence variant. The assay is sensitive to a ratio of about one copy of the second variant per 250 copies of the first variant, which is a sensitivity of 1:250. Applying the same analysis to FIG. 3B (1 min blocker-binding step), the sensitivity improves to 1:10,000. Applying the same analysis to FIG. 3C (2 min blocker-binding step), the sensitivity further improves to between 1:10,000 and 1:100,000. It is noted that the foregoing analysis does not account for errors that may have been introduced by the Taq DNA polymerase. If Taq DNA polymerase introduces an error in the binding site of the primer-blocking hairpin oligonucleotide as it copies the first variant of the target sequence, the resulting copy of first target sequence may be a second variant of the target sequence. Such an error may give a false positive signal of the presence of the second variant and significantly reduce the sensitivity of the assay.

Figure 5:
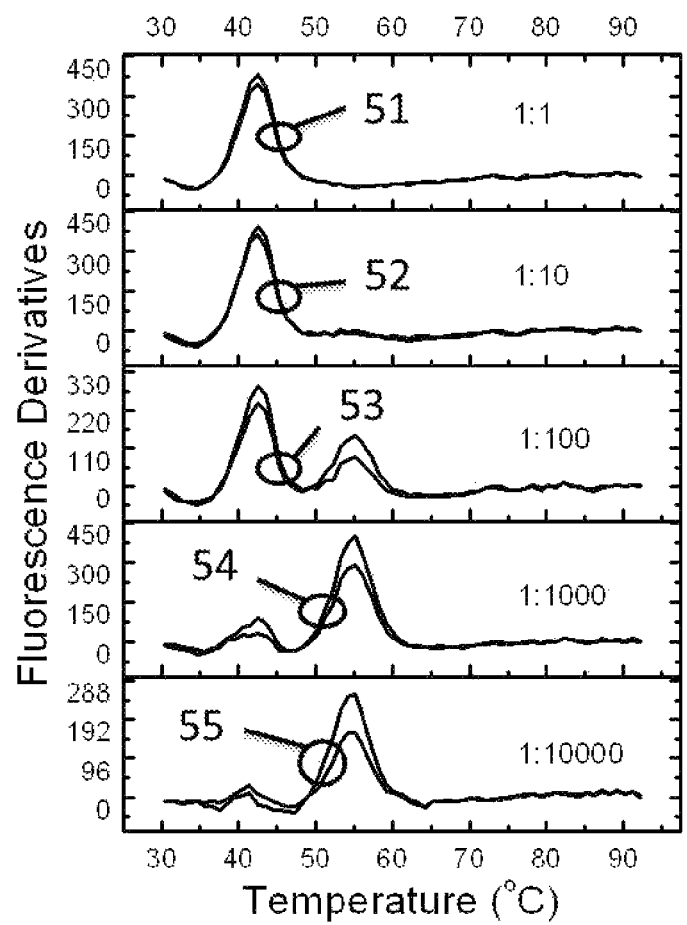
FIG. 5 is a series of graphs containing melting curves (derivative of probe fluorescence versus temperature) following LATE-PCR amplifications described in Example 2 for samples containing mixtures of first and second variants of a target sequence.

The effectiveness of hairpin blocking oligonucleotide in the assay of Example 2 was confirmed by performing the LATE-PCR assay including the 2-minute blocker-binding step on five different reaction mixtures containing 10 copies of the second variant of the target sequence in combination with varying amounts, from 10 to 100,000 copies, of the first variant of the target sequence. Post-amplification melting curves were generated. FIG. 5 presents the melting curves. FIG. 5 shows that the assay was indeed sensitive to a ratio of at least 1:10,000, because the 43° C. melting peak of amplicons of the second variant was detectable when the starting amplification reaction mixture contained 10 copies of the second target sequence variant and 100,000 copies of the first target sequence variant (curves 55). Once again, errors of the Taq DNA polymerase were not accounted for in this analysis, and such errors may significantly adversely affect the sensitivity of the assay.

Figure 6:
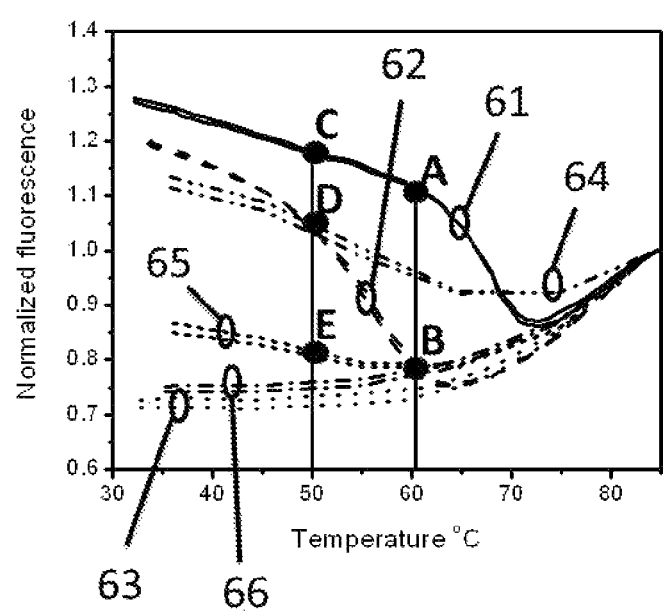
FIG. 6 is a graph of fluorescence versus temperature for hybridizations, described in Example 1, of blocker B62 to first and second target sequence variants at equilibrium and for ten seconds.

The operation of the primer-blocking hairpin oligonucleotide in the experiments of Example 2 can be considered in conjunction with FIG. 6, which plots selected fluorescence readings from the fluorophore of blocker B62 as a function of temperature from blocker hybridization experiments described in Example 1. In FIG. 6, curves 61 are the equilibrium curves for blocker B62 binding to the first variant of the target sequence, and curves 62 are the equilibrium curves for blocker B62 binding to the second variant of the target sequence. As can be seen, at 60° C. there is high signal from the first variant (point A) but basically no signal (equivalent to the no-template control, curves 63) from the second variant (point B). At 50° C., however, there is high signal from the first variant (point C) but also high signal from the second variant (point D). Also in FIG. 6 are curves in which annealing is permitted for only 10 seconds. Curves 64 are the 10-second curves for blocker B62 binding to the first target sequence variant, and curves 65 are the 10-second curves for blocker B62 binding to the second target sequence variant. If the temperature is dropped from 60° C. to 50° C. but maintained there for only 10 seconds, there is a high signal from the first variant (point D) but very little signal from the second target sequence variant (point E, which is only slightly higher than the no-template control, curves 66). Assays according to this invention take advantage of the information in FIG. 6. As shown in FIG. 6, blocker B62 binds to the first variant of the target sequence at a higher temperature than it binds to the second variant of the target sequence. FIG. 6 also shows that at a given temperature, annealing for only a short time (10 sec) results in much less binding to the second target sequence variant than is achieved at equilibrium (2 min). Considering FIG. 6, if a blocker-binding step is inserted into a PCR cycle, that is, if the temperature reduction after strand melting does not proceed directly to 50° C. for primer annealing, but stops at 60° C. for 2 minutes, the first variant of the target sequence will be bound by blocker B62 blocker (point A), while none of second variant will be bound (point B). This results, because the Tm of blocker B62 versus the first variant (67° C.) is sufficiently high to bind to the first variant at 60° C., but the Tm of blocker B62 versus the second variant (57° C.) is not sufficiently high to bind to the second variant. If, with the first target sequence variant thus bound, the temperature is dropped to 50° C. for primer annealing, the first target sequence variant will remain bound by blocker B62. The result is that blocker B62 will prevent the first primer from binding/extending copies of the first variant. If the hybridization rate of blocker B62 were fast, it would be able to bind to the vast majority of copies of the second variant of the target sequence during the 50° C./10 s primer-annealing step (point D). That would suppress amplification, not only of the first variant, but the second variant as well. However, that is not the case. Blocker B62 has slow binding kinetics, that is, a slow hybridization rate due to its stem. Setting the primer-annealing step at 10 seconds prevents blocker B62 binding to the second variant of the target sequence (point E). Because the primers anneal within 10 seconds at 50° C., amplification of the second variant of the target sequence proceeds while amplification of the first variant is greatly suppressed by blocker B62.

FIG. 6 illustrates another feature of methods that utilize a primer-blocking hairpin oligonucleotide. If no signal results from an amplification that includes homogeneous detection, the result could be a negative, that is, the sample contained only first target sequence variant, or the result could be a false negative due to failure of the amplification reaction for some reason such as omitting polymerase from the reaction mixture. Determining which possibility is the fact can be ascertained using the same test sample in the same reaction vessel by simply re-running the thermal cycling protocol without the blocking-binding step. In that case some first primer will out-compete the blocker for binding to the first target sequence variant, and a true negative sample will generate a fluorescent signal from amplification of the first target sequence variant, showing that the amplification reaction worked. FIG. 6 shows that blocker B62 does not saturate the first target-sequence variant at 50° C. in 10 seconds even in the absence of competing first primer, so the blocker will not prevent amplification of the first target sequence variant in the re-run without the blocker-binding step. There is no need to run a separate control sample in which the blocker is omitted.

Figure 7:
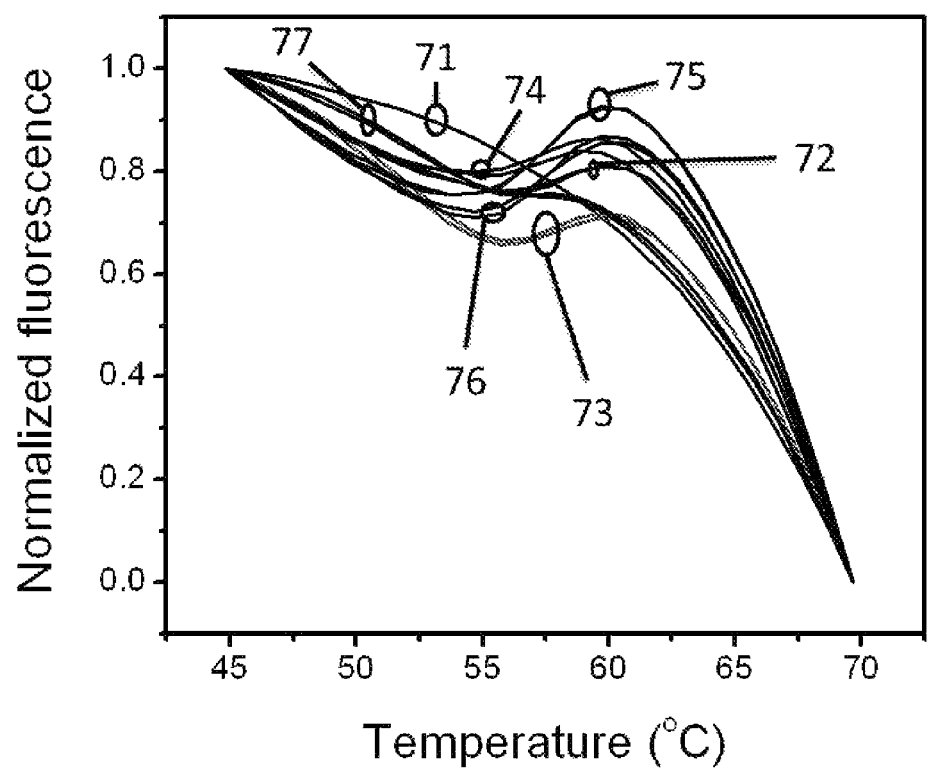
FIG. 7 is a graph of fluorescence from a primer-blocking hairpin oligonucleotide versus temperature during melting following amplification of samples with first target sequence variant or with several different second target sequence variants, as described in Example 3.

The nature of the difference between the sequence of the first variant of the target sequence and the second variant of the target sequence has an effect on the melting curve of the amplified product. In Example 3 below, a variety of different single-NT changes were tested. As shown in FIG. 7, melting curves were different for different changes. This provides information regarding which change is present in a sample.

The primer-blocking hairpin oligonucleotides utilized in Examples 1-3, notably blocker B62, were labeled with a fluorophore and a quencher. Their hybridization to a target sequence resulted in fluorescence from the fluorophore, as discussed above and described in Examples 1-3. Certain preferred embodiments of this invention utilize a primer-blocking hairpin oligonucleotide that has no fluorophore but has at least one quencher and that is part of a Lights-On/Lights-Off probe pair, namely, the Off probe. Such a pair is shown schematically in FIG. 8, where 803 is the blocker's binding region hybridized to strand 810 of target sequence 809, and 805 is a non-fluorescent quencher moiety at the 3' end of the blocker. Hybridized to strand 810 immediately downstream from the blocker is an On probe, where 804 is the probe's binding region, 806 is a fluorophore at the 5' end of the On probe, and 807 is a quencher at the 3' end of the On probe. It will be appreciated that the blocker-Off probe could have additionally a quencher on its 5' end, or even a fluorophore on its 5' end provided the fluorophore were distinguishable from fluorophore 806.

All selective assays face the problem of false positive signals from samples containing only the first variant of the target sequence due to errors introduced by the polymerase, notably Taq DNA polymerase. This is caused by errors made by, for example, Taq DNA polymerase when extending the second primer using the target strands complementary to it (the second strand of both target sequence variants) as templates. Of course, the vast majority of such template strands are contributed by the first variant of the target sequence. If an error occurs under the blocker-binding region when copying a copy of such first-variant strands, that is, in the blocker-binding site, that would create a mutant equivalent to an original copy of the second variant of the target sequence, which would not be blocked during the following amplification cycles. Should that occur early in the amplification reaction, a false positive will result. Certain embodiments of methods of this invention utilize a low-temperature, mismatched second primer (in non-symmetric PCR, the excess primer) in combination with a modified amplification protocol to eliminate or reduce the occurrence of false positives.

Figure 8:
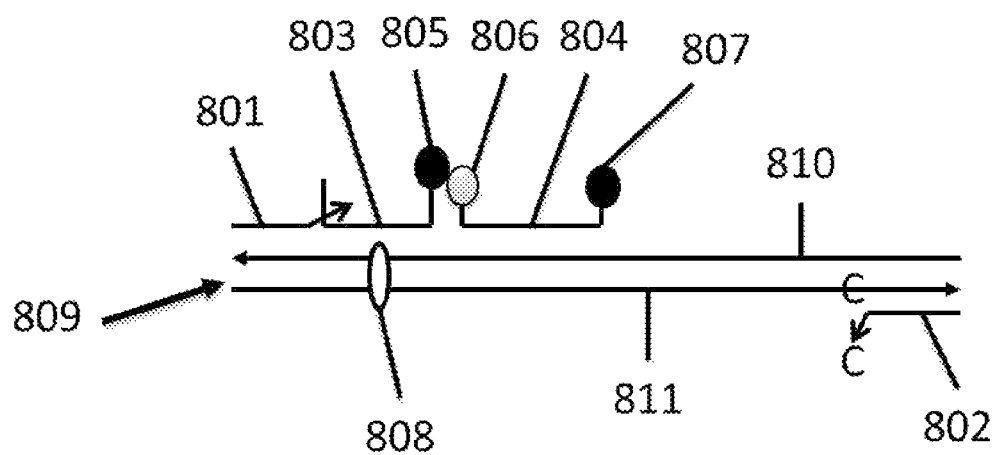
FIG. 8 is a schematic showing the hybridization, or binding, to a first target sequence variant of a primer-blocking hairpin oligonucleotide functioning as an Off probe, an interacting On probe, a first primer and a mismatched second primer.

Certain assays of this invention include use of a mismatched second primer in combination with a modified thermal cycling protocol to address the problem of false positives. A mismatched second primer is shown in FIG. 8, where second primer 802 has a 3' terminal C-C mismatch versus the second target strand 811. A thermal cycling amplification protocol, for example, a PCR protocol, in which amplification of a first target sequence variant is discriminated against is modified for use of a mismatched second primer. The protocol includes several initial cycles having a high annealing temperature. During these cycles the first primer binds to the target sequence and is extended but the mismatched second primer does not bind and extend. Because the amplification method discriminates against the first variant of the target sequence, these cycles of linear amplification enrich the reaction mixture in strands made by copying the first variant. The cycles of linear amplification are followed by one or more cycles, preferably one cycle, having a lower annealing temperature. During this cycle or these cycles both primers bind and are extended. This creates strands containing the second primer. Strands containing the second primer can be amplified exponentially using the higher annealing temperature. The low-temperature cycle or cycles is then followed by cycles in which the annealing temperature is returned to the higher temperature. Amplification methods utilizing a mismatched second primer and modified thermal cycling protocol include generally thermal cycling methods that discriminate against amplification of a first target sequence variant. In certain embodiments, assays that include use of primer-blocking hairpin oligonucleotides as described in this application are employed.

An embodiment of an amplification assay using a mismatched second primer is described in Example 4. That embodiment is a LATE-PCR assay using a primer-blocking hairpin oligonucleotide, which serves as the Off probe of Lights-On/Lights-Off probe pair, and a short-stem molecular beacon On probe, as has been discussed. The mismatched second primer, which in non-symmetric PCR methods is the excess primer, had a 3' terminal C-C mismatch with respect to the target sequence, as depicted in FIG. 8. The thermal cycling protocol included a 60° C./2 min blocker binding step and a 50° C./10 sec primer-annealing step in all cycles except one. For purposes of discussion, these are called "normal" cycles. The protocol starts with multiple normal cycles, preferably at least five. The protocol of Example 4 started with 10 normal cycles, in which the mismatched primer did not participate, the second variant of the target sequence was copied linearly, enriching the reaction mixture in the second sequence variant. Next in the protocol was one cycle that included annealing at 40° C., in which the mismatched excess primer did participate. This created amplicons whose complementary copies would be perfectly complementary to the mismatched excess primer. There followed fifty cycles of LATE-PCR amplification with a primer annealing temperature sufficiently high, 50° C., for the excess primer to bind only to perfectly complementary strands. For comparison the amplification was also performed using a perfectly complementary excess primer.

Figure 9:
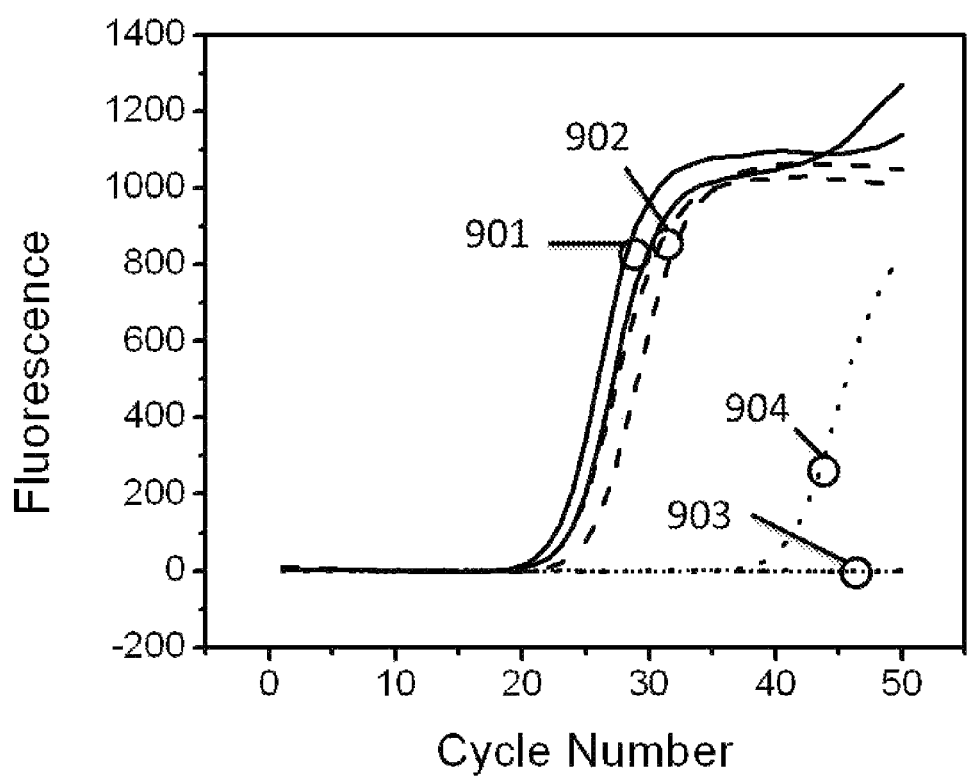
FIG. 9 is real-time SYBR fluorescence readings during LATE-PCR amplifications described in Example 4 using perfectly complementary second primer and mismatched second primer with samples containing either first target sequence variant or second target sequence variant.

FIG. 9 presents real-time SYBR fluorescence curves of amplifications with the modified thermal cycling protocol. Curves 901 are reaction mixtures containing 10,000 copies of the first variant of the target sequence and the perfectly complementary excess primer. Curves 902 are reaction mixtures containing 10 copies of the second variant of the target sequence and the perfectly complementary excess primer. Curves 903 are reaction mixtures containing 10,000 copies of the first variant of the target sequence and the mismatched excess primer. And curves 904 are reaction mixtures containing 10 copies of the second variant of the target sequence and the mismatched excess primer. Comparing curves 901 and 902, one sees that using the perfectly complementary excess primer, 10,000 copies of the first target sequence variant produced as much amplified product as did 10 copies of the second target sequence variant—their $C_T$'s are about the same. Comparing cures 903 and 904, however, one sees that using the mismatched excess primer, 10,000 copies of the first variant did not produce as much amplified product as did 10 copies of the second variant—their $C_T$'s were not the same. In fact, 10,000 copies of the first variant of the target sequence with the mismatched excess primer (curves 903) produced no detectable signal.

Figure 10:
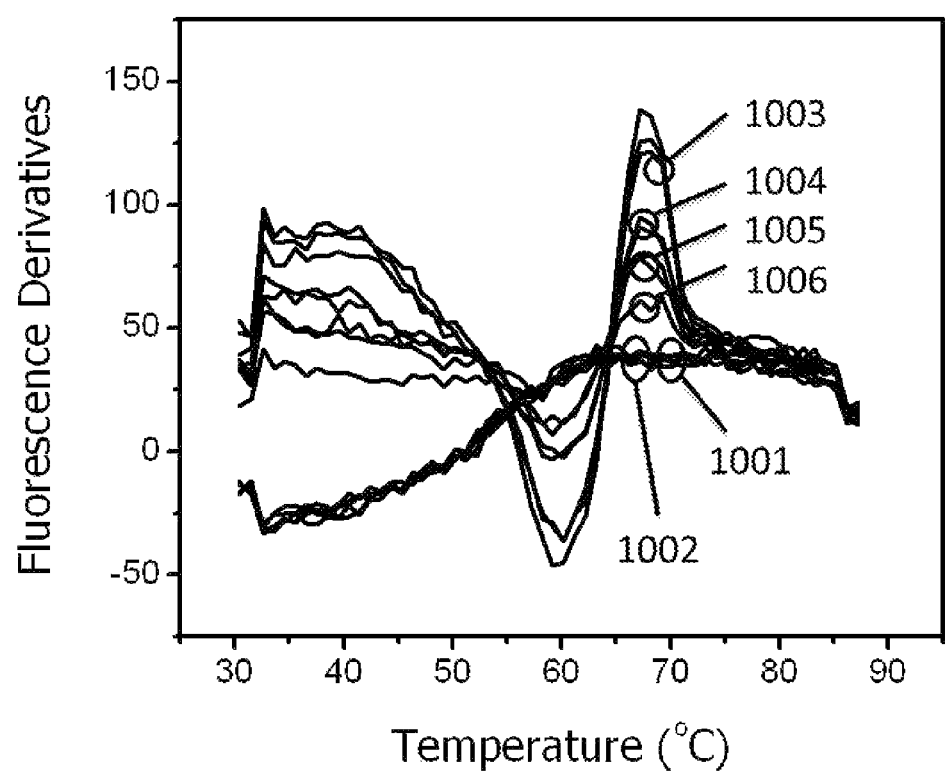
FIG. 10 is a graph containing melting curves (derivative of On-probe fluorescence versus temperature) following LATE-PCR amplifications described in Example 4 for samples containing either first target sequence variant or a mixture of first and second target sequence variants.

Example 4 also includes amplifications using the mismatched excess primer and the modified thermal cycling protocol with samples containing mixtures of first and second target sequence variants: 10,000 copies of the first variant plus 1, 10, 100 or 1000 copies of the second variant (additional samples were a no-template control and only 10,000 copies of the first variant. Following amplification, melt curves were obtained from fluorescence signals from the On probe. As shown in FIG. 10, the curves from all samples containing second target sequence, including the sample containing only one copy in a mixture with 10,000 copies of the first variant, had a peak at about 67° C., attributable to melting of the higher temperature On probe hybrid, and a valley at about 59° C., attributable to melting of the Off probe hybrid. Sanger sequencing confirmed that all of these samples produced amplified product having the sequence of the second target sequence variant in the region of the primer-blocking hairpin oligonucleotide binding site. The sample containing only 10,000 copies of the first variant showed neither the peak nor the valley and fell on top of the curves for the no-template control. FIGS. 9 and 10 show that the assay can detect one copy of the second variant and that the assay has a sensitivity of 1:10,000 (one copy of the second variant in 10,000 copies of the first variant) without false positives.

The decision to use the mismatched primer with the 3' C-C mismatch was based in part on empirical word conducted during the development of embodiments of the present invention. It was found that different single-nucleotide changes affected results. FIGS. 11-16 present results of trials with mismatched excess primer candidates containing six different changes. The samples contained either 10,000 copies of the first target-sequence variant or 10 copies of the second target sequence variant. Amplifications utilized the modified LATE-PCR protocol described above. Shown schematically in each of FIGS. 11-16 is the 3' end of the excess primer and the three nucleotides (CTA) opposite that end in the second strand of the target sequence, highlighting each mismatch by base and position. Curves presented in the figures are real-time SYBR signals, which correspond to curves 903 and 904 in FIG. 9. In certain embodiments, it is preferably to use mismatched primer candidates for which the real-time curves for samples with 10 copies of the second target sequence variant comes up earlier than curves for samples with 10,000 copies of the first variant. By that standard, the primer with the terminal C-C mismatch (FIG. 9) was the best of the candidates for this assay, as curves for samples with 10,000 copies of the first variant of the target sequence never came up. Also by that standard, the primer with the G-A mismatch in the third nucleotide from the 3' end of the primer (FIG. 16) was judged very good. In contrast, the primer with the A-A mismatch in the third nucleotide from the 3' end of the primer (FIG. 15) was judged not acceptable for this particular assay.

The assays described in the Examples were performed without including in the reaction mixture a mispriming-prevention reagent, which was shown to be unnecessary with the target material used, namely, plasmid DNA. For use of genomic DNA, one may consider using a mispriming-prevention reagent, particularly for assays utilizing a mismatched excess primer and a low-temperature annealing step for copying using it, as mispriming tends to be more of a problem at lower temperatures. Mispriming prevention reagents are disclosed in U.S. Pat. No. 7,517,977 and U.S. provisional patent application No. 61/202,565, which are both incorporated herein by reference. Inclusion of a mispriming prevention reagent might, of course, require some adjustment of the other reagents or of the terminal cycling protocol used in an assay.

Example 5 describes experiments performed with genomic DNA from four cell lines obtained from the ATCC. The cell lines had different alleles of the Kras gene. According to the literature, one cell line—K562—has the wild-type Kras gene. In the region of interest it has the sequence GGTGGC. The other three include some cells having different single base pair changes in that region, either G$\underline{A}$TGGC (cell line PL 45), G$\underline{T}$TGGC (cell line CAPAN 2) or G$\underline{C}$TGGC (cell line SW1116).

Sequences were confirmed by amplifying each cell line by LATE-PCR without inclusion of a blocker followed by sequencing utilizing the "Dilute-N-Go" sequencing method described in Rice et al. (2007) Nature Protocols 2(10): 2429-2438; and Jia et al. (2010) Nucl. Acids Res. 38(11): e119. Sequencing revealed that cell line K562 was indeed homozygous wild type, having the GGT allele; and that the other three cell lines, PL45, CAPAN 2 and SW 1116, contained mixtures of the GGT allele and mutant alleles GAT, GTT and GCT, respectively.

Errors introduced by Taq DNA polymerase were investigated when using a blocker. For this purpose plasmid DNA containing the wild-type sequence (SEQ ID NO: 12) was amplified using a blocker, a 2-minute blocker-binding step, and SYBR Green to detect double-stranded amplified product. A series of amplifications in parallel were performed. Appearance of a SYBR Green signal in a sample meant either that plasmid DNA contained a trace level of DNA that was mutant in the blocker-binding sequence or that there was Taq error—spontaneous mutation of the wild-type sequence during extension of the (unblocked) excess primer. Fifteen samples that resulted in a positive SYBR signal were sequenced. Two things were noted. First, some mutations occurred outside the GGTGGC region where naturally occurring mutations have been found. Second, the large majority (over 80%) of the mutations were incorrect insertion of an A nucleotide, and Taq DNA polymerase is known to insert A's at the end of extensions. Based on the evidence, it was concluded that the errors should be considered to be Taq errors, which also could be expected when starting with genomic DNA and need to be taken into account. In the assay of mixtures in this example, the blocker has 18 nucleotides that are complementary to the wild-type sequence to be blocked. Of those nucleotides, eight overlap the limiting primer. If a Taq-dependent error occurs within the sequence to which the limiting primer binds, the limiting primer will fail to bind, and amplification will stop. If, however, the error falls within the 10 nucleotides that are within the blocker-binding sequence but outside the limiting primer-binding sequence, the blocker will not bind but the limiting primer will, so amplification will proceed. As noted earlier, the error rate of Taq DNA polymerase has been reported to be up to about $1 \times 10^{-4}$ errors per base (see, for example, Eckert, K. A. and Kunkel, T. A. (1991) PCR Methods Appl. 1; Tindall, K. R and Kunkel, T. A. (1988) Biochemistry 27: 6008-6013). Therefore, for 10,000 copies of wild-type DNA, there would be up to 10 errors in a sequence that is 10 bases long. Absent steps to reduce the polymerase error rate, it is prudent to anticipate 0.1% mutations attributable to Taq-caused errors. Accordingly, assay results indicating 10 or fewer copies of mutations per 10,000 copies of a wild-type genome cannot conservatively be scored a true mutation, since the mutations could either be true (that is, existing in the starting amplification reaction mixture) or introduced through polymerase error.

To improve the sensitivity of the assay, one or more steps to reduce the impact of Taq DNA polymerase errors can be employed. One such step is to utilize a mismatched excess primer with a modified thermal cycling protocol as described in Example 4. As described, that additional step boosted the sensitivity of the assay 10X. This was accomplished by beginning the amplification process with 10 thermal cycles in which the blocker was allowed to bind to all wild type template strands and the limiting primer was allowed to bind and extend on all available mutant template strands, without dropping the temperature low enough to bind a mismatched excess primer. In this way all 10×amplified limiting primer strands will have bono fide mutations prior to the possibility of introducing an artificial mutation in the excess primer strand by Taq error. This 10-fold increase in sensitivity means that a score of "inconclusive" is only required when there is one or less than one mutant strands per 10,000 (0.01%) template strands.

In addition, as one versed in the art will appreciate another step that can be taken to increase the specificity and, hence, the sensitivity of the assay is to utilize a thermal stable DNA polymerase with a higher intrinsic fidelity than conventional Taq polymerase. Several such high fidelity enzymes are commercially available, including Platinium Taq DNA polymerase high fidelity, Pfu DNA polymerase and Phusion high fidelity DNA polymerase, and others. In the assay for mixtures in Example 5, Platinum Taq DNA polymerase was used. Since each such enzyme has its own optimal buffer, it may be necessary to adjust the design of the blocker and/or primers so that each retains it optimal melting temperature.

As reported in Example 5, genomic DNA from the four cell lines was amplified by LATE-PCR using a limiting primer and an excess primer that both were perfectly complementary to all of the alleles. For signal generation a Lights-On probe a molecular beacon hairpin probe was used having a stem two nucleotides long labeled on one end with the fluorophore Quasar 670 (Quas670) and on the other end with a Black Hole Quencher 2 (BHQ2); and a combination hairpin blocker and Lights-Off probe a hairpin oligonucleotide were used with a stem five nucleotides long labeled at one end with a Black Hole Quencher 2 (BHQ2). The blocker/Off probe is described in Example 4. The blocker/Off probe was perfectly complementary to the DNA sequence having the wild-type GGT allele, and it was used to block amplification of genomic DNA containing that allele. Using starting mixtures that contained 10,000 copies of wild-type DNA from cell line K562 as the abundant first variant of the target sequence and varying amounts (from 10 to 1000 copies) of each of mutant-containing cell lines PL45, CAPAN 2 and SW 1116 to contribute the rare second variant, it was determined that the assay according to this invention had a detection sensitivity of 0.5% or better in the purified genomic DNA. Further, considering the entireties of the melt curves obtained with the different (GAT, GTT, GCT) mutants in FIGS. 18-20, it is believed that the identity of the mutant that is present can be ascertained from the fluorescence signature of a sample.

Utilization of primers with 5' linear tails, or primers with 5' flip tails enables another strategy for reducing the chances of amplifying a product that contains a variant sequence due to a DNA polymerase error, rather than a variant present in the original sample. Primers with 5' linear tails or 5'flip tails have a 3' linear head section, that functions initially as described for the first primer and the second primer. The 3' linear head of the second primer (the excess primer in LATE-PCR) may be perfectly complementary to the target sequence, or it may be mismatched as described in Example 4. Once a pair of primers with 5' linear tails, or 5'flip tails, or one 5' linear tail and one 5' flip tail has been incorporated into a double-stranded target, the length of said double-stranded target increases, and each strand contains a sequence of complementary to a primer's tail. Thus, once these primers are incorporated, $Tm_{[0]}$ of each primer becomes $Tm_{[0']}$. $Tm_{[0']}$ for each primer is necessarily higher than the corresponding $Tm_{[0]}$ and can, in fact, be higher than the Tm of the blocker to its target strand. Thus, once tailed primers have been incorporated into the double-stranded template, amplification can proceed without involvement of the blocker, in which case the blocker no longer functions to select for amplification of target variants, whether they were present initially or may have arisen via polymerase errors of incorporation.

The design options for primers with 5' linear tails are very flexible but must meet the following criteria: 1) The 3' linear head section of a primer with a 5' linear tail must be complementary to a target strand and must meet the criteria described above for either a first primer, including a first limiting primer, or a second primer, including an excess primer; 2) The 5' linear section of a primer with a 5' linear tail must not include more than 2, preferably not more than 1 complementary nucleotide pairs (complementary to each other, to the 3' linear section itself, or to the sequence which lies 3' to the target-binding sequence of the 3' linear section). In addition, the concentration-dependent Tm[0'] of the primer with a 5' linear tail that serves as a first primer, which may be a limiting primer (L), must be equal to or higher than the concentration dependent $Tm_{[0']}$ of the primer with a 5' linear tail that serves as a second primer, which may be an excess primer (X). In other words $(Tm^{L}_{[0']} - Tm^{X}_{[0']}) \geq 0$. In some cases it may be preferred to utilize 5' tailed primers in which $Tm^{L}_{[0']}$ of the first primer is higher than the melting temperature at which the blocker hybridizes to the wild-type target sequence. An example of a pair of primers with 5' linear tails that meet the above criteria is shown in Example 6. However, the pair of primers shown in Example 6 is not necessarily the optimal possible pair of primers for the target utilized in Example 6.

As stated earlier, 5' flip-tail primers are a special class of 5' tailed primers, because they include a temperature-dependent hairpin structure. The design options for such primers are quite flexible but include the following four elements, listed in the 3' to 5' direction: 1) a 3' linear "head" section which functions as the first primer or the second primer during the initial thermal cycle in which it binds to its complementary target; 2) a "non-complementary neck" which connects the 3' linear section to the rest of the primer; 3) a "body" section comprised of a stem-loop section comprised of a sequence folded on itself; 4) the 5' end of the primer which may or may not extend beyond the stem and may or may not be labeled. The 3' linear head section of a primer with a 5' flip tail must be complementary to a target strand and must meet the criteria describe above for either a first primer or a second primer, including a first limiting primer or a second excess primer. The "neck" of the 5' flip-tail primer must be comprised of 0-10 additional nucleotides that are not complementary to the target and serve as a "neck" between the 3' linear head of the primer and the body section that lies 5' of the neck. The nucleotides comprising the body section must form a temperature-dependent stem-loop structure that is closed at $Tm_{[0]}$ but is open at $Tm_{[0']}$. The stem-loop structure typically comprises a stem that is 4-6 base-pairs long and a loop that is greater than 3 nucleotides long. In addition, the final concentration-dependent melting temperature of the primer with a 5' flip tail that serves as a first primer ($Tm_{[0']}$ or, when it is a first limiting, $Tm^{L}_{[0']}$) must be equal to or higher than the final concentration-dependent melting temperature of the primer with a 5' flip-tail that serves as a second primer ($Tm_{[0']}$ or, when it is a second excess primer $Tm^{X}_{[0']}$). In other words $(Tm^{L}_{[0']} - Tm^{X}_{[0']}) \geq 0$. In some cases it may be preferred to utilize 5' tailed primers in which $Tm^{L}_{[0']}$ of the first primer is higher than the melting temperature at which the blocker hybridizes to the wild-type target sequence.

An example of a LATE-PCR amplification protocol utilizing a pair of primers with 5' tails that meet the above criteria is given in Example 6. In the protocol of Example 6a blocker-binding step is included only in the first few cycles, two amplification cycles in this case, in which amplicons are created that are complementary to the entire primers. Thereafter, cycling is performed at high temperatures without a blocker-binding step so that only targets complementary to the entire primers participate. Through the use of such an amplification protocol with a tailed limiting primer and a tailed excess primer, the Taq polymerase error does not affect the selective amplification, and no false positive result is obtained. The rare mutation detection sensitivity reaches 0.1%. As will be appreciated, extension of the excess primer on the synthesized limiting primer strand or strands creates the possibility for Taq errors to arise in the blocker-binding sequence. Therefore, in Example 6 a protocol was tested which begins with one thermal cycle in which the blocker-binding step is utilized prior to binding the first (limiting) primer based on its $Tm^L_{[0]}$, and the temperature is never lowered sufficiently for the second (excess) primer to bind to its template strand, followed by only one thermal cycle in which the blocker-binding step is utilized and the temperature is then lowered sufficiently for the second primer to bind to its template strand based on $Tm^X_{[0]}$, followed by multiple thermal cycles during which the temperature is only lowered sufficiently for the first primer and the second primer to bind and extend on their respective template based $Tm^L_{[0']}$ and $Tm^X_{[0']}$, while the blocker remains unbound because said temperature is higher than the Tm of the blocker to the target strand of the first variant.

The primers in Example 6 or in the preceding examples are not necessarily the optimal possible pair of primers for selection of the second variant over the first variant used in the respective examples. As one versed in the art will appreciate, primer design often must be optimized experimentally. The basis for optimization is also demonstrated in Example 6. It includes the use of several dilutions of the wild-type target sequence (the abundant first variant of the target sequence) and one or more variant sequences (the rare second variants of the target sequence), along with the blocker, the primer sequences to be tested, plus a dye such as SYBR Green or fluorescent hybridization probes to visualize the kinetics and amount of double-stranded and single-stranded products that are generated from the targets, alone or in mixtures. In particular, for each pair of primers (5' linear primers, 5' flip-tail primers, or pair comprised of one 5' linear and one 5' flip-tail primer), it is useful to measure the extent of amplification inhibition, as indicated by increase in threshold cycle, $\Delta C_T$, that occurs when each target is amplified in the presence of the blocker as compared to amplification in the absence of the blocker. In the case of target variants that do not bind the blocker, $\Delta C_T$ should be very small, preferably not more than 3 cycles, most preferably not more than 1 cycle. In the case of wild-type target that does bind the blocker, $\Delta C_T$ should be as large as possible, preferably at least 5 cycles, more preferably at least 10 cycles. In addition, mixtures of wild-type and variant target sequences can be used to optimize pairs of primers with 5' tails. By optimizing tailed primer pairs, variant targets can be detected in mixtures having second target variant-to-first target ratios of 1/100, preferably 1/1000, more preferably 1/10,000, and most preferably 1/100,000 or even 1/1,000,000.

In addition, the general method described here is very flexible. Not only the primers, but also the thermal profiles utilized in Example 6 and the other examples are necessarily optimal for selective amplification of the second variant over the first variant. For instance, the system described here allows methods utilizing linear primers without tails and a hairpin blocker whose Tm is higher than the Tm of the first primer, as described in Examples 1-5, combined with a protocol in which a blocker-binding step is employed for the first few, preferably not more than ten and most preferably only two, thermal cycles, as described in Example 6, followed by one to ten thermal cycles in which the hairpin blocker is bypassed (not employed) by rapidly dropping the temperature to hybridize both primers to their respective target strands without allowing time for the blocker to hybridize, followed by a few, preferably one or two, cycles in which a blocker-binding step is again employed to allow the hairpin blocker to hybridize its accumulated target strands of the first variant, followed by multiple cycles in which the blocker is once again bypassed by rapidly dropping the temperature to bind both primers.

A protocol of the above design will favor selective amplification of the second variant over the first variant at two times in the reaction. The first time the second variant will be selected over the first variant without the possibility of generating novel variants caused by Taq errors. The second time that the second variant is selected over the first variant the blocker will also select for any novel variants that have accumulated due to Taq errors in the region of the blocker binding to its first variant template. However, the absolute number of such reaction-generated novel variants will be very low relative to the already accumulated copies of any original second variant present in the original sample. In the cycles thereafter further accumulation of those novel variants will lag far behind the amplification of second variant. Indeed, when the first (limiting) primer is used up by either the exponential amplification of the first variant, the second variant, or both, additional exponential amplification of the novel variants will stop, and linear amplification by extension of only the second (excess) primer will begin. The signals generated by the binding of the fluorescent probes at the end of the reaction will only reflect the presence of the second variant in the original sample, because their accumulated numbers will be manyfold higher than the numbers of accumulated novel strands.

EXAMPLES

Example 1

Binding Kinetics of Hairpin Blockers with Different Stem Lengths

Molecular beacon probes have a stem-loop structure provides a competition between formation of the hairpin stem hybrid and a probe-target hybrid. That competition serves to increase probe specificity, including discrimination against a single base difference (single nucleotide change). Whereas conventional linear (or random coil) probes have a Tm against a perfectly complementary variant of a target sequence that is a few degrees higher than is Tm against a variant having a single base change, molecular beacon hairpin probes have a larger difference, typically 7-10° C. See, for example, Marras, S. A. E. et al. (1999), Genetic Analysis: Biomolecular Engineering 14: 151-156. In this example it was demonstrated that with a given loop sequence, the difference in Tm between such target variants remains relatively constant over stem lengths of 1-9 nucleotides, increasing modestly at longer lengths, but the kinetics of hybridization change with stem length, longer stems having markedly decreased rates of hybridization.

Using primer-blocking hairpin oligonucleotide candidates having the same target-binding sequence 18 nucleotides long, several different stem lengths were tested from 1-9 nucleotides against a target variant that was perfectly complementary to the target binding sequence and a target variant differing by a single nucleotide. Each hairpin blocker candidate was labeled at its 5' terminus with a fluorophore, Cal Orange 560, and at its 3' terminus with a non-fluorescent quencher, Dabcyl. Sequences of the blocker candidates and target variants are set forth below. For the blockers, the 18 nucleotides that were complementary to the perfectly complementary variant of the target sequence are underlined, and the stem-forming terminal nucleotides are bolded. It will be noted that two nucleotides are common to the stem and the target-binding sequence. For the target variants, the nucleotide that is different in the variants is underlined and bolded.

Primer-Blocking Hairpin Oligonucleotides (Blockers)

```
                                          (SEQ ID NO. 1)
Blocker BL:
5' Cal Org 560-GCCTACGCCACCAGCTCC-Dabcyl 3'

(SEQ ID NO. 2)
Blocker B62:
5' Cal Org 560-CGCCGCCTACGCCACCAGCTCCGGCG-
Dabcyl 3'

(SEQ ID NO. 3)
Blocker B71:
5' Cal Org 560-GCGCCGCCTACGCCACCAGCTCCGGCGC-
Dabcyl 3'

(SEQ ID NO. 4)
Blocker B77:
5' Cal Org 560-CGCGCCGCCTACGCCACCAGCTCCGGCGCG-
Dabcyl 3'

(SEQ ID NO. 5)
Blocker B82:
5' Cal Org 560-CCGCGCCGCCTACGCCACCAGCTCCGGCGCGG-
Dabcyl 3'

(SEQ ID NO. 6)
Blocker B86:
5'Cal Org 560-GCCGCGCCGCCTACGCCACCAGCTCCGGCGC
GGC-Dabcyl 3'
```

DNA Target Sequence Variants
First Variant (Perfectly Complementary to Blocker Candidates):

```
                                          (SEQ ID NO. 7)
5'GTAGTTGGAGCTGGTGGCGTAGGCAAGAGT 3'
```

Second Variant (Single Nucleotide Mismatch Versus Blocker Candidates):

```
                                          (SEQ ID NO. 8)
5'GTAGTTGGAGCTGATGGCGTAGGCAAGAGT 3'
```

The binding kinetics and thermodynamics of the blockers was analyzed by the probe-target melting and annealing. Twenty-five microliter (µl) reaction mixtures contained 1×PCR buffer with 3 millimolar (mM) Mg$^{++}$ plus 100 nanomolar (nM) of one of the blocker candidates and 250 nM of one of the target sequence variants. Reaction mixtures were also ran with no target. The reaction mixtures placed in a thermal cycler and subjected to the following thermal cycling profiles: first, 95° C. for 10 seconds (s), 60° C. for 30 minutes, with fluorescence detection every 5 seconds; then 30° C. for 20 minutes, followed by melting to 95° C. in steps of 1° C. every 30 s., with fluorescence detection at the end of each step.

Tm's of the blockers against each target variant was obtained from melting curves, the first derivative of fluorescence versus temperature. Results are presented in Table 1.

TABLE 1

| Blocker (stem length) | Tm, complementary target | Tm, mismatched target | ΔTm |
|---|---|---|---|
| BL (one NT) | 72° C. | 61° C. | 11° C. |
| B62 (five NT) | 67 | 57 | 10 |
| B71 (six NT) | 64 | 54 | 10 |
| B77 (seven NT) | 62 | 52 | 10 |
| B82 (eight NT) | 61 | 49 | 12 |
| B86 (nine NT) | 52 | 38 | 14 |

Although the equilibrated allele-specific window (ΔTm) changes relatively little with the length of the stem, the binding kinetics change dramatically. Binding kinetics were monitored by fluorescence reading every 5 seconds at 60° C., following annealing from 95° C. FIG. 2 presents fluorescence intensity from the Cal Orange fluorophore over time for blockers BL, B62 and B71, all of which bound to the perfectly complementary target variant at 60° C. As can be seen from FIG. 2, the binding kinetics depend on the length of the stem. It took about 30 seconds for blocker BL (stem 1 nucleotide (NT) long) to bind completely to the target variant (curve 21). However, with 5 base-pair (bp) stem, that is, a stem five nucleotides (NT) long, blocker B62 took about 2 minutes to totally bind to the same target variant (curve 22), and blocker B71, with a 6-bp stem, took about 3 minutes to do so (curve 23). At 60° C., blocker BL bound to the mismatched target variant, but none of the other blockers did (data not shown).

The binding kinetics of B62 to both the first variant of the target sequence (perfectly complementary) and the second variant of the target sequence were monitored. In a first protocol, the blocker and target were kept at 30° C. for 10 minutes to ensure that the equilibrium state was reached, and then the samples were melted up to 95° C. with an increase of 1° C. every 30 sec. Fluorescence from the Cal Orange fluorophore was obtained at each temperature. Samples were run in duplicate, including a no-template control (NTC). FIG. 6 presents the fluorescence readings as a function of temperature during melting. Curves 61 are the first target sequence variant, in which point A is the fluorescence at 60° C. and point C is the fluorescence at 50° C. Curves 62 are the second target sequence variant, in which point B is the fluorescence at 60° C. and point D is the fluorescence at 50° C. Curves 63 are the NTC. In a second protocol, the samples were kept at 95° C. for 3 minutes to totally melt target and blocker, and then the samples were annealed down to 30° C. in steps of 10° C. for only 10 sec at each step. Curves 64 are the first target sequence variant. Curves 65 are the second target sequence variant, in which point E is the fluorescence from 10 seconds at 50° C. after a drop from 60° C. Curves 66 are the NTC.

Example 2

Effectiveness of a Primer-Blocking Hairpin Oligonucleotide in Selectively Amplifying a Rare Mutant Allele DNA Target Sequence Variant Primer-blocking hairpin oligonucleotide B62 (see Example 1) was tested for its ability to block amplification of a first, perfectly complementary, target sequence variant but to permit amplification of a second target sequence variant containing a single nucleotide mismatch in the blocker-binding site using a modified PCR thermal cycling profile. The target sequence variants included the same blocker-binding sites as the target sequence variants used in Example 1. For purposes of probing and analysis, the second target sequence variant was provided with a second nucleotide difference outside the binding regions of the primers and blocker, so that an allele-discriminating molecular beacon probe complementary to the first target sequence variant could interrogate and distinguish the amplified products. In this instance the probe was a short-stem, mismatch-tolerant molecular beacon probe labeled on its 5' end with a Black Hole Quencher 2 (BHQ2) and on its 3' end with a fluorophore (Quasar 670). This probe hybridized to the perfectly complementary first target sequence variant with a Tm of 55° C. and to the imperfectly complementary second target sequence variant with a Tm of 43° C.

LATE-PCR amplifications were performed using a limiting primer and an excess primer that were perfectly complementary to both target sequence variants. The concentration-adjusted Tm of the limiting primer at the start of amplification was 54° C., and the concentration-adjusted Tm of the excess primer was 52° C. As set forth in Table 1 in Example 1, the Tm of blocker B62 versus the first sequence variant was 67° C., and the Tm of blocker B62 versus the second target sequence variant was 57° C. The hybridization rate for blocker B62 is shown in FIG. 2. The binding site of Blocker B62 overlapped the binding site of the limiting primer by eight NT. The nucleotide that differed in the blocker-binding site was three NT downstream from the 3' terminus of the limiting primer. Targets were plasmid DNA (Epoch Biolabs, Inc, Sugar Land, TX.). The sequences of the oligonucleotides are set forth below. For the blocker, the 18 nucleotides that were complementary to the perfectly complementary first variant of the target sequence are underlined, and the stem-forming terminal nucleotides are bolded. For the target sequence variants, one strand sequence is given, namely, the strand to which the limiting primer and primer-blocking hairpin oligonucleotide are complementary. In the target sequences the nucleotides that differ in the blocker-binding site are underlined, and the nucleotides that differ in the molecular beacon probe binding site are bolded.

(SEQ ID NO. 2)
Blocker B62:
5' Cal Org 560-CGCCGCCTACGCCACCAGCTCCGGCG-
Dabcyl 3'

(SEQ ID NO. 9)
Limiting Primer:
5'ACTCTTGCCTACGC 3'

(SEQ ID NO. 10)
Excess Primer:
5'GTGGAGTATTTGATAG 3'

(SEQ ID NO. 11)
Molecular Beacon Probe:
5'BHQ2-CAAGAACATGTCACACATAATG-Quas670 3'

First Variant of the Target Sequence:

(SEQ ID NO. 12)
5'CTGGTGGAGTATTTGATAGTGTATTAACCTTATGTGTGACATGTTCTA

ATATAGTCACATTTTCATTATTTTTATTATAAGGCCTGCTGAAAATGACT

GAATATAAACTTGTGGTAGTTGGAGCTGGTGGCGTAGGCAAGAGTGC 3'

Second Variant of the Target Sequence:

(SEQ ID NO. 13)
5'CTGGTGGAGTATTTGATAGTGTATTAACCTTATGTGTCACATGTTCTA

ATATAGTCACATTTTCATTATTTTTATTATAAGGCCTGCTGAAAATGACT

GAATATAAACTTGTGGTAGTTGGAGCTGATGGCGTAGGCAAGAGTGC 3'

LATE-PCR amplifications were performed using 25 μl reaction mixtures containing 1×PCR buffer (Invitrogen, Carlsbad, Calif.), 3 mM $MgCl_2$, 200 nM dNTPs, 0.24×SYBR Green (Invitrogen, Carlsbad, Calif.), 50 nM limiting primer, 1000 nM excess primer, 500 nM blocker B62, 200 nM molecular beacon probe, 1 unit of Platinium Taq DNA polymerase (Invitrogen, Carlsbad, Calif.), and different concentrations of one of the plasmid DNA target variants that gave starting copy numbers in the range of $10^0$ to $10^6$, obtained by serial dilution. Amplification reactions were run in a duplicate.

Three thermal profile conditions were tested for these reactions. The profiles were: 95° C. for 3 min followed by 55 cycles of 95° C. for 10 s, 60° C. for 0 min, 1 min or 2 min, 50° C. for 10 s, 72° C. for 30 s. Following amplification, the reaction mixture was heated to 30° C. for 10 min and then melted to 90° C. in steps of 1° C. increments at 30 s intervals. SYBR Green signals were detected in real time during the primer extension portion of all PCR cycles. Quasar 670 signals from the molecular beacon probe were detected during the melting process.

Figure 3B:
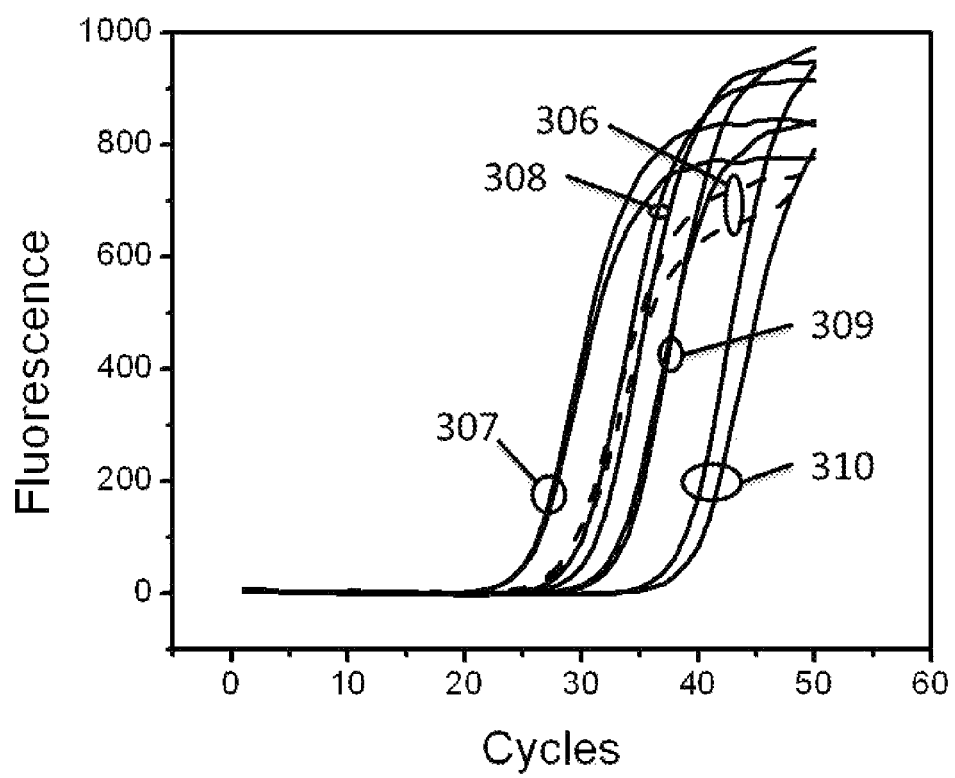
Figure 3C:
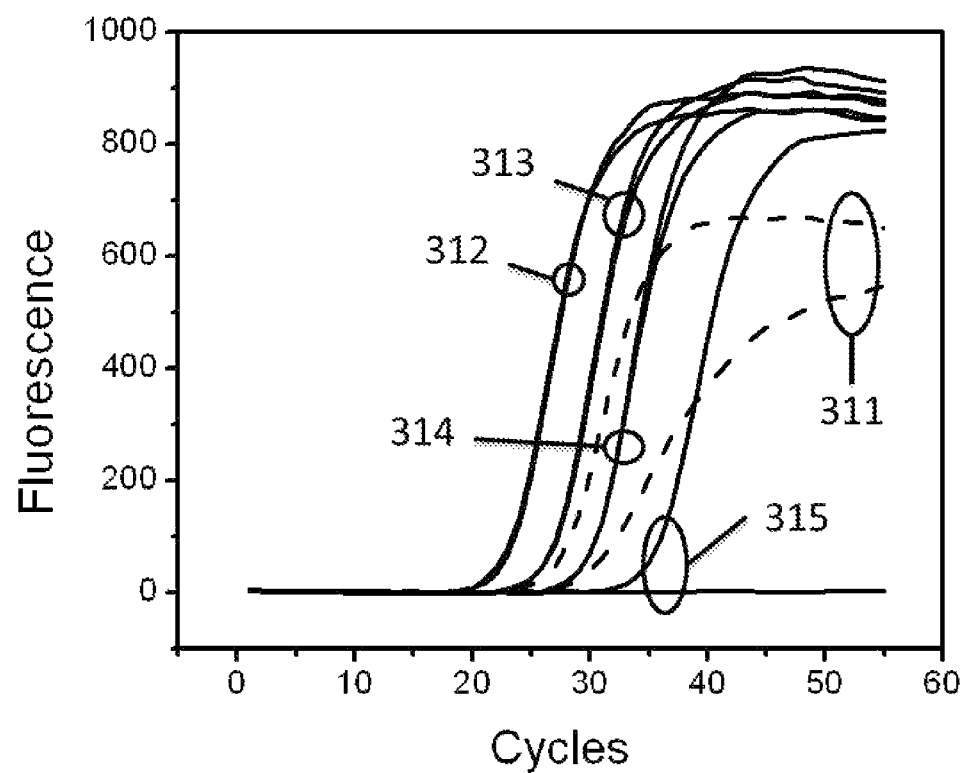

Real-time fluorescence readings of SYBR Green are presented in FIGS. 3A-3C. FIG. 3A presents the curves of fluorescence versus cycle number for amplifications with no (0 min) 60° C. step for reaction mixtures containing $10^6$ copies of the first variant of the target sequence: (curves 301), $10^3$ copies of the second variant (curves 302), $10^2$ copies of the second variant (curves 303), $10^1$ copies of the second variant (curves 304), and $10^0$ copies of the second variant (curves 305). FIG. 3B presents the curves of fluorescence cycle number for amplifications with a 1 min 60° C. step for reaction mixtures containing $10^6$ copies of the first variant of the target sequence: (curves 306), $10^3$ copies of the second variant (curves 307), $10^2$ copies of the second variant (curves 308), $10^1$ copies of the second variant (curves 309), and $10^0$ copies of the second variant (curves 310) FIG. 3C presents the curves of fluorescence cycle number for amplifications with a 2 min 60° C. step for reaction mixtures containing $10^6$ copies of the first variant of the target sequence: (curves 311), $10^3$ copies of the second variant (curves 312), $10^2$ copies of the second variant (curves 313), $10^1$ copies of the second variant (curves 314), and $10^0$ copies of the second variant (curves 315).

Figure 4:
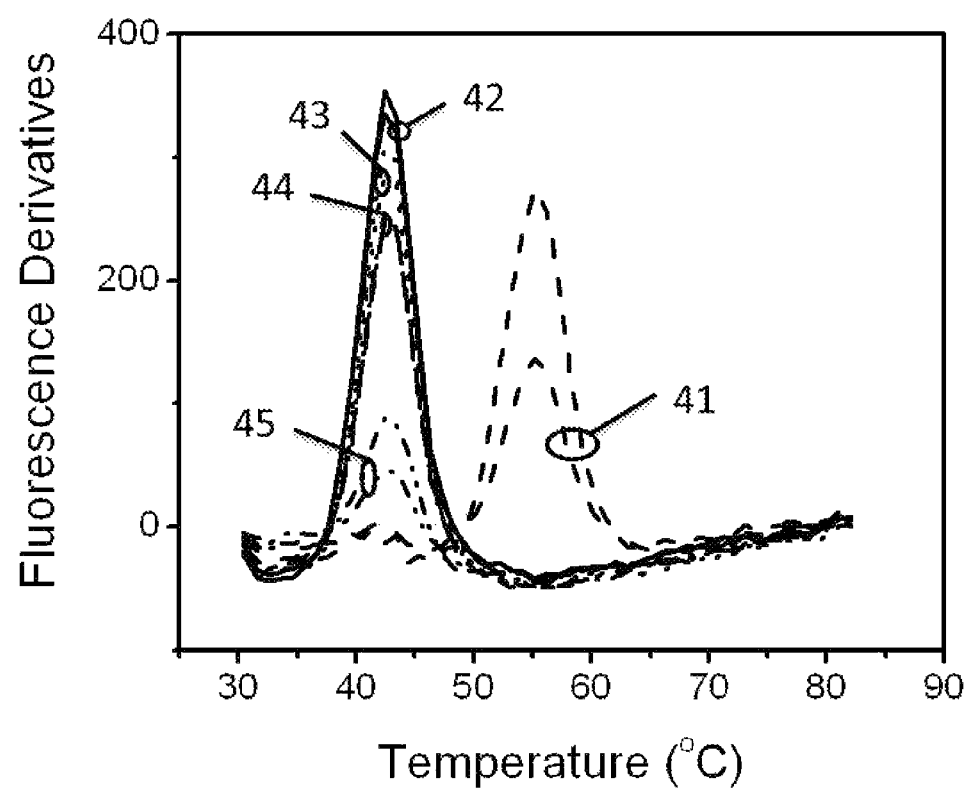
FIG. 4 is a graph containing melting curves (derivative of probe fluorescence versus temperature) following LATE-PCR amplifications described in Example 2 for samples containing either first target sequence variant or second target sequence variant.

The specificity of amplification was monitored by the molecular beacon probe, which had a Tm versus tie first variant of the target sequence of 55° C. and a Tm versus the second variant of 43° C. All the product from 1 million copies of the first target sequence variant gave a melting peak at 55° C. and all the products from the second target sequence variant gave a melting peak at 43° C., confirming the specificity of the amplification reaction. FIG. 4 shows the melting curves (derivative curves of fluorescence versus temperature) for products following the thermal cycling profile that included the 60° C. step of 2 min. Curves 41 are the sample containing 1 million initial copies of the first target sequence variant. Curves 42 are the sample containing 1000 initial copies of the second target sequence variant. Curves 43 are the sample containing 100 initial copies of the second variant. Curves 44 are the sample containing 10 copies of the second variant.

And curve 45 is the sample containing 1 copy of the second variant. It will be noted that one of the duplicate reaction mixtures with initial single copy of the second target sequence variant did not produce any melting peak. This fact was attributed to the fact that, with dilution to the single copy level, not all the samples can be expected to have DNA, and some can be expected to have more than one copy.

The selectivity against the said first variant of the target sequence of LATE-PCR amplification using the primer-blocking hairpin oligonucleotide B62 and a cycle step of 2 min at 60° C. was tested with reaction mixtures containing both the first variant of the target sequence and the second variant of the target sequence. Reaction mixtures were as described above, except that they contained 10 copies of said second variant in combination with different amounts, from 10 copies to 100,000 copies, of the first variant. Thermal cycling was as described above with the 60° C./2 min step. FIG. 5 presents the melting curves (derivative of fluorescence of the molecular beacon's Quasar 670 fluorophore versus temperature) for 10 copies of the first variant (curves 51), 100 copies of the first variant (curves 52), 1,000 copies of the first variant (curves 53), 10,000 copies of the first variant (curves 54) and 100,000 copies of the first variant (curves 55). Those mixtures gave a ratio of second target variant to first target variant of from 1:1 to 1:10,000. With a 1:1 ratio and a 1:10 ratio, only the melting peak of the said second variant is observed. With a ratio of 1:100, the peak of said first target just begins to show up. It becomes stronger at a ratio of 1:1,000, and the peak for the second variant is diminished. At a ratio of 1:10,000, the peak for the first variant remains strong, and the peak for the second variant is low although still recognizable. Further increase the concentration of the said first variant with such a long cycling profile resulted in product evolution and no melting peaks were observed (data not shown).

Although the above data appear to show that the use of the primer-blocking hairpin oligonucleotide is capable of detecting one copy of the second sequence variant in the presence of 10,000 copies of the first sequence variant, such a conclusion is not definitive, because it does not take into account possible Taq polymerase errors during extension of the second primer on its template strand. Such an altered strand could fail to bind the primer-blocking hairpin oligonucleotide in subsequent thermal cycles.

Example 3

Effect of Different NT Changes in the Blocker-binding Site

This example utilizes primer-blocking hairpin oligonucleotide B62, the same limiting and excess primers, and the same first target sequence variant as were used in Example 2. It also uses as a second target sequence variant a sequence that that is the same as the second variant used in Example 2 except that it does not have the additional nucleotide change for a molecular beacon probe. This example also uses several additional second target sequences differing from the first variant by a single NT in the blocker-binding site. For clarity, the several second target sequences (whose amplification it is desired to enhance) are referred to here as target sequence variants 2-7. This example utilizes fluorescent signals from blocker B62 for detection. Sequences of oligonucleotides used in this example are set forth below. For the blocker, the 18 nucleotides that were complementary to the perfectly complementary first variant of the target sequence are underlined, and the stem-forming terminal nucleotides are bolded. For the target sequence variants, one strand sequence is given, namely, the strand to which the limiting primer and primer-blocking hairpin oligonucleotide are complementary. In the target sequences the nucleotides that differ from the first variant in the blocker-binding site are underlined.

```
                                           (SEQ ID NO. 2)
Blocker B62:
5' Cal Org 560-CGCCGCCTACGCCACCAGCTCCGGCG-
Dabcyl 3'

(SEQ ID NO. 9)
Limiting Primer:
5'ACTCTTGCCTACGC 3'

(SEQ ID NO. 10)
Excess Primer:
5'GTGGAGTATTTGATAG 3'
```

First Target Sequence Variant:

```
                                           (SEQ ID NO. 12)
5'CTGGTGGAGTATTTGATAGTGTATTAACCTTATGTGTGACATGTTCTA
ATATAGTCACATTTTCATTATTTTTATTATAAGGCCTGCTGAAAATGACT
GAATATAAACTTGTGGTAGTTGGAGCTGGTGGCGTAGGCAAGAGTGC 3'
```

Target Sequence Variant 2:

```
                                           (SEQ ID NO. 14)
5'CTGGTGGAGTATTTGATAGTGTATTAACCTTATGTGTGACATGTTCTA
ATATAGTCACATTTTCATTATTTTTATTATAAGGCCTGCTGAAAATGACT
GAATATAAACTTGTGGTAGTTGGAGCTGATGGCGTAGGCAAGAGTGC 3'
```

Target Sequence Variant 3:

```
                                           (SEQ ID NO. 15)
5'CTGGTGGAGTATTTGATAGTGTATTAACCTTATGTGTGACATGTTCTA
ATATAGTCACATTTTCATTATTTTTATTATAAGGCCTGCTGAAAATGACT
GAATATAAACTTGTGGTAGTTGGAGCTGTTGGCGTAGGCAAGAGTGC 3'
```

Target Sequence Variant 4:

```
                                           (SEQ ID NO. 16)
5'CTGGTGGAGTATTTGATAGTGTATTAACCTTATGTGTGACATGTTCTA
ATATAGTCACATTTTCATTATTTTTATTATAAGGCCTGCTGAAAATGACT
GAATATAAACTTGTGGTAGTTGGAGCTGCTGGCGTAGGCAAGAGTGC3'
```

Target Sequence Variant 5:

```
                                           (SEQ ID NO. 17)
5'CTGGTGGAGTATTTGATAGTGTATTAACCTTATGTGTGACATGTTCTA
ATATAGTCACATTTTCATTATTTTTATTATAAGGCCTGCTGAAAATGACT
GAATATAAACTTGTGGTAGTTGGAGCTAGTGGCGTAGGCAAGAGTGC3'
```

Target Sequence Variant 6:

```
                                           (SEQ ID NO. 18)
5'CTGGTGGAGTATTTGATAGTGTATTAACCTTATGTGTGACATGTTCTA
ATATAGTCACATTTTCATTATTTTTATTATAAGGCCTGCTGAAAATGACT
GAATATAAACTTGTGGTAGTTGGAGCTTGTGGCGTAGGCAAGAGTGC3'
```

Target Sequence Variant 7:

```
                                              (SEQ ID NO. 19)
5'CTGGTGGAGTATTTGATAGTGTATTAACCTTATGTGTGACATGTTCTA
ATATAGTCACATTTTCATTATTTTTATTATAAGGCCTGCTGAAAATGACT
GAATATAAACTTGTGGTAGTTGGAGCTCGTGGCGTAGGCAAGAGTGC3'
```

LATE-PCR amplifications were carried out in 25 μl volume consisting of 1×PCR buffer (Invitrogen, Carlsbad, Calif.), 3 mM MgCl$_2$, 200 nM dNTPs, 50 nM limiting primer, 1000 nM excess primer, 0.24×SYBR Green (Invitrogen, Carlsbad, Calif.), 500 nM blocker B62, 1 unit of Taq DNA polymerase (Invitrogen, Carlsbad, Calif.), plus either 10 copies of the first target sequence variant or 10 copies of one of the second variants of the target sequence (target sequence variant 2 to target sequence variant 7). The thermal profile conditions for these reactions were as follows: 95° C. for 3 min, followed by 55 cycles of 95° C./10 s, 60° C./2 min, 50° C./10 s, 72° C./20 s, followed by a 10 min soak at 30° C., and then a melt starting at 30° C. with 1° C. increments at 30 s intervals to 90° C. The melting curves were monitored by the Cal Orange 560 signals from the blocker, which signals upon hybridization. Samples are run in duplicates.

The raw melting data (fluorescence versus temperature) were self-normalized to 70° C., where the blocker is not expected to bind on any target, and at 45° C., where the blocker should bind on each of the target sequence variants. The data throughout the melting curve for each sample was subtracted by the data at 70° C. to normalize the data at 70° C. to 0. Then the subtracted data at all temperature for each sample was divided by the subtracted data at 45° C. to normalized the data at 45° C. to 1.

FIG. 7 shows the normalized data for each sample. Line 71 is the normalized data of the first target sequence variant. Line 72 is the normalized data of target sequence variant 2, which has a GGT-to-GAT single NT change under the blocker-binding site. Line 73 is the normalized data of target sequence variant 3, which has a GGT-to-GTT single NT change. Line 74 is the normalized data of target sequence variant 4, which has a GGT-to-GCT single NT change. Line 75 is the normalized data of target sequence variant 5, which has a GGT-to-AGT single NT change. Line 76 is the normalized data of target sequence variant 6, which has a GGT-to-TGT single NT change. Line 77 is the normalized data of target sequence variant 7, which has a GGT-to-CGT single NT change.

As shown in FIG. 7, the amplification of the first variant of the target sequence (line 71) was totally inhibited by the blocker. Its melting curve follows the same profile as a sample of no template control (not shown). The duplicates for each of the second variants of the target sequence fall exactly on one another. Different NT changes give different melting curves.

Example 4

Mismatched Second Primer with Hairpin Blocker as Part of a Lights-On/Lights-Off Probe Pair In this example, the use of a mismatched second primer (for non-symmetric PCR, the excess primer) is compared to use of a perfectly matched second primer. The amplification protocol was modified to utilize a primer-annealing temperature low enough for that primer to bind only after the first ten cycles of amplification. Consequently, in the first ten amplification cycles, only the first primer (the primer that overlaps the primer-binding hairpin oligonucleotide) was extended, and the second variant of the target sequence was copied linearly.

The first target sequence variant as was used in Examples 2 and 3. The second variant of the target sequence was the same as used in Example 3 (it did not contain the nucleotide change that was utilized for detection by a molecular beacon probe). The limiting primer and the perfectly complementary excess primer were also the same as used in Example 3. The primer-blocking hairpin oligonucleotide had the same nucleotide (NT) sequence as blocker B62, used in those examples, but its labeling was changed: whereas blocker B62 had a 5' Cal Orange and a 3' Dabcyl, the blocker used here had no 5' label and a 3' Black Hole Quencher 2.

For signal generation Lights-On/Lights-Off probe combination was utilized, with the primer-blocking hairpin oligonucleotide (labeled with 3' terminal Black Hole Quencher 2 non-fluorescent quenching moiety) as the "Off" probe. For a "On" probe, a short-stem molecular beacon probe was used with a 5' fluorophore (Quasar 670) and a 3' quencher (Black Hole Quencher 2) that hybridized to the target sequence immediately downstream from the primer-blocking hairpin oligonucleotide such that, when both hybridized to the target sequence, the quencher of the primer-blocking hairpin oligonucleotide interacted with (quenched) fluorescence from the 5' terminal fluorophore of the "On" probe. The "On" probe had a higher Tm against the target sequence. Sequences of the oligonucleotides are given below. For the blocker, the 18 nucleotides that were complementary to the perfectly complementary first variant of the target sequence are underlined, and the stem-forming terminal nucleotides are bolded. For the target sequence variants, one strand sequence is given, namely, the strand to which the limiting primer and primer-blocking hairpin oligonucleotide are complementary. In the target sequences the nucleotides that differ in the blocker-binding site are underlined. For the mismatched excess primer, the mismatched nucleotide is underlined. For the "On" probe, the stem-forming terminal nucleotides are bolded.

```
Blocker, modified B62:
                                              (SEQ ID NO. 2)
5'CGCCGCCTACGCCACCAGCTCCGGCG-BHQ2 3'

Limiting Primer:
                                              (SEQ ID NO. 9)
5'ACTCTTGCCTACGC 3'

Matched Excess Primer:
                                              (SEQ ID NO. 10)
5'GTGGAGTATTTGATAG 3'

Mismatched C-C Excess Primer:
                                              (SEQ ID NO. 20)
5'GTGGAGTATTTGATAC 3'

On-Probe:
                                              (SEQ ID NO. 21)
5'Quas670-AAAACTACCACAAGTTTATATTCAGTCATTTTCAGTT-
BHQ2 3'
```

First Variant of the Target Sequence:

```
                                              (SEQ ID NO. 12)
5'CTGGTGGAGTATTTGATAGTGTATTAACCTTATGTGTGACATGTTCTA
ATATAGTCACATTTTCATTATTTTTATTATAAGGCCTGCTGAAAATGACT
GAATATAAACTTGTGGTAGTTGGAGCTGGTGGCGTAGGCAAGAGTGC 3'
```

Second Variant of the Target Sequence:

(SEQ ID NO. 14)
5'CTGGTGGAGTATTTGATAGTGTATTAACCTTATGTGTGACATGTTCTA

ATATAGTCACATTTTCATTATTTTTATTATAAGGCCTGCTGAAAATGACT

GAATATAAACTTGTGGTAGTTGGAGCTGATGGCGTAGGCAAGAGTGC 3'

LATE-PCR amplifications were carried out in 25 ul volume consisting of 1×PCR buffer (Invitrogen, Carlsbad, Calif.), 3 mM $MgCl_2$, 200 nM dNTPs, 50 nM limiting primer, 1000 nM excess primer (either perfectly complementary or mismatched), 0.24×SYBR Green (Invitrogen, Carlsbad, Calif.), 500 nM blocker, 100 nM "On" probe, 1 unit of Platinum Taq DNA polymerase (Invitrogen, Carlsbad, Calif.) with 10,000 copies of first target sequence variant, with 10 copies of second target sequence variant, or with mixtures containing 10,000 copies of the first target sequence variant and none, one, ten, one-hundred or one-thousand copies of the second target sequence variant. Additionally, an assay was run without any target (a no-template control). Assays using the perfectly matched excess primer and the mismatched excess primer were run in parallel.

The thermal profile conditions for these reactions were as follows: 95° C. for 3 min; 10 cycles of 95° C./10 s, 60° C./2 min, 50° C./10 s, 72° C./20 s; 1 cycle of 95° C./10 s; 5 cycles of 60° C./2 min and 40° C./30 s; 1 cycle of 72° C./2 min; 50 cycles of 95° C./10 s, 50° C./10 s, 72° C./30 s (with SYBR signal reading); followed by a 10 min soak at 30° C., then a melt starting at 30° C. with 1° C. increments at 30 s intervals to 90° C. Samples are run in duplicate. The first segment of the profile (95° C. for 3 min) was to denature the antibody on Planimium Taq and activate the polymerase. The next segment (10 cycles at 95° C./60° C./50° C./72° C.) was to linearly amplify the second variant while suppressing amplification of the first variant with blocker B62 (modified). The next three segments (95° C., five cycles of 60° C./40° C. followed by 72° C.) were in combination a single amplification cycle to bind and extend the mismatched excess primer, the 60° C./40° C. cycling within that amplification cycle being used to improve that process (during this cycling within a cycle, the blocker stays on the first target sequence variant). The following 50 cycles, the final amplification cycles, at 95° C./50° C./72° C. were conventional LATE-PCR cycles utilizing both primers to produce double-stranded amplicons and then single-stranded amplicons from the second variant of the target sequence. The soak at 30° C. following amplification but before melting is to hybridize blocker B62 (modified) and the On probe both to single-stranded amplicons of the first and second target sequence variants for the purpose of detection during melting.

FIG. 9 shows the real-time SYBR signals as a function of cycle number during the final fifty amplification cycles. Curves 901 are the perfectly matched excess primer starting with 10,000 copies of the first variant of the target sequence. Curves 902 are the perfectly matched excess primer starting with 10 copies of second variant of the target sequence. Curves 903 are the mismatched excess primer starting with 10,000 copies of the first variant of the target sequence. Curves 904 are the mismatched excess primer starting with 10 copies of the second variant of the target sequence. As can be seen from FIG. 9, the amplification of the first target sequence variant is totally inhibited. No SYBR signal was detected.

FIG. 10 shows the Quasar 670 melting curve (derivative of fluorescence intensities) of the samples having 10,000 the first target sequence variant with or without the second target sequence variant of 1 to 1000 copies, plus the no-template control (NTC). Curves 1001 are the NTC; curves 1002 are 10,000 copies of the first target sequence variant; curves 1003 are 10,000 copies of the first target sequence variant with 1000 copies of the second target sequence variant; curves 1004 are 10,000 copies of the first target sequence variant with 100 copies of the second target sequence variant; curves 1005 are 10,000 copies of the first target sequence variant with 10 copies of the second target sequence variant; and curves 1006 are 10,000 copies of the first target sequence variant with 1 copy of the second target sequence variant.

The peaks at about 67° C. are due to the binding of the "On" probe, and the valleys at about 59° C. are due to the binding of the off-probe, here the primer-blocking hairpin hairpin oligonucleotide. As you can see, the position of the peaks and the valleys are the same for all the samples while the heights are different, indicating amplicons having the same sequence but differing in amount.

The amplification products from the amplification of mixtures were sequenced. The Sanger sequencing results from the samples containing 10,000 copies of the first variant of the target sequence and different numbers of copies (1, 10, 100, 1000) of the second variant of the target sequence all had the sequence of the second target sequence variant, including in the blocker-binding site and including particularly in the binding site of the "On" probe (data not shown).

Different mismatched excess primers have been tested in the assay of this example. The sequences of the perfectly complementary excess primer, the mismatched excess primer used above, and the several other mismatched excess primers are set forth below. The mismatched nucleotide is underlined in each case.

```
Matched Excess Primer:
                                (SEQ ID NO. 10)
5'GTGGAGTATTTGATAG 3'

Mismatched C-C Excess Primer:
                                (SEQ ID NO. 20)
5'GTGGAGTATTTGATAC 3'

Mismatched Excess Primer XP1A:
                                (SEQ ID NO. 22)
5'GTGGAGTATTTGATAA3'

Mismatched Excess Primer XP1T:
                                (SEQ ID NO. 23)
5'GTGGAGTATTTGATAT3'

Mismatched Excess Primer XP2T:
                                (SEQ ID NO. 24)
5'GTGGAGTATTTGATTG3'

Mismatched Excess Primer XP2C:
                                (SEQ ID NO. 25)
5'GTGGAGTATTTGATCG3'

Mismatched Excess Primer XP3A:
                                (SEQ ID NO. 26)
5'GTGGAGTATTTGAAAG3'

Mismatched Excess Primer XP3G:
                                (SEQ ID NO. 27)
5'GTGGAGTATTTGAGAG3'
```

Figure 11:
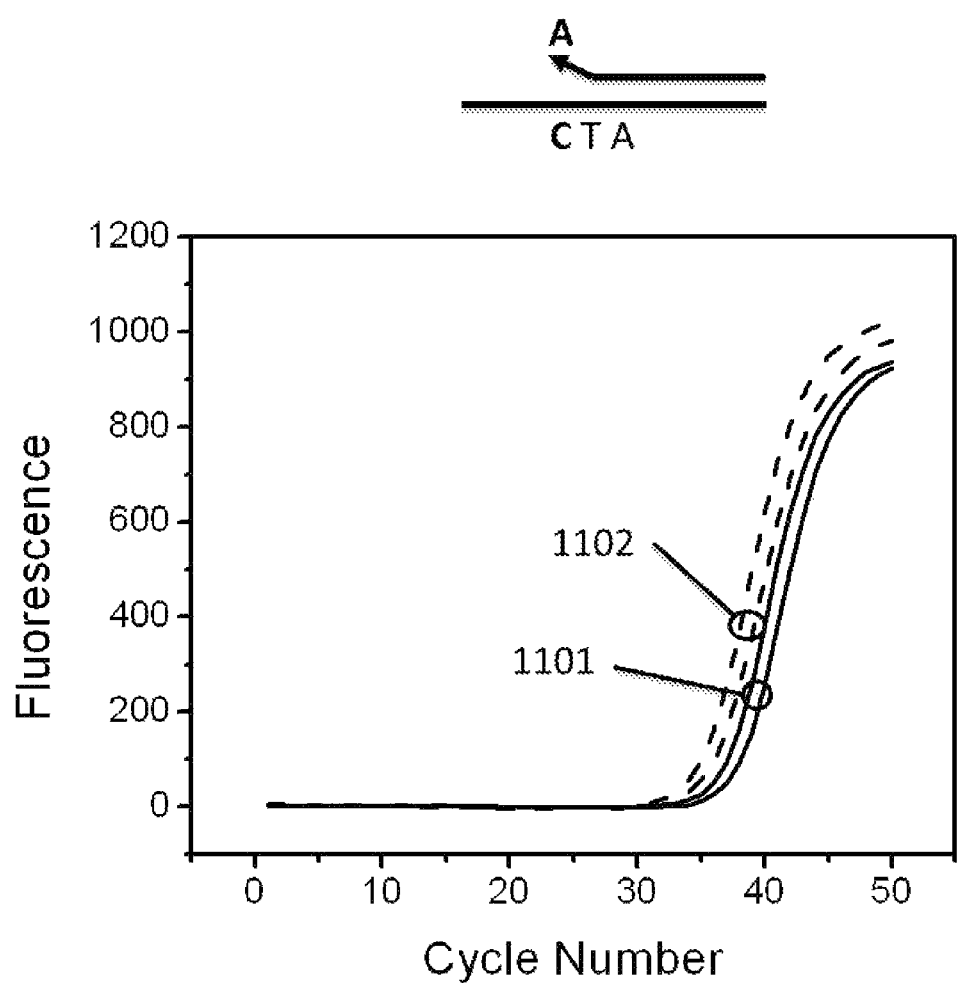
FIGS. 11-16 are real-time SYBR fluorescence readings during LATE-PCR amplifications described in Example 4 using mismatched second primer candidates with first and second target variants.
Figure 12:
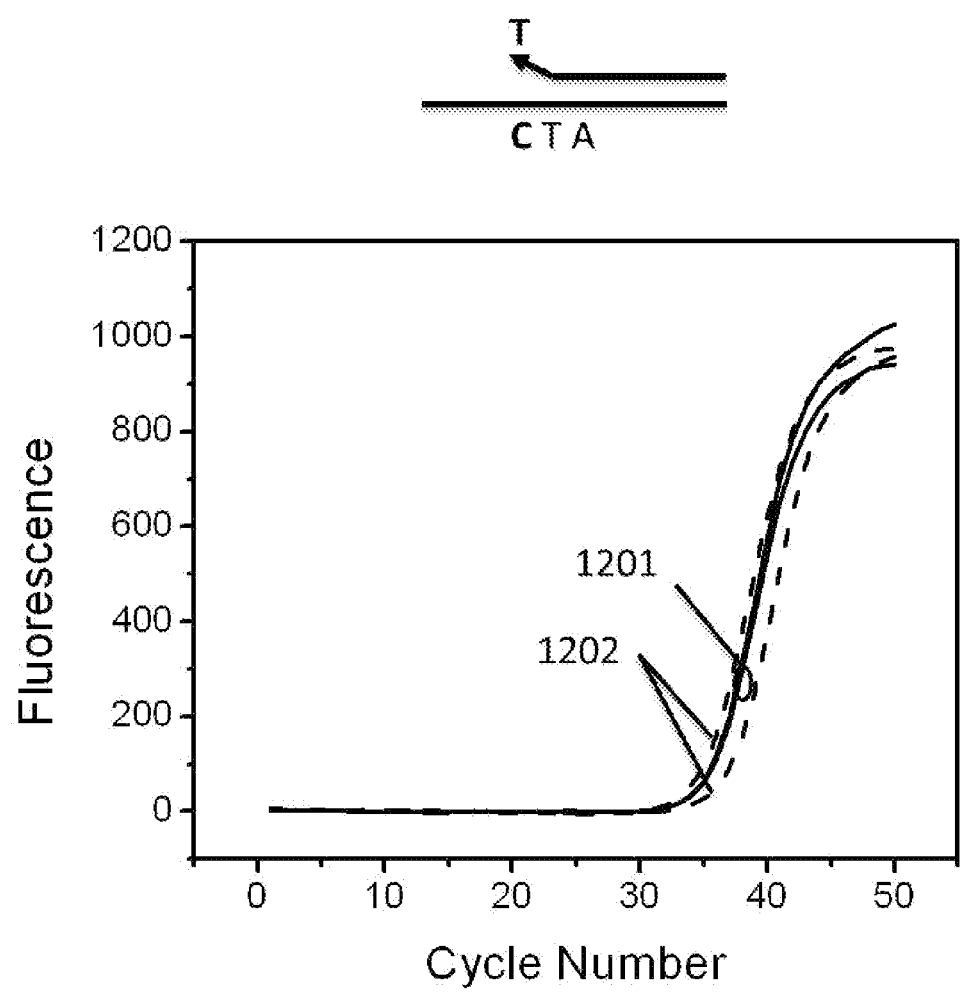
Figure 13:
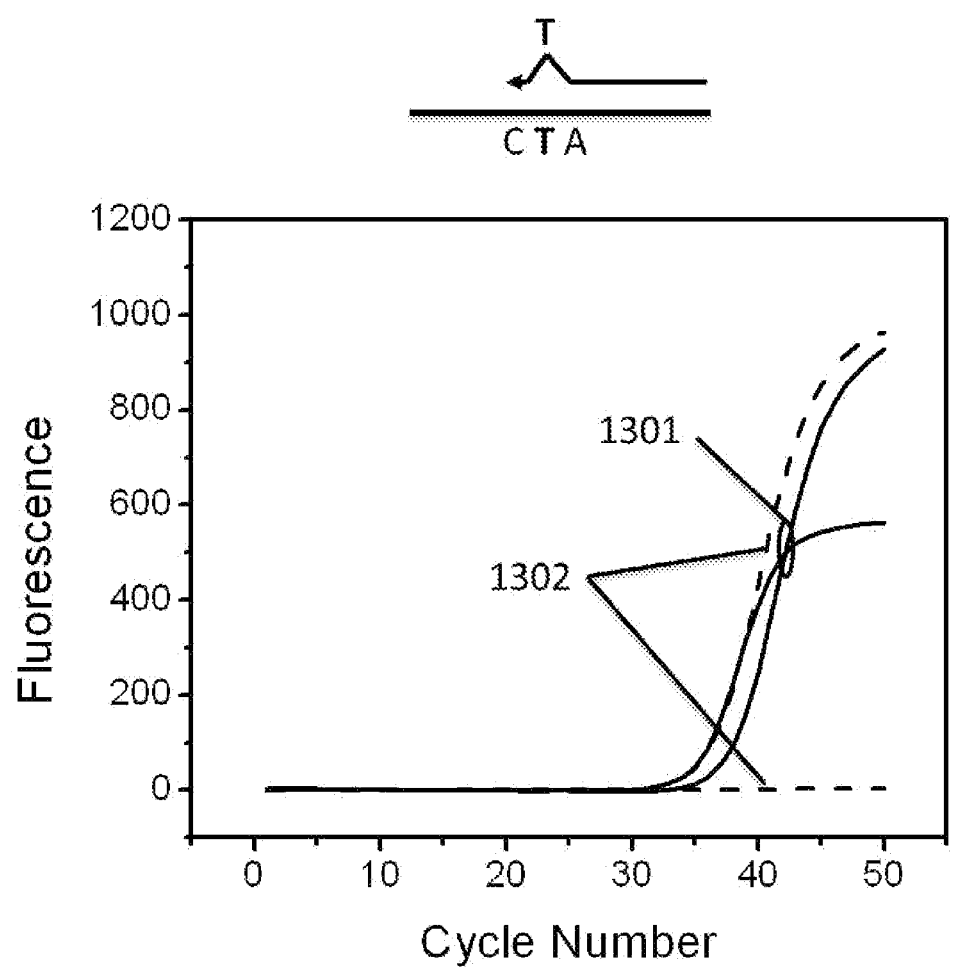
Figure 14:
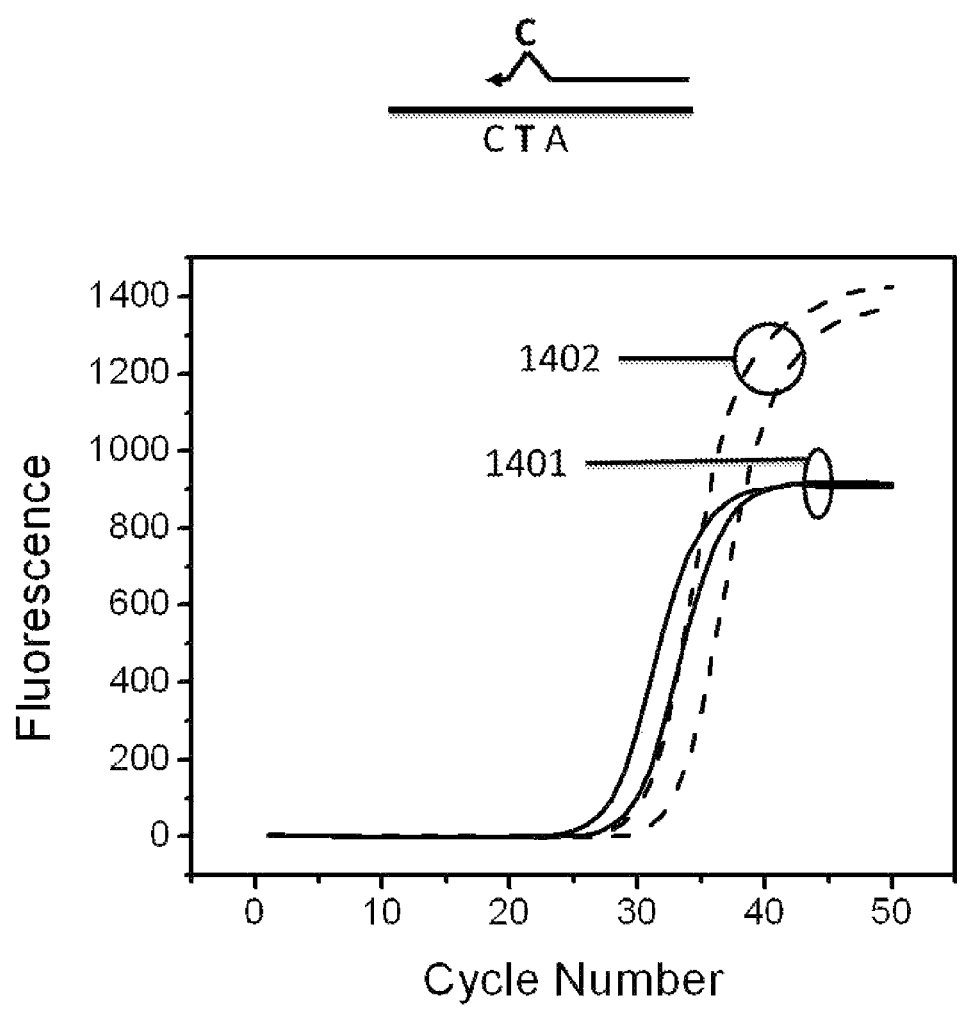
Figure 15:
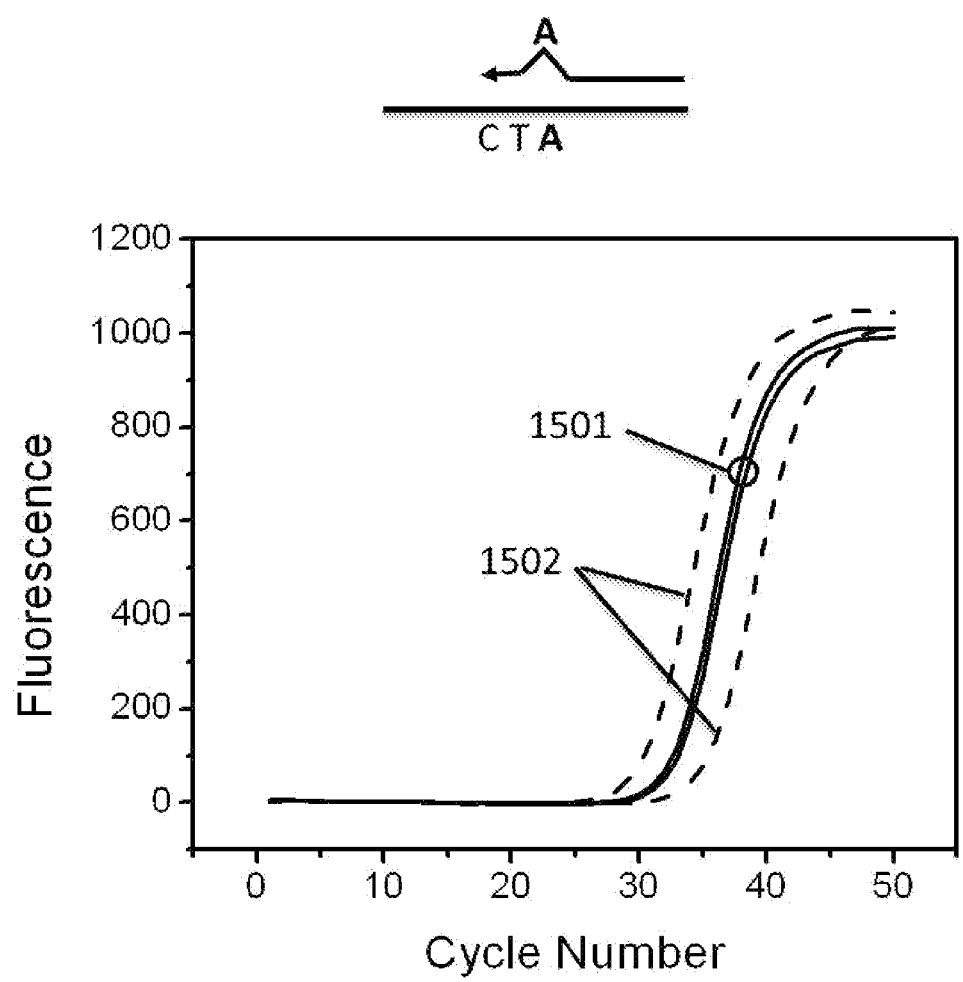
Figure 16:
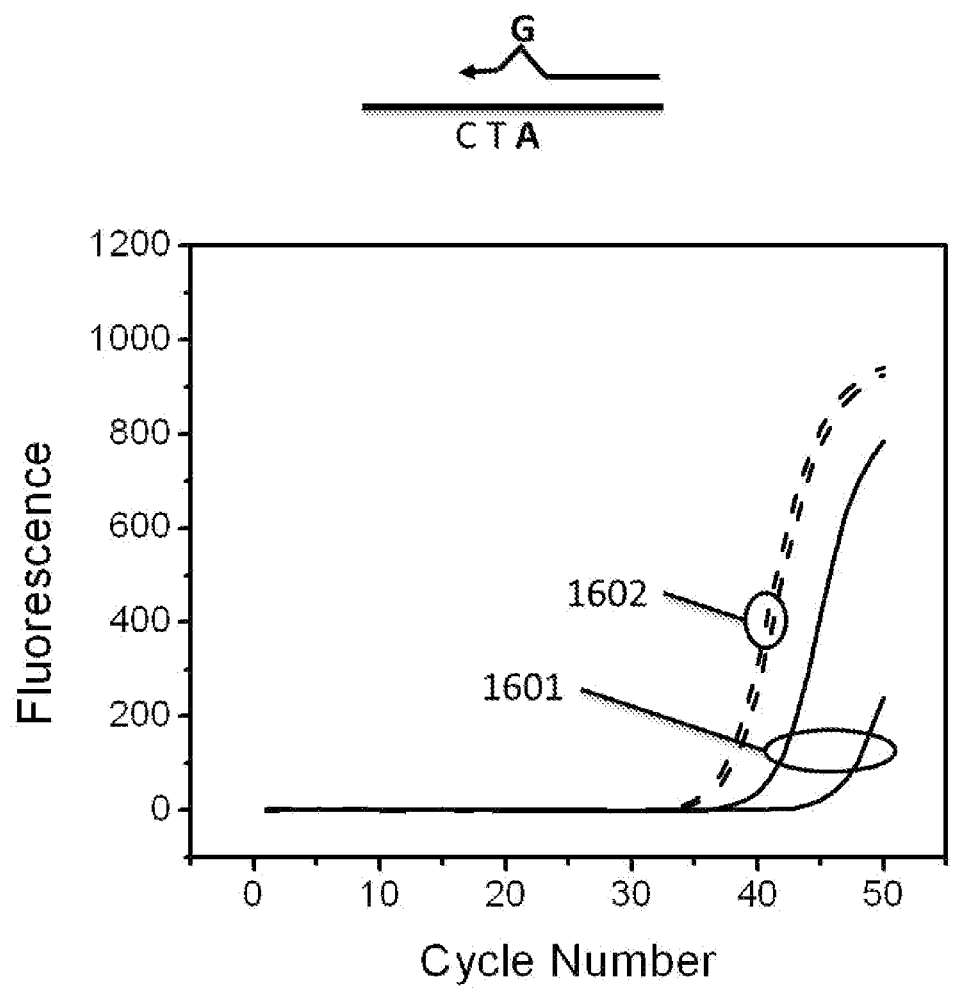

As discussed above, FIG. 9 includes circle 903, the real-time amplification curves (SYBR fluorescence versus cycle number) for 10,000 copies of the first target sequence variant using the mismatched C-C excess primer, and circle 904, the curves for 10 copies of the second variant of the target sequence with that primer. FIGS. 11-16 present the same information for other mismatched excess primer. In FIG. 11, circle 1101 is the real-time amplification curves for 10,000 copies of the first target sequence variant using the mismatched excess primer XP1A, and circle 1102 is the curves for 10 copies of the second variant of the target sequence with that primer. In FIG. 12, circle 1201 is the real-time amplification curves for 10,000 copies of the first variant of the target sequence using the mismatched excess primer XP1T, and circle 1202 is the curves for 10 copies of the second variant of the target sequence using that primer. In FIG. 13, circle 1301 is the real-time amplification curves for 10,000 copies of the first variant of the target sequence using the mismatched excess primer XP2T, and circle 1302 is the curves for 10 copies of the second variant of the target sequence using that primer. In FIG. 14, circle 1401 is the real-time amplification curves for 10,000 copies of the first variant of the target sequence using the mismatched excess primer XP2C, and circle 1402 is the curves for 10 copies of the second variant of the target sequence using that primer. In FIG. 15, circle 1501 is the real-time amplification curves for 10,000 copies of the first variant of the target sequence using the mismatched excess primer XP3A, and circle 1502 is the curves for 10 copies of the second variant of the target sequence using that primer. In FIG. 16, circle 1601 is the real-time amplification curves for 10,000 copies of the first variant of the target sequence using the mismatched excess primer XP3G, and circle 1602 is the curves for 10 copies of the second variant of the target sequence using that primer. For this target amplification, it was judged as acceptable any mismatched excess primer for which the curves for 10 copies of the second variant of the target sequence came up ($C_T$) earlier than the curves for 10,000 copies of the first variant of the target sequence, namely Mismatched C-C Excess Primer (FIG. 9) and Mismatched Excess Primer XP3G (FIG. 16).

Example 5

Detection of Rare Point Mutations in Genomic DNA Using a Hairpin Blocker as Part of a Lights-On/Lights-Off Probe Pair This example demonstrates an assay according to this invention to detect rare mutations (rare second variants) in a background of genomic DNA (abundant first variant) to which artifactual cross hybridization might occur. In the present example detection of rare point mutations was demonstrated using genomic DNA prepared from several cell lines and a hairpin blocker that also served as a Lights-Off probe in a Lights-On/Lights-Off probe pair.

a. Investigation of DNA Polymerase Error

As shown in Example 2, a weak signal was observed when 1,000,000 copies of the first sequence, here the "pure" wild type target, were used as the template. Mere appearance of SYBR signal does not establish whether this signal is due to: a) a binding error of the blocker; b) trace contamination of the pure wild type with a non-wild type sequence; c) Taq error. In order to examine these possibilities, plasmid DNA of the wild-type sequence was further amplified in a series of parallel reactions and then sequenced the excess primer strand of each amplified product that gave a SYBR signal. The oligonucleotides used were as follows:

```
Limiting Primer:
                                          (SEQ ID NO. 9)
  5'ACTCTTGCCTACGC 3'

Excess Primer:
                                          (SEQ ID NO. 10)
  5'GTGGAGTATTTGATAG 3'

Blocker, Off-probe:
                                          (SEQ ID NO. 2)
  5'CGCCGCCTACGCCACCAGCTCCGGCG-BHQ2 3'
```

Wild-Type Sequence of the Excess Primer Strand

```
                                          (SEQ ID NO. 12)
5'CTGGTGGAGTATTTGATAGTGTATTAACCTTATGTGTGACATGTTCTA

ATATAGTCACATTTTCATTATTTTTATTATAAGGCCTGCTGAAAATGACT

GAATATAAACTTGTGGTAGTTGGAGCTGGTGGCGTAGGCAAGAGTGC 3'
```

In the blocker/Off-probe, the nucleotides that are complementary to the target sequence are underlined, and the hairpin-forming complementary terminal nucleotides are bolded. In the target sequence, the six nucleotides of interest regarding mutant cell lines are underlined.

LATE-PCR amplifications were carried out in 25 µl volume consisting of 1×PCR buffer (Invitrogen, Carlsbad, Calif.), 3 mM $MgCl_2$, 200 nM dNTPs, 50 nM limiting primer, 1000 nM excess primer, 0.24×SYBR Green (Invitrogen, Carlsbad, Calif.), 500 nM blocker (Off-Probe), and 1 unit of Platinium Taq DNA polymerase (Invitrogen, Carlsbad, Calif.) with 1000 or 10,000 copies of plasmid DNA containing the target sequence.

The thermal profile conditions for these reactions included a two-minute blocker-binding step described in Example 2 and used in Example 3. The conditions were as follows: 95° C. for 3 min; 60 cycles of 95° C./10 s, 60° C./2 min, 50° C./10 s, 72° C./30 s; followed by a 10 min soak at 30° C., then a melt starting at 30° C. with 1° C. increments at 30 s intervals to 90° C.

Fifteen samples that give a SYBR Green signal were diluted 12 times in $H_2O$ and were then sent to a commercial company for dideoxy sequencing. The sequencing results were compared with the target sequence, which is the wild-type DNA before PCR. All the sequenced products had at least one mutation (one sample had two mutations), and all the mutations were in the blocker-binding region (data not shown). One third of the sequenced products had a mutation outside of the region (GGTGGC) where mutations occurred in the mutant cell lines. Also, thirteen of the sixteen mutations that were found were the incorrect insertion of an A nucleotide, This is significant in light of the fact that Taq polymerase is known to insert As at the end of extensions. Taken together these observations strongly suggest that the unexpected sequence changes were due to Taq polymerase errors.

b. Preparation of Genomic DNA from Cell Lines

Cell lines are obtained from American Type Culture Collection (ATCC) (Manassas, Va.). Four cell lines were used in this experiment (K562, SW1116, CAPAN 2 and PL 45) to provide the wild-type allele (K562) and different mutant alleles. The actual mutation and the genotype in each cell line were confirmed by Dilute-'N'-Go sequencing (Rice et al. (2007) Nature Protocols 2(10): 2429-2438; and Jia et al. (2010) Nucl. Acids Res. 38(11): e119) after PCR without selective amplification.

Cells (about $7.5\times10^5$) were washed twice by centrifugation in $Mg^{2+}$ free PBS and then suspended in 100 µl volume. 5 µl of the cell suspensions were added into 32.5 µl of Quantilyse (see, "QuantiLyse™: Reliable DNA amplification front single cells, Pierce K E; Rice J E; Sanchez J A; et al., BIO-TECHNIQUES, 32(5), 1106-1111, 2002.), which contained 10 mM Tris-CL pH 8.3 buffer, 5 µM SDS and 0.1 mg/ml proteinase K, followed by incubation at 50° C. for 120 min, then at 95° C. for 15 min. When the cells from a cell line were lysed in more than one tube, all tubes were pooled together after lysis. Aliquotes of 20 µl were then stored at −20° C. until needed. The number of genomes was therefore the same for every aliquot.

The treatment described above digests all proteins bound to the DNA but does not purify the genomic DNA away from the digestion products. The concentration of genomic DNA in each frozen aliquot from each cell lines was determined by serial dilution PCR using the following primers:

```
                                             (SEQ ID NO. 28)
        Limiting Primer: 5'CACTCTTGCCTACG 3'

(SEQ ID NO. 10)
        Excess Primer: 5'GTGGAGTATTTGATAG 3'
```

The excess primer was the perfectly matched excess primer used in Example 4. The limiting primer used here was modified from the limiting primer used in Examples 3 and 4 by addition of one nucleotide, a C, on the 5' end and by deletion of a nucleotide, a C, at the 3' end. This modified limiting primer does not detect possible mutations occurring in KRas Gene at both Codon 12 and Codon 13, which are relevant to cancers.

PCR amplifications were carried out in 25 µl volume consisting of 1×PCR buffer (Invitrogen, Carlsbad, Calif.), 3 mM MgCl$_2$, 200 nM dNTPs, 50 nM limiting primer, 1000 nM excess primer, 0.24×SYBR Green (Invitrogen, Carlsbad, Calif.), 1 unit of Platinum Taq DNA polymerase (Invitrogen, Carlsbad, Calif.), plus a specific dilution of genomic DNA prepared from each cell line. No blocker was added to this PCR amplification. Therefore all DNA variants were amplified with the same efficiency.

The thermal profile conditions for these reactions were the same as those in Example 3 except for the number of cycles. The conditions were as follows: 95° C. for 3 min; 50 cycles of 95° C./10 s, 50° C./10 s, 72° C./20 s; followed by a 10 min pause at 30° C., then a melt starting at 30° C. with 1° C. increments at 30 s intervals to 90° C. All samples were run in duplicate. The highest dilution to generate a recognizable SYBR Green signal was deemed to contain a single genome and the concentration of each original stock was determined based on the extent of dilution required to reach that single-genome concentration.

c. Determination of Mutations in Each Cell Line

The mutation present in each cell line was determined by the Dilute-'N'-Go sequencing (see, "Monoplex/multiplex linear-after-the-exponential-PCR assays combined with PrimeSafe and Dilute-'N'-Go sequencing," Rice, John E.; Sanchez, J. Aquiles; Pierce, Kenneth E.; et al., NATURE PROTOCOLS, 2(10), 2429-2438, 2007: and Dilute-'N'-Go dideoxy sequencing of all DNA strands generated in multiplex LATE-PCR assays," Jia Yanwei; Osborne Adam; Rice John E.; et al., NUCLEIC ACIDS RESEARCH, 38(11), e119, 2010) by taking 1 µl of the PCR product from each amplification and diluting it with 11 µl H$_2$O. The samples were sent to a commercial sequencing company for dideoxy sequencing. Based on this sequence information one cell line was found to by homozygous for the GGT allele (cell line K562, considered "wild type"), two were found to be 50:50 heterozygous for the GGT allele and either the GAT allele or the GCT allele, and one was found to be an unequal mixture of two sequences, the GGT allele and the GTT allele, as shown below with bold underlining:

K562 Target Sequence—Homozygous: 100% GGT Allele

```
                                             (SEQ ID NO. 12)
5'CTGGTGGAGTATTTGATAGTGTATTAACCTTATGTGTGACATGTTCTA

ATATAGTCACATTTTCATTATTTTTATTATAAGGCCTGCTGAAAATGACT

GAATATAAACTTGTGGTAGTTGGAGCTGGTGGCGTAGGCAAGAGTGC 3'
```

PL45 Target Sequence—50:50 Heterozygous: 50% SEQ ID NO. 12 and 50% GAT Allele:

```
                                             (SEQ ID NO. 14)
5'CTGGTGGAGTATTTGATAGTGTATTAACCTTATGTGTGACATGTTCTA

ATATAGTCACATTTTCATTATTTTTATTATAAGGCCTGCTGAAAATGACT

GAATATAAACTTGTGGTAGTTGGAGCTGATGGCGTAGGCAAGAGTGC 3'
```

CAPAN 2 Target Sequence—10:90 Mixture: 90% SEQ ID NO. 12 and 10% GTT Allele:

```
                                             (SEQ ID NO. 15)
5'CTGGTGGAGTATTTGATAGTGTATTAACCTTATGTGTGACATGTTCTA

ATATAGTCACATTTTCATTATTTTTATTATAAGGCCTGCTGAAAATGACT

GAATATAAACTTGTGGTAGTTGGAGCTGTTGGCGTAGGCAAGAGTGC 3'
```

SW1116 Target Sequence—50:50 Heterozygous: 50% SEQ ID NO. 12 and 50% GCT Allele:

```
                                             (SEQ ID NO. 16)
5'CTGGTGGAGTATTTGATAGTGTATTAACCTTATGTGTGACATGTTCTA

ATATAGTCACATTTTCATTATTTTTATTATAAGGCCTGCTGAAAATGACT

GAATATAAACTTGTGGTAGTTGGAGCTGCTGGCGTAGGCAAGAGTGC 3'
```

Cell line K562 was homozygous for the GGT allele and was considered to be the wild type for the purpose of detecting rare amounts of other alleles (mutants). The other cell lines contain more than one allele. In PL45, there is about 50% GAT allele and 50% GGT allele. In CAPAN 2, there is less than 10% GTT allele and more than 90% GGT allele. In SW1116, there is about 50% GCT allele and 50% GGT allele.

d. Selective Amplification in Mixtures of Different Cell Lines

LATE-PCR amplifications were run with a Lights-On/Lights-Off probe pair. The Lights-On/Lights-Off probe pair was the same pair as used in Example 4. The Lights-Off probe also served as a primer-blocking hairpin oligonucleotide ("hairpin blocker") with a stem of 5 nucleotides (bolded) and an internal sequence of 18 nucleotides that were perfectly complementary to the sequence of cell line K562. The Lights-On probe had a stem of 2 nucleotides (bolded).

```
Limiting Primer:
                                             (SEQ ID NO. 28)
5'CACTCTTGCCTACG 3'

Excess Primer:
                                             (SEQ ID NO. 10)
5'GTGGAGTATTTGATAG 3'
```

-continued

Blocker, Off-probe:
(SEQ ID NO. 2)
5' CGCCGCCTACGCCACCAGCTCCGGCG-BHQ2 3'

On-Probe:
(SEQ ID NO. 21)
5'Quas670-AAAACTACCACAAGTTTATATTCAGTCATTTTCAGTT-BHQ2 3'

PCR amplifications were carried out in 25 μl volume. Reaction mixtures contained 1×PCR buffer (Invitrogen, Carlsbad, Calif.), 3 mM MgCl$_2$, 200 nM dNTPs, 50 nM limiting primer, 1000 nM excess primer, 0.24×SYBR Green (Invitrogen, Carlsbad, Calif.), 500 nM blocker (Off-Probe), 100 nM On-Probe and 1 unit of Platinium Taq DNA polymerase (Invitrogen, Carlsbad, Calif.). Reaction mixtures also contained either different concentrations of genomic DNA purified from each cell line or mixtures of 10,000 copies of DNA from cell line K562 and amounts of DNA from one of the other cell lines with a copy number ranging from 1000 copies to 1 copy.

The thermal profile conditions for these reactions were similar to those of Example 3. (They did not include the profile modifications in Example 4 for use with a mismatched excess primer.) The conditions were as follows: 95° C. for 3 min; 60 cycles of 95° C./10 s, 60° C./2 min, 50° C./10 s, 72° C./30 s (with SYBR signal reading); followed by a 10 min soak at 30° C., then a melt starting at 30° C. with 1° C. increments at 30 s intervals to 90° C. Samples were run in duplicate. The fluorescent signature from the Lights-On/Lights-Off probe combination was monitored during melting and analyzed. Melt curves (first derivative of probes fluorescence intensity versus temperature) are presented in FIGS. 17-20.

Both the limiting primer and the excess primer were perfectly matched to all the alleles. Because it was concluded that Taq errors were occurring (see above), and Platinum Taq polymerase is known to make errors at a rate of about $10^{-4}$ errors per nucleotide addition, there would be, or at least could be, about 10 errors in the blocker binding region in the first cycle of amplification. These errors would be amplified, because the blocker would not block them in subsequent cycles. Because of these errors, a starting sample containing 10,000 copies of pure wild-type genome—from cell line K562 was expected to generate a positive fluorescence signature equivalent to 10 true mutation in 10,000 genomes. For this reason the signature of the DNA from 500 K562 diploid cells was considered as the limit for distinguishing a pre-existing mutation from Taq errors, and signals from the mixture samples with an On-peak lower than the On-peak signal in the pure K562 at 10,000 genomes were disregarded.

Figure 17:
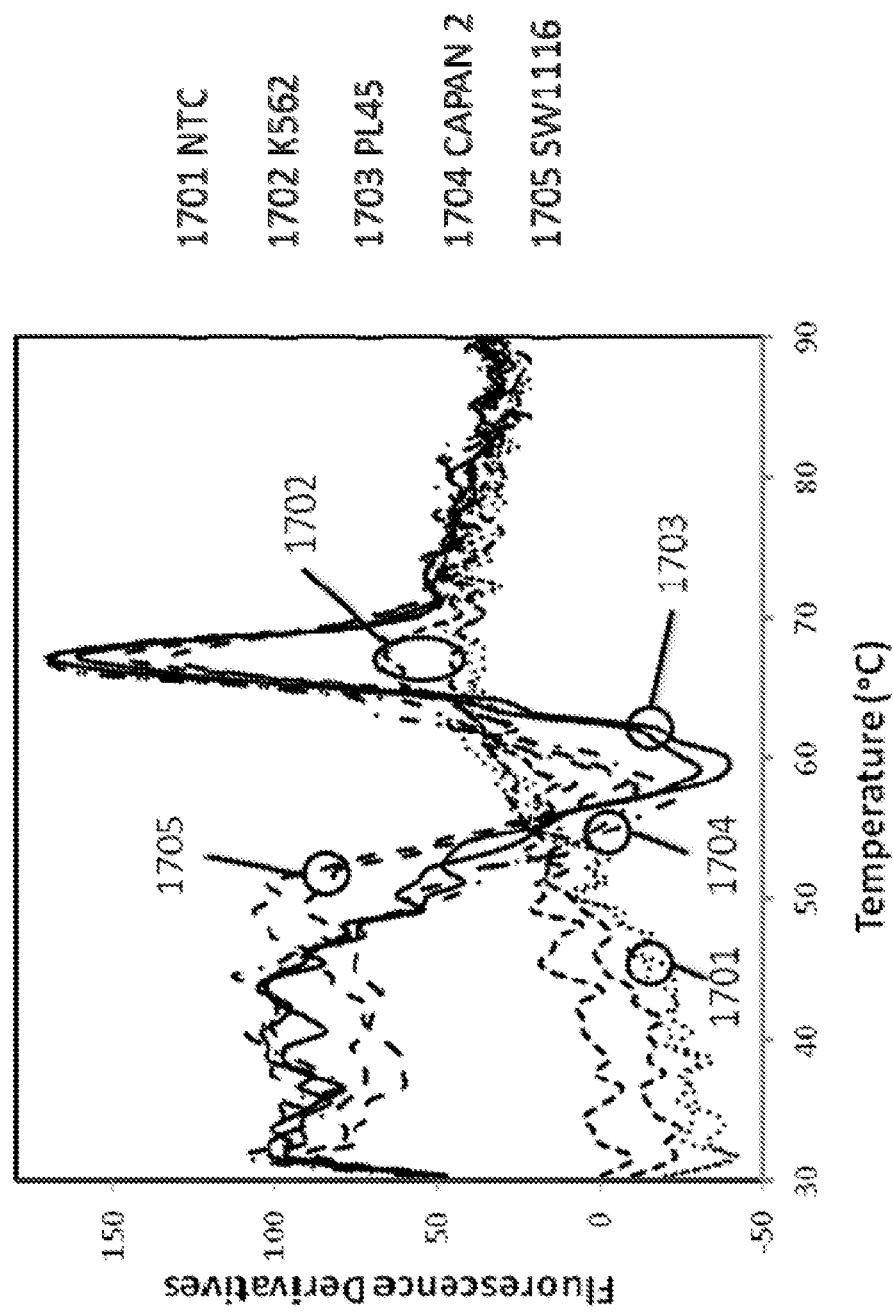
FIGS. 17-20 are melting curves following LATE-PCR amplifications of genomic DNA from various cell lines as described in Example 5.

FIG. 17 shows the Quasar 670 melting curves of the samples containing genomic DNA from the different cell lines, obtained as described above, plus a no-template control (NTC). Curves 1701 are the NTC; curves 1702 are amplifications starting with 10,000 copies of genomic DNA (10,000 genomes) from cell line K562; curves 1703 are amplifications starting with 1000 genomes of cell line PL45; curves 1704 are amplifications starting with 1000 genomes of cell line SW1116; and curves 1705 are amplifications starting with 1000 genomes of cell line CAPAN 2. As can be seen from FIG. 17, different alleles gave different melting curves (different "fluorescence signatures"), which were distinguishable from one another. In the Lights-On/Lights-Off probe design that was used, if the target is wild type, the Off-probe (Blocker) binds to the target at a higher temperature than does the On-probe, so that during melting the On-probe melts off first. Peaks at about 67° C. are due to the binding of the On-probe, and valleys at about 59° C. are due to the binding of the Off-probe. Were there perfect selectivity and no polymerase errors, amplification products from cell line K562 would have a negative fluorescence signature compared to the NTC because the quencher quenches more fluorescence when they are next to each other than they are randomly contacted in solution. As shown in FIG. 17, for 10,000 copies of DNA from K562, a small On-peak is detected at about 67° C., indicating binding of the On-probe. This was judged to be due to the artifactual mutations generated during amplification by Taq polymerase error.

Figure 18:
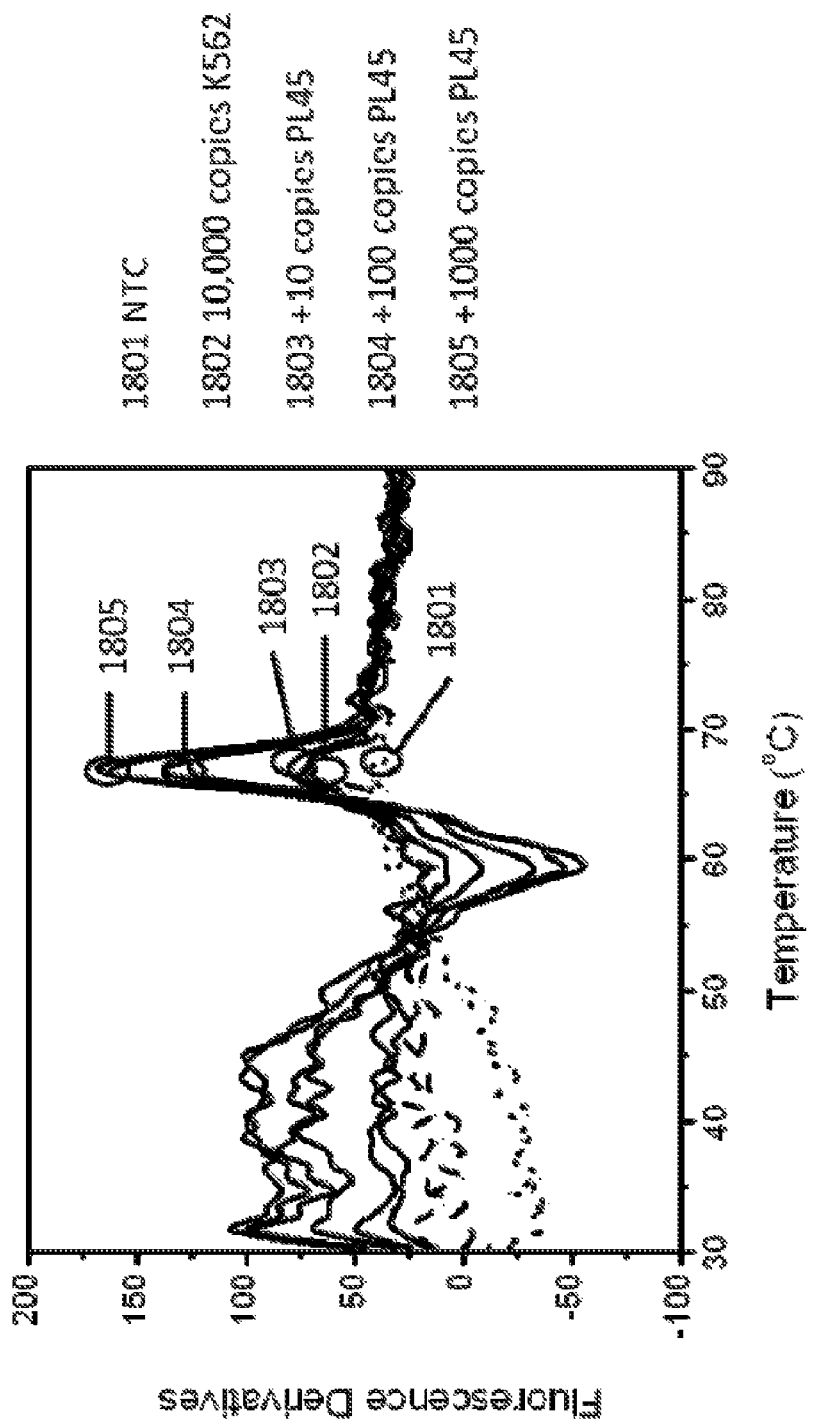

FIG. 18 shows the Lights-On/Lights-Off fluorescence derivatives of mixtures of 10,000 copies DNA from cell line K562 and different concentrations of DNA from cell line PL45. Curves 1801 are the NTC; curves 1802 are amplifications starting with 10,000 copies DNA from cell line K562; curves 1803 are amplifications starting with mixtures of 10,000 copies DNA from cell line K562 and 10 copies of DNA from cell line PL45; curves 1804 are amplifications starting with mixtures of 10,000 copies DNA from cell line K562 and 100 copies of DNA from cell line PL45; and curves 1805 are amplifications starting with mixtures of 10,000 copies DNA from cell line K562 and 1000 copies of DNA from cell line PL45.

Using pure K562 fluorescence signal as the threshold, it was decided to judge the result starting with another cell line or with a mixture as positive, rather than inconclusive, when its On-peak signal at about 67° C. is higher. Referring to FIG. 18, it was judged that the mixture of 10,000 copies of DNA from cell line K562 and 10 copies of DNA from cell line PL45 to be not distinguishable from 10,000 copies of DNA from K562 alone. However, it was judged that the mixtures containing 100 or 1000 copies of DNA from cell line PL45 were clearly distinguishable. Thus, the assay was able to detect as few as 100 copies of DNA from cell line PL45 with the background of 10,000 copies of DNA from cell line K562. Considering the heterozygosity of PL45, 50% of the DNA having the GAT allele while 50% has the same GGT allele as does cell line K562, the rare mutation detection sensitivity for the GAT mutation was actually 50 in 10,000, which translates to a detection sensitivity of 0.5%.

Figure 19:
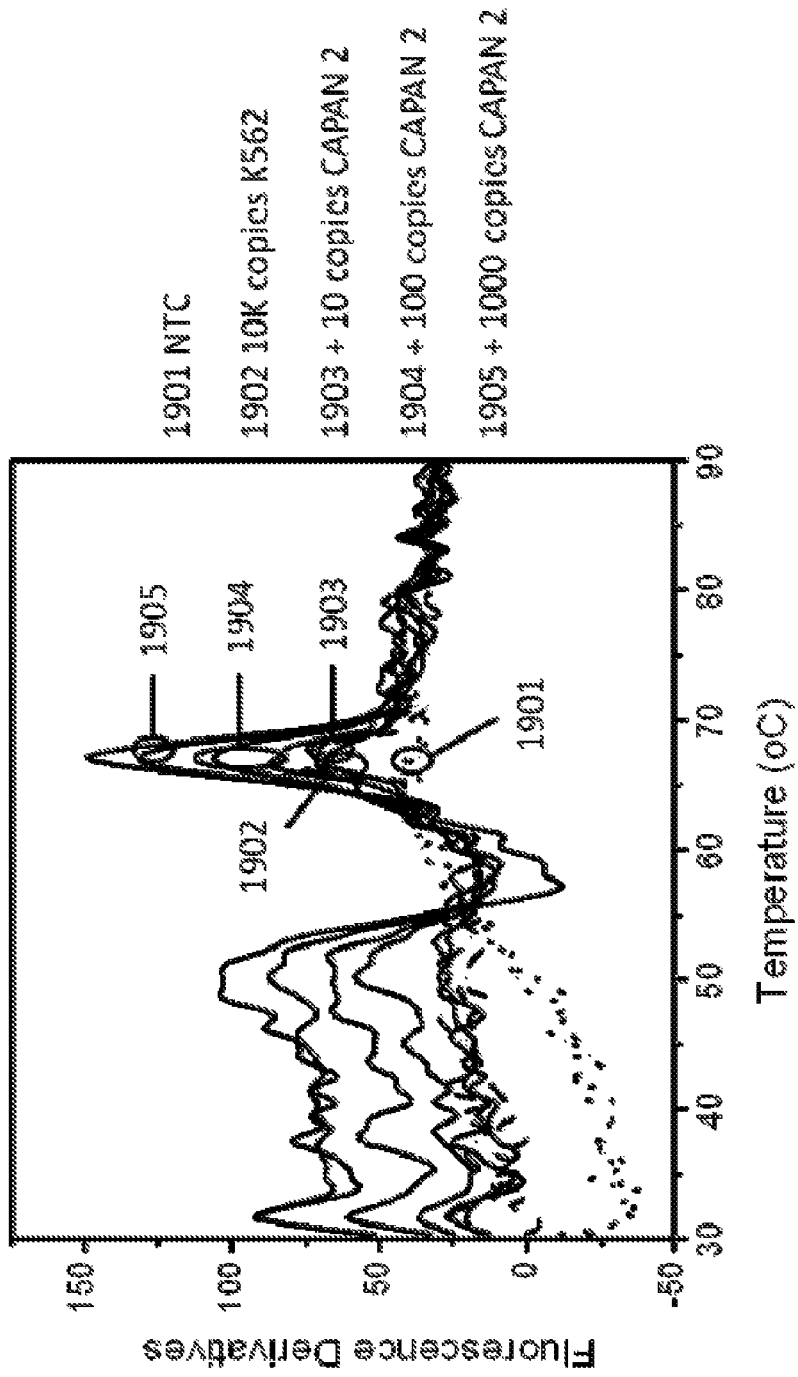

FIG. 19 shows the Lights-On/Lights-Off fluorescence derivatives of mixtures of 10,000 copies DNA from cell line K562 and different concentrations of DNA from cell line CAPAN 2. Curves 1801 are the NTC; curves 1802 are amplifications starting with 10,000 copies DNA from cell line K562; curves 1803 are amplifications starting with mixtures of 10,000 copies DNA from cell line K562 and 10 copies of DNA from cell line CAPAN 2; curves 1804 are amplifications starting with mixtures of 10,000 copies DNA from cell line K562 and 100 copies of DNA from cell line CAPAN 2; and curves 1805 are amplifications starting with mixtures of 10,000 copies DNA from cell line K562 and 1000 copies of DNA from cell line CAPAN 2. Applying the standard used for FIG. 18, 100 copies of rare allele were detected above the background signal established using 10,000 copies of wild-type cell line. Considering the heterozygosity in cell line CAPAN 2, which has 10% GTT mutation, the detection sensitivity by this measure reached 0.1% for GTT mutation, which is better than predicted from consideration of the Taq error rate.

Figure 20:
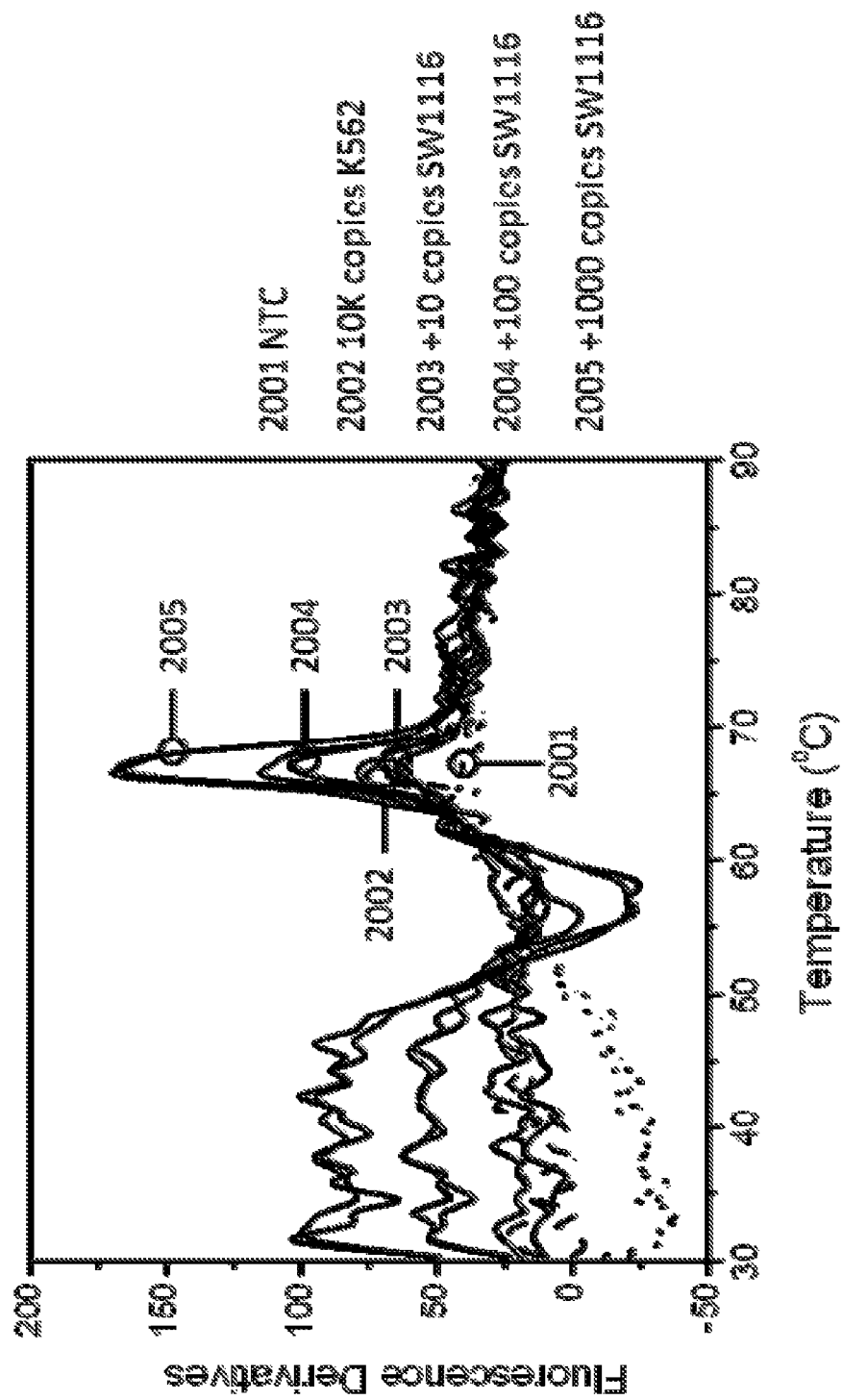

FIG. 20 shows the Lights-On/Lights-Off fluorescence derivatives of mixtures of 10,000 copies DNA from cell line K562 and different concentrations of DNA from cell line SW1116. Curves 1801 are the NTC; curves 1802 are amplifications starting with 10,000 copies DNA from cell line K562; curves 1803 are amplifications starting with mixtures of 10,000 copies DNA from cell line K562 and 10 copies of DNA from cell line SW1116; curves 1804 are amplifications starting with mixtures of 10,000 copies DNA from cell line K562 and 100 copies of DNA from cell line SW1116; and curves 1805 are amplifications starting with mixtures of 10,000 copies DNA from cell line K562 and 1000 copies of DNA from cell line SW1116. Applying the standard used for FIG. 18, 100 copies of the rare GCT allele were detected above the background signal established using 10,000 copies of wild-type cell line. Considering the heterozygosity in cell line SW1116, which has 50% GCT mutation, the detection sensitivity reached 0.5% for GCT mutation.

Example 6

Tailed Primer for Detection of Rare Point Mutations Using a Hairpin Blocker as Part of a Lights-On/Lights-Off Probe Pair This example describes the usage of a set of primers composed of a 3' linear segment, or "head", whose sequence matches to the target, and a 5' linear tail or 5' flip-tail, whose sequence does not match the target, together with the Lights-On/Lights-Off probe pair, where the Off-probe is a sequence-discriminating primer-blocking hairpin oligonucleotide (blocker), for detection of rare second variants of a target sequence containing point mutations. In this example the 3' head of the excess primer is perfectly complementary to the target sequence.

Figure 21:
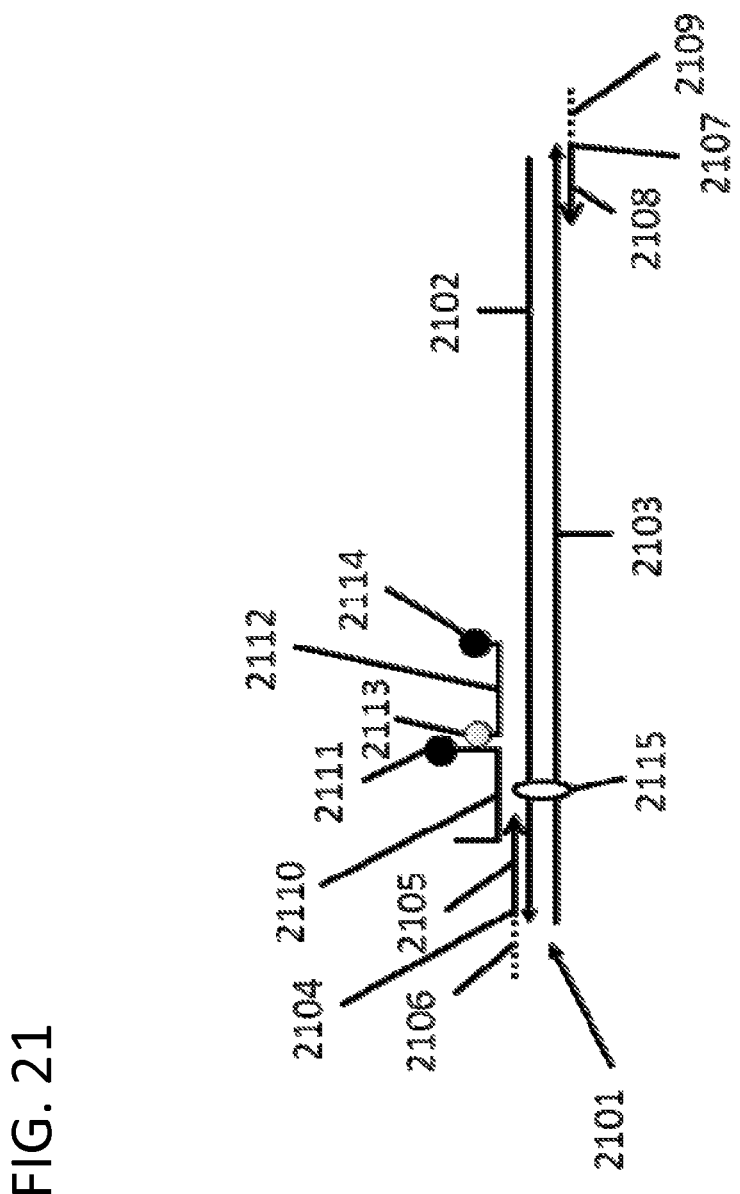
FIG. 21 is a schematic showing the hybridization, or binding, of a primer-blocking hairpin oligonucleotide that functions as an Off probe, an On probe, and tailed amplification primers to a first variant of a target sequence.

FIG. 21 shows the schematic design of the molecular components in this system. Limiting primer 2104 has a 3' head 2105 that is matched to the target 2101 on the strand 2102, and a 5' tail 2106, that is not matched to the target 2102. The 3' head of the limiting primer competes with the hairpin blocker 2110 that binds a sequence in target 2101 where a point mutation 2115 occurs. Here the hairpin blocker also functions as an Off-probe with a quencher 2111 at the 3' end, which hybridizes to the target adjacently to an On-probe 2112 with a fluorophore 2113 at the 5' end and a quencher 2114 at the 3' end. Excess primer 2107 also comprises a 3' head 2108, that is perfectly matched to the target 2101 on strand 2103, and a 5' tail 2109, which is not matched to target strand 2103.

As discussed in Example 5, Taq polymerase makes errors during PCR amplification, and once an error mutation in the blocker binding region is generated, it is selected and amplified in subsequent cycles in which the blocker is functional, thereby giving rise to a false positive signal when the wild-type concentration is 1000 molecules or higher. In the design described in the present example, only the mutant-type tailed strand gets amplified in the subsequent cycles, because only the mutant-type original sequence is utilized in the first cycle when the blocker blocks the wild type. Under these circumstances, even if Taq polymerase makes an error upon extension of the excess primer on the wild-type target, that error is not selected and amplified. Therefore, false positive mutants resulting from Taq errors are minimized.

The concentration-dependent Tm of the excess primer to the target at the start of the amplification reaction, $Tm^X_{[0]}$, is 10° C. lower than the concentration-dependent Tm of the limiting primer at the start of the reaction. $Tm^L_{[0]}$. A PCR protocol was run in which the first cycle includes a blocker-binding step, and the blocker binds selectively to the wild-type target. In that cycle, after the blocker-binding step, the 3' head of the limiting primer was annealed at a temperature that is too high for binding of the 3' head of the excess primer. Because the blocker blocks the binding of the limiting primer on the wild-type target, the limiting primer only binds to and extends on the mutant target in this cycle. The new strand synthesized by extension of the limiting primer (the limiting-primer-strand) necessarily includes the 5' tail of the limiting primer. In the second cycle the reaction was heated to separate the limiting-primer-strand from its template; then perform the blocker-binding step; then lower the temperature to an annealing temperature that permits binding and extension, not only of the limiting primer on the mutant, but also of the excess primer on the mutant-type limiting-primer-strand. The resulting strand (the excess-primer-strand) necessarily has the 5' tail of the excess primer and, upon full extension, has a 3' end that is complementary to the 5' tail of the limiting primer. Although in the second cycle the excess primer also binds and extends on the abundant wild-type target, from which Taq errors in the blocker-binding region could arise, its full extension does not have a 3' end that is complementary to the 5' tail of the limiting primer. The reaction mixture is then cycled many times at just two temperatures, a melting temperature and a primer-annealing/extension temperature. In these cycles, however, the primer-annealing/extension temperature is set at a temperature substantially higher than the temperature needed for binding of just the 3' head of the limiting primer. This temperature allows the full-length limiting primer and the full-length excess primer to bind to their complementary sequences on the excess-primer-strand and the limiting-primer-strand. The annealing temperature is a few degrees below the Tm of full length excess primer, $Tm^X_{[0]}$. Therefore, only the mutant-type rare second variant is amplified in these cycles.

An experiment was carried out using oligonucleotides having the sequences set forth below. In the sequence of the flip-tail first, limiting, primer, the complementary nucleotides that form the stem-loop structure are underlined, and the "neck" nucleotide is bolded. In the sequence of the linear-tail second, excess primer, the nucleotides of the 5' tail are bolded. In the On probe the stem-forming terminal nucleotides are bolded. In the blocker, the 18 nucleotides complementary to the first, wild-type variant of the target sequence are underlined, and the stem-forming terminal nucleotides are bolded.

Flip-tailed Limiting Primer:
(SEQ ID NO. 29)
5'<u>AGCGG</u>CACCA<u>CGCT</u>CCACTCTTGCCTACG- 3'

Linear-tailed Excess Primer:
(SEQ ID NO. 30)
5'CTCACCTTCCATCACCACGAGTATTTGATAG-3'

On-Probe:
(SEQ ID NO. 21)
5'Quas670-AAAACTACCACAAGTTTATATTCAGTCATTTTCAGTT-BHQ2 3'

Blocker/Off-Probe:
(SEQ ID NO. 2)
5'CGCCG<u>CCTACGCCACCAGCTCC</u>GGCG-BHQ2 3'

First Variant of the Target Sequence:

(SEQ ID NO. 12)
5'CTGGTGGAGTATTTGATAGTGTATTAACCTTATGTGTGACATGTTCTA

ATATAGTCACATTTTCATTATTTTTATTATAAGGCCTGCTGAAAATGACT

GAATATAAACTTGTGGTAGTTGGAGCTGGTGGCGTAGGCAAGAGTGC 3'

Second Variant of the Target Sequence:

(SEQ ID NO. 13)
5'CTGGTGGAGTATTTGATAGTGTATTAACCTTATGTGTCACATGTTCTA

ATATAGTCACATTTTCATTATTTTTATTATAAGGCCTGCTGAAAATGACT

GAATATAAACTTGTGGTAGTTGGAGCTGAT GGCGTAGGCAAGAGTGC 3'

LATE-PCR amplifications were carried out in 25 µl volume consisting of 1×PCR buffer (Invitrogen, Carlsbad, Calif.), 3 mM MgCl2, 200 nM dNTPs, 50 nM tailed limiting primer, 1000 nM tailed excess primer, 0.24×SYBR Green (Invitrogen, Carlsbad, Calif.), 500 nM blocker, 100 nM On-probe, 1 unit of Platinum Taq DNA polymerase (Invitrogen, Carlsbad, Calif.) with 10,000 copies of first variant (wild-type) or second variant (mutant), or with mixtures containing 10,000 copies of the first variant and 1, 10, 100 or 1000 copies of the second variant sequence. Additionally, an assay was run without any target; that is, a no-template control (NTC).

The thermal profile conditions for these reactions were as follows: 95° C. for 3 min; 1 cycle of 95° C./10 s, 60° C./2 min, 50° C./10 s, 72° C./30 s; 1 cycle of 95° C./10 s, 60° C./2 min and 40° C./30 s, 72° C./30 s; 60 cycles of 95° C./10 s, 70° C./30 s (with SYBR and Quasar 670 signal reading); followed by a 10 min soak at 30° C., then a melt starting at 30° C. with 1° C. increments at 30 s intervals to 95° C. Samples are run in duplicate.

The first segment of the profile (95° C. for 3 min) was to denature the antibody on Platinum Taq and activate the polymerase. The next segment (1 cycle at 95° C./60° C./50° C./72° C.) was to bind the blocker on first variant, bind the limiting primer on second variant, extend the limiting primer on second variant to make a limiting-primer-strand, while suppressing primer extension on first variant template with the blocker/Off-probe. The next segment (1 cycle of 95° C./10 s, 60° C./2 min and 40° C./30 s, 72° C./30) was to engage the tailed excess primer to generate an excess-primer-strand that contains the entire sequences (not just the 3' linear portion complementary to the target sequence) of both the tailed limiting primer and the tailed excess primer. The next segment (60 cycles at 95° C./72° C.) were two-step LATE-PCR cycles utilizing both full length primers to produce double-stranded amplification products, or amplicons, and then single-stranded amplicons containing the second variant plus incorporated tails. The soak at 30° C. following amplification but before melting was to hybridize the blocker/Off-Probe and the On probe both to single-stranded amplicons of first variant (if present) and second variant for the purpose of quantitative detection and identification of the product strands.

Figure 22:
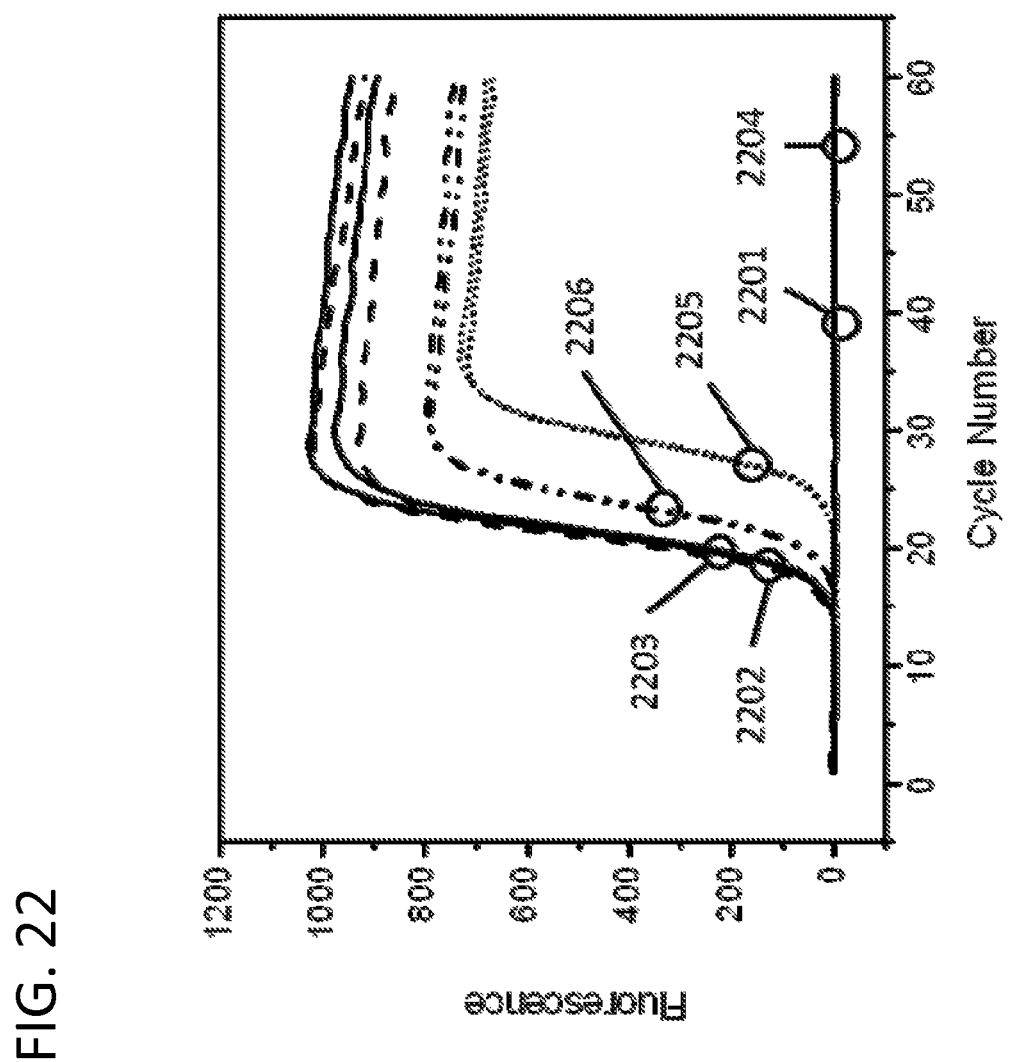
FIG. 22 is real-time SYBR fluorescence readings during LATE-PCR amplifications described in Example 6.

FIG. 22 shows the real time SYBR signal for samples of pure first variant or pure second variant in the presence or in the absence of the blocker. Curves 2201 are the no template controls in the absence of blocker; curves 2202 are 10,000 copies of the second variant in the absence of blocker; curves 2203 are 10,000 copies of the first variant in the absence of blocker; curves 2204 are the no template controls in the presence of blocker; curves 2205 are 10,000 copies of the second variant in the presence of blocker; curves 2206 are 10,000 copies of the first variant in the presence of blocker.

As can be seen in FIG. 22, in the absence of blocker the amplification of the first and second variants are equally efficient with the same Ct value. In the presence of the blocker, the amplification of the second variant was slightly suppressed, as reflected by a delay in the Ct of two cycles (a ∆Ct of 2), while the first variant was significantly more suppressed, as reflected by a ∆Ct of 8. This gives a ∆∆Ct of 6, which indicates that less than 2% of the first variant molecules were amplified as efficiently as the second variant molecules (2% of 10,000=200).

Figure 23:
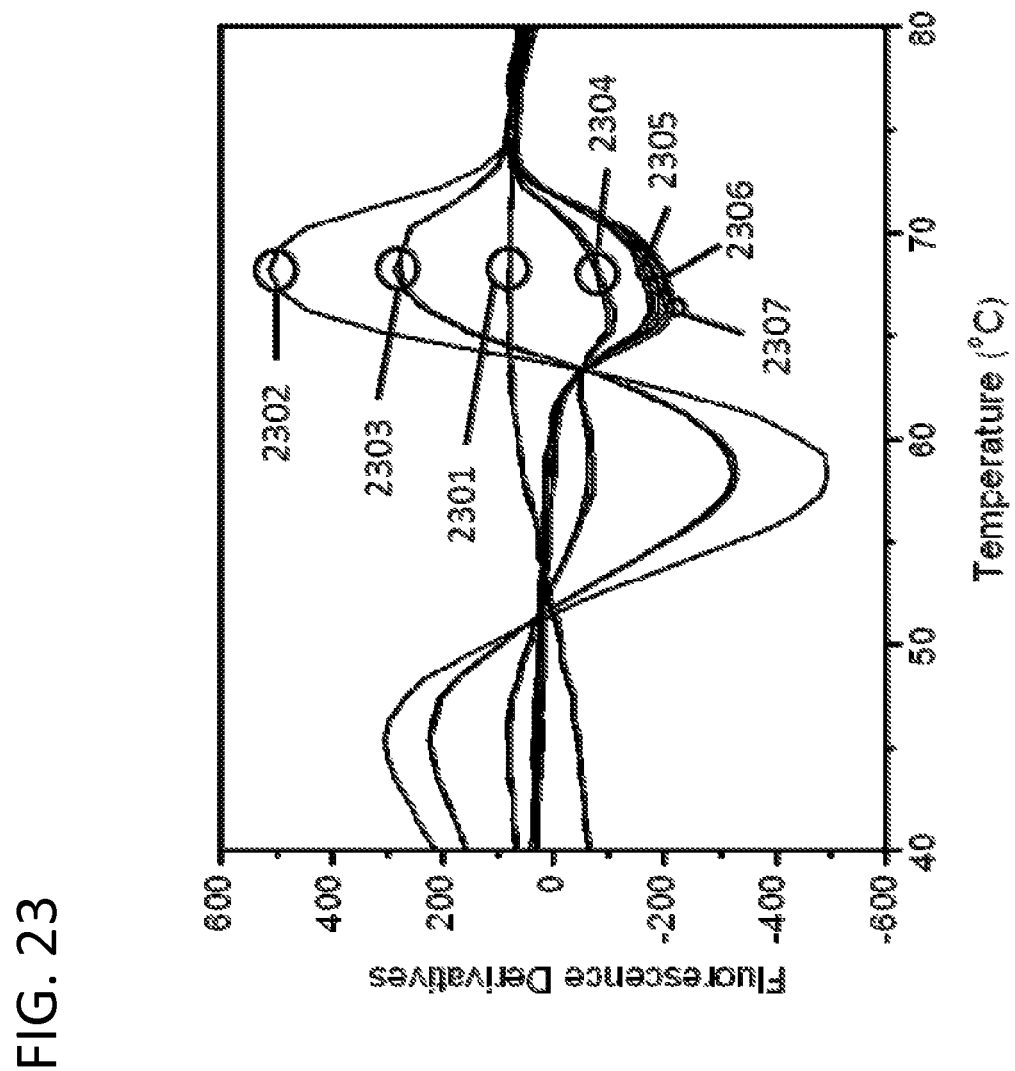
FIG. 23 is a graph containing melting curves (derivative of On-probe fluorescence versus temperature) following LATE-PCR amplifications described in Example 6 for samples containing first target sequence variant, second target sequence variant, or a mixture of first and second target sequence variants.

FIG. 23 shows the Quasar 670 melting curve (derivative of fluorescence intensities as a function of temperature), which is sometimes called a fluorescence signature, for various samples. Curves 2301 are the NTC; curves 2302 are 10,000 copies of the second variant; curves 2307 are 10,000 copies of the first variant; curves 2303 are 10,000 copies of the first variant with 1000 copies of the second variant; curves 2304 are 10,000 copies of the first variant with 100 copies of the second variant; curves 2305 are 10,000 copies of the first variant with 10 copies of the second variant; curves 2306 are 10,000 copies of the first variant with 1 copy of the second variant.

As shown in FIG. 23, pure second variant samples show a peak at 68° C., where the On-probe binds, and a negative peak at 58° C., where the Off-probe/Blocker binds. Pure first variant samples show a negative peak at 66° C. This is because the On-probe and the Off-probe (blocker) bind to first variant at the same temperature. When the fluorophore of the On-probe is adjacent to the quencher on the Off-probe, total fluorescence in the system is lower than when the On-probe is in solution, i.e. not bound to the target. Note that, although the same Lights-On/Lights-Off probe pair is used in this Example as was used in Example 4, the fluorescence signatures are different. In Example 4 pure first variant sample does not give any signal, while in the Example 6 pure first variant gives a negative peak. This is because in Example 4 no measurable amplification of first variant took place because the blocker was functional during all thermal cycles. In contrast, in Example 6 the blocker was functional only during the first two thermal cycles and evidently was not sufficiently optimized to fully block extension of the limiting primer on the first variant template strand during the first thermal cycle. In the following cycles, those strands of first variant that "escaped" were amplified just as efficiently as the second variant strands, because the blocker was no longer utilized. This example nonetheless shows the proof of principle of tailed primers.

The above assay can be further optimized by enlarging the Tm difference between the blocker and the limiting primer. This can be done by redesigning the 3' head of the limiting primer, redesigning the 5'tail of the limiting primer, adjusting the neck of the limiting primer, adjusting the concentration of the limiting primer, adjusting the concentration of the Off-probe/blocker, adjusting the temperature and/or time for blocker binding, adjusting the annealing temperature and/or time for limiting primer binding. Yet another optimization strategy would be to utilize a blocker whose 5' end is complementary to the target. This would guarantee that the 3' end of the primer lies on top of the 5' end of the blocker. Another improvement would to use a DNA polymerase that lacks a 5' exonuclease activity. This would make it impossible for the enzyme to cleave the 5' end of the blocker by either primer-dependent, or primer-independent cleavage. As one versed in the art will appreciate, many of the improvements listed above can be combined to achieve optimal selective inhibition of the primer on the first variant template. The greater the inhibition of extension of the limiting primer on the first variant template during the first thermal cycle, the less that amplicons from the first variant will accumulate.

FIG. 23 also shows the mixtures of 10,000 copies of first variant with 1000, 100 and 10 copies of second variant have fluorescence signatures different from those of the pure first variant and the pure second variant. Considering the curves for mixtures as overlays of two signatures of pure targets with different contributions of each target. So considered, 1000 copies of second variant in the mixture is roughly 10% of the sample, there is a positive peak at 68° C. and a negative peak at 58° C., which is similar to the peaks of pure second variant. This indicates that the majority of the final product is second variant sequence. And for 100 or 10 copies of second variant in the mixture, which is 1% or 0.1%, of the sample, one sees a negative peak at 58° C. and another negative peak at 66° C., which indicates the final product is predominantly second variant. For 1 copy of the second variant in the mixture, which is 0.01% of the sample, one sees that the curve is indistinguishable from the signature of the pure first variant.

Figure 24:
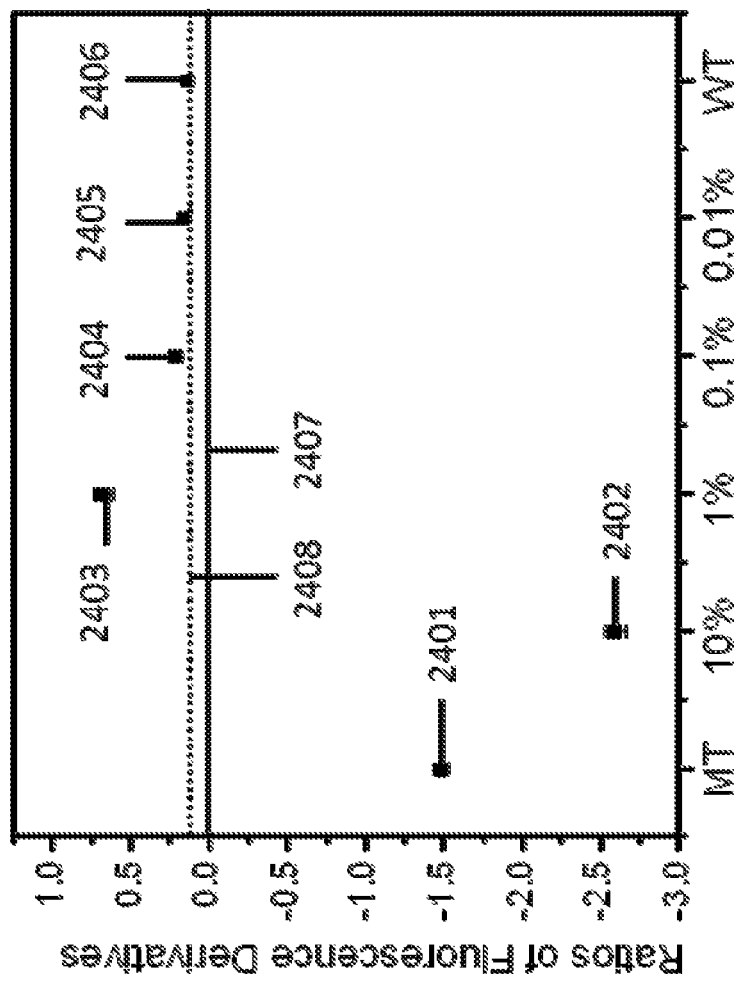
FIG. 24 is a graphic presentation of certain data in FIG. 23, showing ratios of the melting curve values at 58° C. to the melting curve values at 66° C.

FIG. 24 presents the information shown in FIG. 23 as ratios, namely, the ratio of the value of the fluorescence signature at 58° C. (after subtracting the value of the NTC) to the value of the fluorescence signature at 66° C. (after subtracting the value of the NTC). The ratios are presented graphically according to the percentage of second variant, or mutant, in the mixture, from 100% ("MT") to 0% ("WT"). Point 2401 is the ratio for 100% second variant; point 2402 is the ratio for 10% second variant; point 2403 is the ratio for 1% second variant; point 2404 is the ratio for 0.1% second variant; point 2405 is the ratio for 0.01% second variant; and point 2406 is for 0% second variant, 100% first variant. Line 2407 is a ratio value of 0, and line 2408 is the ratio value of 100% first variant.

As discussed above the conditions used in this example reduced the effective concentration of the 10,000 copies of the first variant to <200 copies. As shown in FIG. 24, the ratio values for pure second variant (100%) and for 10% of second variant both have negative values. That is because the peak at 66° C. is a positive number, and peak at 58° C. is a negative number. Therefore, any ratio value that is negative has majority of the second variant target. For lower second variant percentages, the ratio values are positive. That is because both peaks are negative. Different percentages of second variant in the starting mixture generate different percentages after amplification, so the ratio will reflect the initial percentage. Taking the ratio value for 100% first variant (point 2406) as a baseline, any sample that gives a distinguishable value is a mixture. From FIG. 24, one can tell the existence of 0.1% of the second variant in the existence of 99.9% of first variant. Further optimization of the system along the lines described above will result in greater selective amplification of the second variant, making it possible to distinguish mixtures containing less than 0.1% of the second variant from pure first variant.

The foregoing examples are by way of illustration only. Many changes and modifications that can be made to the methods described in the foregoing examples without departing from the invention will be apparent to persons of ordinary skill in the art. The examples do not limit the scope of the invention, which is defined rather by the claims set forth below.

We claim:

1. A primer-dependent DNA amplification method for selectively amplifying a rare second variant of a DNA target sequence in a sample containing an abundance of a first variant of the target sequence, where the second variant differs from the first variant by at least one nucleotide, comprising a) preparing a reaction mixture comprising the sample and amplification reagents that include a first linear primer and a second linear primer that bracket the target sequence, and additionally a primer-blocking hairpin oligonucleotide whose binding site on the target sequence is downstream from the target binding site of the first primer and includes said at least one nucleotide difference, wherein the target-binding sequence of the primer-blocking hairpin oligonucleotide is perfectly complementary to the first variant of the target sequence, wherein the binding site on the target sequence of the primer-blocking hairpin oligonucleotide overlaps by at least one nucleotide the binding site on the target sequence of the first primer, wherein the primer-blocking hairpin oligonucleotide has a concentration-adjusted melting temperature at the start of amplification versus the first variant of the target in the target template sequence that is at least 5° C. higher than its corresponding melting temperature versus the second variant of the target sequence, and wherein the primer-blocking hairpin oligonucleotide hybridizes to the first variant of the target sequence at a temperature at which the primers do not hybridize to the target sequence but at a rate that is at least five times slower than the rate at which the first primer binds to the target sequence; and b) subjecting the reaction mixture to a thermal-cycling protocol that includes repeated cycles of the steps of strand melting, primer annealing and primer extension, wherein at least the initial cycles include additionally, before the primer-annealing step, a blocker-binding step that has a temperature at which the primer-blocking hairpin oligonucleotide binds only to the first variant of the target sequence and the primers do not bind to the target sequence and that has a duration sufficient for the primer-blocking hairpin oligonucleotide to saturate in order to block extension on the first variant of the target sequence, and wherein the primer-annealing step has a duration insufficient for the primer-blocking hairpin oligonucleotide to bind to the second variant of the target sequence.

2. The method according to claim 1, wherein at the start of amplification the primer-blocking hairpin oligonucleotide has a concentration-adjusted melting temperature versus the first variant of the target in the target template sequence that is at least 7° C. higher than its corresponding melting temperature versus the second variant of the target sequence.

3. The method of claim 1 that is a non-symmetric amplification method wherein the first primer is a limiting primer and the second primer is an excess primer, wherein the ratio of excess primer to limiting primer is at least 5:1, and wherein the concentration-adjusted melting temperature of the limiting primer at the start of amplification is at least equal to the concentration-adjusted melting temperature of the excess primer at the start of amplification.

4. The method of claim 3 wherein the concentration-adjusted melting temperature of the limiting primer at the start of amplification is 3-10° C. higher than the concentration-adjusted melting temperature of the excess primer at the start of amplification.

5. The method of claim 1 wherein the reaction mixture includes at least one homogeneous detection reagent, and the method includes homogeneous detection of at least one amplified product.

6. The method of claim 5 wherein the primer-blocking hairpin oligonucleotide is labeled so as to participate is said homogeneous detection.

7. The method of claim 6 wherein the primer-blocking hairpin oligonucleotide includes a quencher at its 3' end, and the reaction mixture includes a short-stem molecular beacon probe that includes a fluorophore at its 5' end, that includes a quencher at its 3' end, and that hybridizes immediately downstream of the primer-blocking hairpin oligonucleotide.

8. The method of claim 1 wherein the thermal-cycling protocol includes multiple terminal cycles that do not include the blocker-binding step.

9. The method of claim 8 wherein the initial cycles that include the blocker-binding step are interrupted by one to ten cycles that do not include the blocker-binding step.

10. The method of claim 9 wherein the blocker-binding step is included in not more than two cycles following said interruption.

11. The method of claim 1 wherein the thermal cycling protocol includes at least ten initial cycles that include said blocker-binding step and a primer-annealing temperature sufficiently low for the first primer to bind but not sufficiently low for the second primer to bind, whereby the second variant is linearly amplified by binding and extension of the first primer prior to initiation of exponential amplification utilizing both primers.

12. The method of claim 1 wherein at least one of the primers is modified to have two concentration-adjusted melting temperatures during amplification, a low melting temperature versus the initial target sequence and a high melting temperature versus a product strand produced in the reaction, and wherein the thermal cycling protocol includes at least one cycle that has a primer annealing temperature sufficiently low for the at least one primer to bind at its low melting temperature and multiple cycles that have a primer annealing temperature sufficiently high for the at least one primer it bind only at its high melting temperature.

13. The method of claim 12 wherein the at least one modified primer is the second primer, and the second primer is mismatched to the target sequence.

14. The method of claim 12 wherein at least one primer is a tailed primer.

15. The method of claim 12, wherein the first and second primers are tailed primers having a linear 3' segment and a 5' tail that is not complementary to the target sequence, and wherein the thermal cycling protocol comprises not more than ten cycles that include the blocker-binding step and multiple subsequent cycles having a primer-annealing temperature sufficiently high that amplicon strands containing complements of the primer tails are exponentially amplified but other strands are not.

16. The method of claim 15 wherein at least one of the primers is a flip-tail primer.

17. The method of claim 16 wherein not more than two initial cycles include the blocker-binding step.

* * * * *